US009404115B2

(12) United States Patent
Yukawa et al.

(10) Patent No.: US 9,404,115 B2
(45) Date of Patent: Aug. 2, 2016

(54) CORYNEFORM BACTERIUM TRANSFORMANT AND PROCESS FOR PRODUCING PHENOL USING THE SAME

(75) Inventors: Hideaki Yukawa, Kyoto (JP); Masayuki Inui, Kyoto (JP)

(73) Assignee: GREEN PHENOL DEVELOPMENT CO., LTD., Kyoto (JP)

( * ) Notice: Subject to any disclaimer, the term of this patent is extended or adjusted under 35 U.S.C. 154(b) by 125 days.

(21) Appl. No.: 13/884,549

(22) PCT Filed: Nov. 9, 2011

(86) PCT No.: PCT/JP2011/075827
§ 371 (c)(1),
(2), (4) Date: Jun. 28, 2013

(87) PCT Pub. No.: WO2012/063862
PCT Pub. Date: May 18, 2012

(65) Prior Publication Data
US 2013/0273624 A1    Oct. 17, 2013

(30) Foreign Application Priority Data
Nov. 10, 2010   (JP) ................................. 2010-252357

(51) Int. Cl.
*C12N 1/21*        (2006.01)
*C12P 7/22*        (2006.01)
*C12N 9/88*        (2006.01)
*C12N 15/77*       (2006.01)

(52) U.S. Cl.
CPC    *C12N 15/77* (2013.01); *C12N 9/88* (2013.01); *C12P 7/22* (2013.01); *Y02P 20/52* (2015.11)

(58) Field of Classification Search
None
See application file for complete search history.

(56) References Cited

U.S. PATENT DOCUMENTS

| 6,210,937 | B1 * | 4/2001 | Ward et al. ..................... 435/146 |
| 7,056,742 | B2 | 6/2006 | Meyer et al. |
| 7,217,810 | B2 | 5/2007 | Knut et al. |
| 9,090,900 | B2 * | 7/2015 | Yukawa ................... C12N 9/88 |

FOREIGN PATENT DOCUMENTS

| CN | 1849390 A | 10/2006 |
| JP | 10-502244 | 3/1998 |
| JP | 2006-050914 A | 2/2006 |
| WO | WO-96/00788 A1 | 1/1996 |
| WO | WO-00/18943 A1 | 4/2000 |

OTHER PUBLICATIONS

Atsumi et al., Metabolic Engineer. 10:305-311, 2008.*
Brinkrolf et al., Genet. Mol. Res. 5:773-789, 2006.*
Kalinowski et al., J. Biotechnol. 104:5-25, 2003.*
Barker et al., "Environmentally Begnign Synthesis of Aromatic Compounds From D-Glucose", Dissertation, Michigan State University, 2001.*
GenBank Accession No. CP001875, May 2010, 54 pages.*
Yoon et al., Appl. Microbiol. Biotechnol. 74:131-139, 2007.*
Meiswinkel et al., Microb. Biotechnol. 6:131-140, 2012.*
Liu et al., "Corynebacterium glutamicum Contains 3-Deoxy-D-Arabino-Heptulosonate 7-Phosphate Synthases That Display Novel Biochemical Features", Appl. Environmen. Microbiol. 74:5497-5503, 2008.*
GenBank Accession No. CP001918, Apr. 2010, 2 pages.*
International Preliminary Report on Patentability in corrresponding PCT/JP2011/075827 dated May 14, 2013. (English Translation).
Lupa et al., "Properties of the reversible nonoxidative vanillate / 4-hydroxybenzoate decarboxylase from Bacillus subtilis," *Can. J. Microbiol.*, 54: 75-81 (2008).
Barker et al., "Microbial Synthesis of *p*-Hydroxybenzoic acid from Glucose," *Biotechnol. Bioeng.*, 76: 376-390 (2001).
Wierckx et al., "Engineering of solvent-tolerant Pseudomonas putida S12 for bioproduction of phenol from glucose," *Appl. Environ. Microbiol.*, 71: 8221-8227 (2005).
Wierckx et al., "Transcriptome analysis of a phenol-producing Pseudomonas putida S12 construct: genetic and physiological basis for improved production," *J. Bacteriol*, 190: 2822-2830 (2008).
International Search Report for PCT/JP2011/075827 dated Dec. 27, 2011.
Written Opinion for PCT/JP2011/075827 dated Dec. 27, 2011. (no translation).
Chinese doctor Thesis, "Study on the Regulation of Metabolic Pathway in Aromatic Amino Acids Biosynthesis", Published Sep. 11, 2003, 2 pgs.
Extended European Search Report in European Application No. 11839480.8 dated Mar. 25, 2014.
Huang et al., "Genetic and biochemical characterization of a 4-hydroxybenzoate hydroxylase from Corynebacterium glutamicum," *Appl Microbiol Biotechnol*, vol. 78, pp. 75-83, 2008.
Matsui et al., "Purification, characterization, and gene cloning of 4-hydroxybenzoate decarboxylase of *Enterobacter cloacae* P240," *Arch Microbiol*, vol. 186, pp. 21-29 (2006).
Juteau et al., "*Cryptanaerobacter phenolicus* gen. nov., sp. nov., an anaerobe that transforms phenol into benzoate via 4-hydroxybenzoate," *International Journal of Systematic and Evolutionary Microbiology*, vol. 55, pp. 245-250 (2005).

(Continued)

*Primary Examiner* — David J Steadman
(74) *Attorney, Agent, or Firm* — Marshall, Gerstein & Borun LLP

(57) ABSTRACT

Provided is a phenol-producing transformant constructed by transferring a gene which encodes an enzyme having chorismate-pyruvate lyase activity and a gene which encodes an enzyme having 4-hydroxybenzoate decarboxylase activity into a coryneform bacterium as a host. Also provided is a process for producing phenol, which comprises a step of allowing the transformant to react in a reaction mixture containing a saccharide under reducing conditions, and a step of collecting phenol from the reaction mixture.

14 Claims, 4 Drawing Sheets

(56) References Cited

OTHER PUBLICATIONS

Yoshimi Kikuchi et al., "Mutational Analysis of the Feedback Sites of Phenylalanine-Sensitive 3-Deoxy-$_D$-arabino-Heptulosonate-7-Phosphate Synthase of *Escherichia coli*", Appl. Environ. Microbiol., Feb. 1997, vol. 63, No. 2, pp. 761-762.

Ronald Schoner et al., "3-Deoxy-$_D$-*arabino*-heptulosonate 7-Phosphate Synthase", J. Biol. Chem., vol. 251, No. 18, Sep. 25, 1976, pp. 5440-5447.

Jill M. Ray et al. "Mutational Analysis of the Catalytic and Feedback Sites of the Tryptophan-Sensitive 3-Deoxy-$_D$-*arabino*-Heptulosonate-7-Phosphate Synthase of *Escherichia coli*", J. of Bacteriol., Dec. 1988, vol. 170, No. 12, pp. 5500-5506.

Heinaru et al., "Three types of phenol and p-cresol catabolism in phenol- and p-cresol-degrading bacteria isolated from river water continuously polluted with phenolic compounds," *FEMS Microbiology Biology*, vol. 31, No. 3, pp. 195-205 (2000).

\* cited by examiner

SEQUENCE LISTING

<160> NUMBER OF SEQ ID NOS: 122

<210> SEQ ID NO 1
<211> LENGTH: 1195
<212> TYPE: DNA
<213> ORGANISM: Corynebacterium casei

<400> SEQUENCE: 1

| | | | | | | |
|---|---|---|---|---|---|---|
| atgaaaaccg | accgtgcacg | ctcgtgtgag | aaagtcagct | acatgagacc | aactacccgc | 60 |
| cctgagggac | gctttgagca | gctgtggctg | ccgctgtggc | cattggcaag | cgatgacctc | 120 |
| cgtgagggca | tttaccgcac | ctcacggaag | aacgcgctgg | ataagcgcta | cgtcgaagcc | 180 |
| aatcccgacg | cgctctctaa | cctcctggtc | gttgacatcg | accaggagga | cgcgcttttg | 240 |
| cgctcttttgt | gggacaggga | ggactggaga | cctaacgcgg | tggttgaaaa | ccccttaaac | 300 |
| gggcacgcac | acgctgtctg | gcgctcgcg | gagccattta | cccgcaccga | atacgccaaa | 360 |
| cgcaagcctt | tggcctatgc | cgcggctgtc | accgaaggcc | tacggcgctc | tgtcgatggc | 420 |
| gatagcggat | actccgggct | gatcaccaaa | aaccccgagc | acactgcatg | ggatagtcac | 480 |
| tggatcaccg | ataagctgta | tacgctcgat | gagctgcgct | tttggctcga | agaaaccggc | 540 |
| tttatgccgc | ctgcgtcctg | gaggaaaacg | cggcggttct | cgccagttgg | tctaggtcgt | 600 |
| aattgcgcac | tctttgaaag | cgcacgtacg | tgggcatatc | gggaggtcag | aaagcatttt | 660 |
| ggagacgctg | acggcctagg | ccgcgcaatc | caaaccaccg | cgcaagcact | taaccaagag | 720 |
| ctgtttgatg | aaccactacc | tgtggccgaa | gttgactgta | ttgccaggtc | aatccataaa | 780 |
| tggatcatca | ccaagtcacg | catgtggaca | gacggcgccg | ccgtctacga | cgccacattc | 840 |
| accgcaatgc | aatccgcacg | cgggaagaaa | ggctggcaac | gaagcgctga | ggtgcgtcgt | 900 |
| gaggctggac | atactctttg | gaggaacatt | ggctaaggtt | tatgcacgtt | atccacgcaa | 960 |
| cggaaaaaca | gcccgcgagc | tggcagaacg | tgccggtatg | tcggtgagaa | cagctcaacg | 1020 |
| atggacttcc | gaaccgcgtg | aagtgttcat | taaacgtgcc | aacgagaagc | gtgctcgcgt | 1080 |
| ccaggagctg | cgcgccaaag | gtctgtccat | gcgcgctatc | gcggcagaga | ttggttgctc | 1140 |
| ggtgggcacg | gttcaccgct | acgtcaaaga | agttgaagag | aagaaaaccg | cgtaa | 1195 |

<210> SEQ ID NO 2
<211> LENGTH: 2675
<212> TYPE: DNA
<213> ORGANISM: Artificial sequence
<220> FEATURE:
<223> OTHER INFORMATION: pHSG298

<400> SEQUENCE: 2

| | | | | | | |
|---|---|---|---|---|---|---|
| gaggtctgcc | tcgtgaagaa | ggtgttgctg | actcatacca | ggcctgaatc | gccccatcat | 60 |
| ccagccagaa | agtgagggag | ccacggttga | tgagagcttt | gttgtaggtg | gaccagttgg | 120 |
| tgattttgaa | cttttgcttt | gccacggaac | ggtctgcgtt | gtcgggaaga | tgcgtgatct | 180 |
| gatccttcaa | ctcagcaaaa | gttcgattta | ttcaacaaag | ccacgttgtg | tctcaaaatc | 240 |
| tctgatgtta | cattgcacaa | gataaaaata | tatcatcatg | aacaataaaa | ctgtctgctt | 300 |
| acataaacag | taatacaagg | ggtgttatga | gccatattca | acgggaaacg | tcttgctcga | 360 |
| agccgcgatt | aaattccaac | atggatgctg | atttatatgg | gtataaatgg | gctcgcgata | 420 |
| atgtcgggca | atcaggtgcg | acaatctatc | gattgtatgg | gaagcccgat | gcgccagagt | 480 |
| tgtttctgaa | acatggcaaa | ggtagcgttg | ccaatgatgt | tacagatgag | atggtcagac | 540 |
| taaactggct | gacggaattt | atgcctcttc | cgaccatcaa | gcattttatc | cgtactcctg | 600 |

-continued

```
atgatgcatg gttactcacc actgcgatcc ccgggaaaac agcattccag gtattagaag    660
aatatcctga ttcaggtgaa aatattgttg atgcgctggc agtgttcctg cgccggttgc    720
attcgattcc tgtttgtaat tgtcctttta acagcgatcg cgtatttcgt ctcgctcagg    780
cgcaatcacg aatgaataac ggtttggttg atgcgagtga ttttgatgac gagcgtaatg    840
gctggcctgt tgaacaagtc tggaaagaaa tgcataagct tttgccattc tcaccggatt    900
cagtcgtcac tcatggtgat ttctcacttg ataaccttat ttttgacgag gggaaattaa    960
taggttgtat tgatgttgga cgagtcggaa tcgcagaccg ataccaggat cttgccatcc   1020
tatggaactg cctcggtgag tttttctcctt cattacagaa acggcttttt caaaaatatg   1080
gtattgataa tcctgatatg aataaattgc agtttcattt gatgctcgat gagttttttct  1140
aatcagaatt ggttaattgg ttgtaacact ggcagagcat tacgctgact tgacgggacg   1200
gcggctttgt tgaataaatc gcattcgcca ttcaggctgc gcaactgttg ggaagggcga   1260
tcggtgcggg cctcttcgct attacgccag ctggcgaaag ggggatgtgc tgcaaggcga   1320
ttaagttggg taacgccagg gttttcccag tcacgacgtt gtaaaacgac ggccagtgcc   1380
aagcttgcat gcctgcaggt cgactctaga ggatccccgg gtaccgagct cgaattcgta   1440
atcatgtcat agctgtttcc tgtgtgaaat tgttatccgc tcacaattcc acacaacata   1500
cgagccggaa gcataaagtg taaagcctgg ggtgcctaat gagtgagcta actcacatta   1560
attgcgttgc gctcactgcc cgctttccag tcgggaaacc tgtcgtgcca gctgcattaa   1620
tgaatcggcc aacgcgcggg gagaggcggt ttgcgtattg gcgaacttttt gctgagttga   1680
aggatcagat cacgcatctt cccgacaacg cagaccgttc cgtggcaaag caaaagttca   1740
aaatcagtaa ccgtcagtgc cgataagttc aaagttaaac ctggtgttga taccaacatt   1800
gaaacgctga tcgaaaacgc gctgaaaaac gctgctgaat gtgcgagctt cttccgcttc   1860
ctcgctcact gactcgctgc gctcggtcgt tcggctgcgg cgagcggtat cagctcactc   1920
aaaggcggta atacggttat ccacagaatc aggggataac gcaggaaaga acatgtgagc   1980
aaaaggccag caaaaggcca ggaaccgtaa aaaggccgcg ttgctggcgt ttttccatag   2040
gctccgcccc cctgacgagc atcacaaaaa tcgacgctca agtcagaggt ggcgaaaccc   2100
gacaggacta taaagatacc aggcgtttcc ccctggaagc tccctcgtgc gctctcctgt   2160
tccgaccctg ccgcttaccg gatacctgtc cgcctttctc ccttcgggaa gcgtggcgct   2220
ttctcaatgc tcacgctgta ggtatctcag ttcggtgtag gtcgttcgct ccaagctggg   2280
ctgtgtgcac gaaccccccg ttcagcccga ccgctgcgcc ttatccggta actatcgtct   2340
tgagtccaac ccggtaagac acgacttatc gccactggca gcagccactg gtaacaggat   2400
tagcagagcg aggtatgtag gcggtgctac agagttcttg aagtggtggc ctaactacgg   2460
ctacactaga aggacagtat ttggtatctg cgctctgctg aagccagtta ccttcggaaa   2520
aagagttggt agctcttgat ccggcaaaca aaccaccgct ggtagcggtg ttttttttgt   2580
ttgcaagcag cagattacgc gcagaaaaaa aggatctcaa gaagatcctt tgatcttttc   2640
tacggggtct gacgctcagt ggaacgatcc gtcga                              2675
```

<210> SEQ ID NO 3
<211> LENGTH: 25
<212> TYPE: DNA
<213> ORGANISM: Artificial sequence
<220> FEATURE:
<223> OTHER INFORMATION: PCR primer -continued

<400> SEQUENCE: 3
atagatctag aacgtccgta ggagc                                    25

<210> SEQ ID NO 4
<211> LENGTH: 26
<212> TYPE: DNA
<213> ORGANISM: Artificial sequence
<220> FEATURE:
<223> OTHER INFORMATION: PCR primer

<400> SEQUENCE: 4
atagatctga cttggttacg atggac                                   26

<210> SEQ ID NO 5
<211> LENGTH: 27
<212> TYPE: DNA
<213> ORGANISM: Artificial sequence
<220> FEATURE:
<223> OTHER INFORMATION: PCR primer

<400> SEQUENCE: 5
atagatctag gtttcccgac tggaaag                                  27

<210> SEQ ID NO 6
<211> LENGTH: 28
<212> TYPE: DNA
<213> ORGANISM: Artificial sequence
<220> FEATURE:
<223> OTHER INFORMATION: PCR primer

<400> SEQUENCE: 6
atagatctcg tgccagctgc attaatga                                 28

<210> SEQ ID NO 7
<211> LENGTH: 1885
<212> TYPE: DNA
<213> ORGANISM: Unknown
<220> FEATURE:
<223> OTHER INFORMATION: pCG1-ori

<400> SEQUENCE: 7
agcatggtcg tcacagagct ggaagcggca gcgagaatta tccgcgatcg tggcgcggtg      60
cccgcaggca tgacaaacat cgtaaatgcc gcgtttcgtg tggccgtggc cgcccaggac     120
gtgtcagcgc cgccaccacc tgcaccgaat cggcagcagc gtcgcgcgtc gaaaaagcgc     180
acaggcggca agaagcgata agctgcacga ataccgaaaa atgttgaacg ccccgtgag      240 cggtaactca cagggcgtcg ctaaccccca gtccaaacc tgggagaaag cgctcaaaaa      300
tgactctagc ggattcacga gacattgaca caccggcctg gaaattttcc gctgatctgt    360
tcgacaccca tcccgagctc gcgctgcgat cacgtggctg gacgagcgaa gaccgccgcg    420
aattcctcgc tcacctgggc agagaaaatt tccagggcag caagaccgc gacttcgcca     480 gcgcttggat caaagacccg gacacgggag aaacacagcc gaagttatac cgagttggtt    540
caaaatcgct tgcccggtgc cagtatgttg ctctgacgca cgcgcagcac gcagccgtgc    600
ttgtcctgga cattgatgtg ccgagccacc aggccggcgg gaaaatcgag cacgtaaacc    660
ccgaggtcta cgcgattttg gagcgctggg cacgcctgga aaagcgcca gcttggatcg    720 gcgtgaatcc actgagcggg aaatgccagc tcatctggct cattgatccg gtgtatgccg    780
cagcaggcat gagcagcccg aatatgcgcc tgctggctgc aacgaccgag gaaatgaccc    840
gcgttttcgg cgctgaccag gcttttttcac ataggctgag ccggtggcca ctgcacgtct    900

```
ccgacgatcc caccgcgtac cgctggcatg cccagcacaa tcgcgtggat cgcctagctg    960
atcttatgga ggttgctcgc atgatctcag gcacagaaaa acctaaaaaa cgctatgagc   1020
aggagttttc tagcggacgg gcacgtatcg aagcggcaag aaaagccact gcggaagcaa   1080
aagcacttgc cacgcttgaa gcaagcctgc cgagcgccgc tgaagcgtct ggagagctga   1140
tcgacggcgt ccgtgtcctc tggactgctc cagggcgtgc cgcccgtgat gagacggctt   1200
ttcgccacgc tttgactgtg ggataccagt taaaagcggc tggtgagcgc ctaaaagaca   1260
ccaagatcat cgacgcctac gagcgtgcct acaccgtcgc tcaggcggtc ggagcagacg   1320
gccgtgagcc tgatctgccg ccgatgcgtg accgccagac gatggcgcga cgtgtgcgcg   1380
gctacgtcgc taaaggccag ccagtcgtcc ctgctcgtca gacagagacg cagagcagcc   1440
gagggcgaaa agctctggcc actatgggaa gacgtggcgg taaaaaggcc gcagaacgct   1500
ggaaagaccc aaacagtgag tacgcccgag cacagcgaga aaaactagct aagtccagtc   1560
aacgacaagc taggaaagct aaaggaaatc gcttgaccat tgcaggttgg tttatgactg   1620
ttgagggaga gactggctcg tggccgacaa tcaatgaagc tatgtctgaa tttagcgtgt   1680
cacgtcagac cgtgaataga gcacttaagt ctgcgggcat tgaacttcca cgaggacgcc   1740
gtaaagcttc ccagtaaatg tgccatctcg taggcagaaa acggttcccc ccgtaggggt   1800
ctctctcttg gcctcctttc taggtcgggc tgattgctct tgaagctctc tagggggggct   1860 cacaccatag gcagataacg gttcc                                         1885
```

<210> SEQ ID NO 8
<211> LENGTH: 2227
<212> TYPE: DNA
<213> ORGANISM: Unknown
<220> FEATURE:
<223> OTHER INFORMATION: pHSG398

<400> SEQUENCE: 8

```
acggaagatc acttcgcaga ataaataaat cctggtgtcc ctgttgatac cgggaagccc    60
tgggccaact tttggcgaaa atgagacgtt gatcggcacg taagaggttc aactttcac    120 cataatgaaa taagatcact accgggcgta ttttttgagt tatcgagatt ttcaggagct    180
aaggaagcta aaatggagaa aaaaatcact ggatatacca ccgttgatat atcccaatgg    240
catcgtaaag aacatttttga ggcatttcag tcagttgctc aatgtaccta taaccagacc    300
gttcagctgg atattacggc cttttttaaag accgtaaaga aaaataagca caagttttat    360
ccggccttta ttcacattct tgcccgcctg atgaatgctc atccggaatt tcgtatggca    420
atgaaagacg gtgagctggt gatatgggat agtgttcacc cttgttacac cgttttccat    480
gagcaaactg aaacgttttc atcgctctgg agtgaatacc acgacgattt ccggcagttt    540
ctacacatat attcgcaaga tgtggcgtgt tacggtgaaa acctggccta tttccctaaa    600
gggtttattg agaatatgtt tttcgtctca gccaatccct gggtgagttt caccagtttt    660
gatttaaacg tggccaatat ggacaacttc ttcgccccccg ttttcaccat gggcaaatat    720
tatacgcaag gcgacaaggt gctgatgccg ctggcgattc aggttcatca tgccgtctgt    780
gatggcttcc atgtcggcag aatgcttaat gaattacaac agtactgcga tgagtggcag    840
ggcggggcgt aattttttta aggcagttat tggtgccctt aaacgcctgg tgctacgcct    900
gaataagtga ataaagcgg atgaatggca gaaattcagc ttggcccagt gccaagctcc    960
aatacgcaaa ccgcctctcc ccgcgcgttg gccgattcat taatgcagct ggcacgacag   1020
```

```
gtttcccgac tggaaagcgg gcagtgagcg caacgcaatt aatgtgagtt agctcactca    1080
ttaggcaccc caggctttac actttatgct tccggctcgt atgttgtgtg gaattgtgag    1140
cggataacaa tttcacacag gaaacagcta tgaccatgat tacgaattcg agctcggtac    1200
ccggggatcc tctagagtcg acctgcaggc atgcaagctt ggcactggcc gtcgttttac    1260
aacgtcgtga ctgggaaaac cctggcgtta cccaacttaa tcgccttgca gcacatcccc    1320
ctttcgccag ctggcgtaat agcgaagagg cccgcaccga tcgcccttcc caacagttgc    1380
gcagcctgaa tggcgaatga gcttcttccg cttcctcgct cactgactcg ctgcgctcgg    1440
tcgttcggct gcggcgagcg gtatcagctc actcaaaggc ggtaatacgg ttatccacag    1500
aatcagggga taacgcagga agaacatgt gagcaaaagg ccagcaaaag gccaggaacc    1560
gtaaaaaggc cgcgttgctg cgttttttcc ataggctccg ccccctgac gagcatcaca    1620 aaaatcgacg ctcaagtcag aggtggcgaa acccgacagg actataaaga taccaggcgt    1680
ttccccctgg aagctccctc gtgcgctctc ctgttccgac cctgccgctt accggatacc    1740
tgtccgcctt tctcccttcg ggaagcgtgg cgctttctca atgctcacgc tgtaggtatc    1800
tcagttcggt gtaggtcgtt cgctccaagc tgggctgtgt gcacgaaccc ccgttcagc    1860 ccgaccgctg cgccttatcc ggtaactatc gtcttgagtc aacccggta agacacgact    1920 tatcgccact ggcagcagcc actggtaaca ggattagcag agcgaggtat gtaggcggtg    1980
ctacagagtt cttgaagtgg tggcctaact acggctacac tagaaggaca gtatttggta    2040
tctgcgctct gctgaagcca gttaccttcg gaaaagagt tggtagctct tgatccggca     2100
aacaaaccac cgctggtagc ggtggttttt tgtttgcaa gcagcagatt acgcgcagaa    2160
aaaaaggatc tcaagaagat cctttgatct tttctacggg gtctgacgct cagtggaact    2220
ccgtcga                                                              2227

<210> SEQ ID NO 9
<211> LENGTH: 26
<212> TYPE: DNA
<213> ORGANISM: Artificial sequence
<220> FEATURE:
<223> OTHER INFORMATION: PCR primer

<400> SEQUENCE: 9
atagatctag catggtcgtc acagag                                         26

<210> SEQ ID NO 10
<211> LENGTH: 28
<212> TYPE: DNA
<213> ORGANISM: Artificial sequence
<220> FEATURE:
<223> OTHER INFORMATION: PCR primer

<400> SEQUENCE: 10
atagatctgg aaccgttatc tgcctatg                                       28

<210> SEQ ID NO 11
<211> LENGTH: 28
<212> TYPE: DNA
<213> ORGANISM: Artificial sequence
<220> FEATURE:
<223> OTHER INFORMATION: PCR primer

<400> SEQUENCE: 11
atagatctgt cgaacggaag atcacttc                                       28
```

```
<210> SEQ ID NO 12
<211> LENGTH: 26
<212> TYPE: DNA
<213> ORGANISM: Artificial sequence
<220> FEATURE:
<223> OTHER INFORMATION: PCR primer

<400> SEQUENCE: 12
atagatctag ttccactgag cgtcag                                          26

<210> SEQ ID NO 13
<211> LENGTH: 4125
<212> TYPE: DNA
<213> ORGANISM: Unknown
<220> FEATURE:
<223> OTHER INFORMATION: pCRB11

<400> SEQUENCE: 13
ctgtcgaacg gaagatcact tcgcagaata aataaatcct ggtgtccctg ttgataccgg     60
gaagccctgg gccaactttt ggcgaaaatg agacgttgat cggcacgtaa gaggttccaa    120
ctttcaccat aatgaaataa gatcactacc gggcgtattt tttgagttat cgagattttc    180
aggagctaag gaagctaaaa tggagaaaaa atcactggat ataccaccg ttgatatatc     240 ccaatggcat cgtaaagaac attttgaggc atttcagtca gttgctcaat gtacctataa    300
ccagaccgtt cagctggata ttacggcctt tttaaagacc gtaaagaaaa ataagcacaa    360
gttttatccg gcctttattc acattcttgc ccgcctgatg aatgctcatc cggaatttcg    420
tatggcaatg aaagacggtg agctggtgat atgggatagt gttcacccct tgttacaccg    480 ttttccatgag caaactgaaa cgttttcatc gctctggagt gaataccacg acgatttccg    540
gcagtttcta cacatatatt cgcaagatgt ggcgtgttac ggtgaaaacc tggcctattt    600
ccctaaaggg tttattgaga atatgttttt cgtctcagcc aatccctggg tgagtttcac    660
cagttttgat ttaaacgtgg ccaatatgga caacttcttc gcccccgttt tcaccatggg    720
caaatattat acgcaaggcg acaaggtgct gatgccgctg gcgattcagg ttcatcatgc    780
cgtttgtgat ggcttccatg tcggcagaat gcttaatgaa ttacaacagt actgcgatga    840
gtggcagggc ggggcgtaat tttttttaagg cagttattgg tgcccttaaa cgcctggttg    900
ctacgcctga ataagtgata taagcggat gaatggcaga aattcagctt ggcccagtgc    960
caagctccaa tacgcaaacc gcctctcccc gcgcgttggc cgattcatta atgcagctgg   1020
cacgacaggt ttcccgactg gaaagcgggc agtgagcgca acgcaattaa tgtgagttag   1080
ctcactcatt aggcacccca ggctttacac tttatgcttc cggctcgtat gttgtgtgga   1140
attgtgagcg gataacaatt tcacacagga aacagctatg accatgatta cgaattcgag   1200
ctcggtaccc ggggatcctc tagagtcgac ctgcaggcat gcaagcttgg cactggccgt   1260
cgttttacaa cgtcgtgact gggaaaaccc tggcgttacc caacttaatc gccttgcagc   1320
acatccccct ttcgccagct ggcgtaatag cgaagaggcc cgcaccgatc gcccttccca   1380
acagttgcgc agcctgaatg gcgaatgagc ttcttccgct tcctcgctca ctgactcgct   1440
gcgctcggtc gttcggctgc ggcgagcggt atcagctcac tcaaaggcgg taatacggtt   1500
atccacagaa tcaggggata acgcaggaaa gaacatgtga gcaaaaggcc agcaaaaggc   1560
caggaaccgt aaaaaggccg cgttgctggc gtttttccat aggctccgcc cccctgacga   1620
gcatcacaaa aatcgacgct caagtcagag gtggcgaaac ccgacaggac tataaagata   1680
ccaggcgttt ccccctggaa gctccctcgt gcgctctcct gttccgaccc tgccgcttac   1740
```

```
cggatacctg tccgcctttc tcccttcggg aagcgtggcg ctttctcata gctcacgctg    1800
taggtatctc agttcggtgt aggtcgttcg ctccaagctg ggctgtgtgc acgaaccccc    1860
cgttcagccc gaccgctgcg ccttatccgg taactatcgt cttgagtcca acccggtaag    1920
acacgactta tcgccactgg cagcagccac tggtaacagg attagcagag cgaggtatgt    1980
aggcggtgct acagagttct tgaagtggtg gcctaactac ggctacacta agaacagt      2040 atttggtatc tgcgctctgc tgaagccagt taccttcgga aaagagttg gtagctcttg     2100 atccggcaaa caaccaccg ctggtagcgg tggtttttt gtttgcaagc agcagattac      2160
gcgcagaaaa aaaggatctc aagaagatcc tttgatcttt tctacggggt ctgacgctca    2220
gtggaactag atctagcatg gtcgtcacag agctggaagc ggcagcgaga attatccgcg    2280
atcgtggcgc ggtgcccgca ggcatgacaa acatcgtaaa tgccgcgttt cgtgtggccg    2340
tggccgccca ggacgtgtca gcgccgccac cacctgcacc gaatcggcag cagcgtcgcg    2400
cgtcgaaaaa gcgcacaggc ggcaagaagc gataagctgc acgaatacct gaaaaatgtt    2460
gaacgccccg tgagcggtaa ctcacaggggc gtcggctaac ccccagtcca aacctgggag    2520
aaagcgctca aaaatgactc tagcggattc acgagacatt gacacaccgg cctggaaatt    2580
ttccgctgat ctgttcgaca cccatcccga gctcgcgctg cgatcacgtg gctggacgag    2640
cgaagaccgc cgcgaattcc tcgctcacct gggcagagaa aatttccagg gcagcaagac    2700
ccgcgacttc gccagcgctt ggatcaaaga cccggacacg ggagaaacac agccgaagtt    2760
ataccgagtt ggttcaaaat cgcttgcccg gtgccagtat gttgctctga cgcacgcgca    2820
gcacgcagcc gtgcttgtcc tggacattga tgtgccgagc caccaggccg gcgggaaaat    2880
cgagcacgta aaccccgagg tctacgcgat tttggagcgc tgggcacgcc tggaaaaagc    2940
gccagcttgg atcggcgtga atccactgag cgggaaatgc cagctcatct ggctcattga    3000
tccggtgtat gccgcagcag gcatgagcag cccgaatatg cgcctgctgg ctgcaacgac    3060
cgaggaaatg acccgcgttt tcggcgctga ccaggctttt tcacataggc tgagccggtg    3120
gccactgcac gtctccgacg atcccaccgc gtaccgctgg catgcccagc acaatcgcgt    3180
ggatcgccta gctgatctta tggaggttgc tcgcatgatc tcaggcacag aaaaacctaa    3240
aaaacgctat gagcaggagt tttctagcgg acgggcacgt atcgaagcgg caagaaaagc    3300
cactgcggaa gcaaaagcac ttgccacgct tgaagcaagc ctgccgagcg ccgctgaagc    3360
gtctggagag ctgatcgacg gcgtccgtgt cctctggact gctccagggc gtgccgcccg    3420
tgatgagacg gcttttcgcc acgctttgac tgtgggatac cagttaaaag cggctggtga    3480
gcgcctaaaa gacaccaaga tcatcgacgc ctacgagcgt gcctacaccg tcgctcaggc    3540
ggtcggagca gacggccgtg agcctgatct gccgccgatg cgtgaccgcc agacgatggc    3600
gcgacgtgtg cgcggctacg tcgctaaagg ccagccagtc gtccctgctc gtcagacaga    3660
gacgcagagc agccgagggc gaaaagctct ggccactatg ggaagacgtg gcggtaaaaa    3720
ggccgcagaa cgctggaaag acccaaacag tgagtacgcc cgagcacagc gagaaaaact    3780
agctaagtcc agtcaacgac aagctaggaa agctaaagga aatcgcttga ccattgcagg    3840
ttggtttatg actgttgagg gagagactgg ctcgtggccg acaatcaatg aagctatgtc    3900
tgaatttagc gtgtcacgtc agaccgtgaa tagagcactt aagtctgcgg gcattgaact    3960
tccacgagga cgccgtaaag cttcccagta aatgtgccat tcgtaggca gaaaacggtt     4020 cccccgtag gggtctctct cttggcctcc tttctaggtc gggctgattg ctcttgaagc     4080
tctctagggg ggctcacacc ataggcagat aacggttcca gatct                    4125
```

<210> SEQ ID NO 14
<211> LENGTH: 465
<212> TYPE: DNA
<213> ORGANISM: Unknown
<220> FEATURE:
<223> OTHER INFORMATION: zeocin resistance gene

<400> SEQUENCE: 14

```
tagcttatcc tcagtcctgc tcctctgcca caaagtgcac gcagttgccg gccgggtcgc      60
gcagggcgaa ctcccgcccc cacggctgct cgccgatctc ggtcatggcc ggcccggagg     120
cgtcccggaa gttcgtggac acgacctccg accactcggc gtacagctcg tccaggccgc     180
gcacccacac ccaggccagg gtgttgtccg gcaccacctg gtcctggacc gcgctgatga     240
acagggtcac gtcgtcccgg accacaccgg cgaagtcgtc ctccacgaag tcccgggaga     300
acccgagccg gtcggtccag aactcgaccg ctccggcgac gtcgcgcgcg gtgagcaccg     360
gaacggcact ggtcaacttg gccatgatgg ccctcctata gtgagtcgta ttatactatg     420
ccgatatact atgccgatga ttaattgtca aaacagcgtg gatgg                    465
```

<210> SEQ ID NO 15
<211> LENGTH: 28
<212> TYPE: DNA
<213> ORGANISM: Artificial sequence
<220> FEATURE:
<223> OTHER INFORMATION: PCR primer

<400> SEQUENCE: 15

```
atgatatccg aagtgatctt ccgttcga                                         28
```

<210> SEQ ID NO 16
<211> LENGTH: 28
<212> TYPE: DNA
<213> ORGANISM: Artificial sequence
<220> FEATURE:
<223> OTHER INFORMATION: PCR primer

<400> SEQUENCE: 16

```
atgatatcaa ggcagttatt ggtgccct                                         28
```

<210> SEQ ID NO 17
<211> LENGTH: 28
<212> TYPE: DNA
<213> ORGANISM: Artificial sequence
<220> FEATURE:
<223> OTHER INFORMATION: PCR primer

<400> SEQUENCE: 17

```
atgatatcta gcttatcctc agtcctgc                                         28
```

<210> SEQ ID NO 18
<211> LENGTH: 28
<212> TYPE: DNA
<213> ORGANISM: Artificial sequence
<220> FEATURE:
<223> OTHER INFORMATION: PCR primer

<400> SEQUENCE: 18

```
atgatatccc atccacgctg ttttgaca                                         28
```

<210> SEQ ID NO 19
<211> LENGTH: 551
<212> TYPE: DNA

<213> ORGANISM: Corynebacterium glutamicum

<400> SEQUENCE: 19

```
ccgaagatct gaagattcct gatacaaatt ctgttgtgac ggaagatttg ttggaagaaa      60
tctagtcgct cgtctcataa aaacgaccga gcctattggg attaccattg aagccagtgt     120
gagttgcatc acactggctt caaatctgag actttacttt gtggattcac gggggtgtag     180
tgcaattcat aattagcccc attcggggga gcagatcgcg gcgcgaacga tttcaggttc     240
gttccctgca aaactatttt agcgcaagtg ttggaaatgc ccccgtctgg ggtcaatgtc     300
tatttttgaa tgtgtttgta tgattttgaa tccgctgcaa aatctttgtt tccccgctaa     360
agttggggac aggttgacac ggagttgact cgacgaatta tccaatgtga gtaggtttgg     420
tgcgtgagtt ggaaaatttc gccatactcg cccttgggtt ctgtcagctc aagaattctt     480
gagtgaccga tgctctgatt gacctaactg cttgacacat tgcatttcct acaatcttta     540
gaggagacac a                                                          551
```

<210> SEQ ID NO 20
<211> LENGTH: 425
<212> TYPE: DNA
<213> ORGANISM: Unknown
<220> FEATURE:
<223> OTHER INFORMATION: rrnBT1T2 terminator

<400> SEQUENCE: 20

```
ctgttttggc ggatgagaga agattttcag cctgatacag attaaatcag aacgcagaag      60
cggtctgata aaacagaatt tgcctggcgg cagtagcgcg gtggtcccac ctgaccccat     120
gccgaactca gaagtgaaac gccgtagcgc cgatggtagt gtggggtctc cccatgcgag     180
agtagggaac tgccaggcat caaataaaac gaaaggctca gtcgaaagac tgggcctttc     240
gttttatctg ttgtttgtcg gtgaacgctc tcctgagtag acaaatccgc cgggagcgg     300
atttgaacgt tgcgaagcaa cggccccggag ggtggcgggc aggacgcccg ccataaactg     360
ccaggcatca aattaagcag aaggccatcc tgacggatgg ccttttttgcg tttctacaaa     420
ctctt                                                                425
```

<210> SEQ ID NO 21
<211> LENGTH: 31
<212> TYPE: DNA
<213> ORGANISM: Artificial sequence
<220> FEATURE:
<223> OTHER INFORMATION: PCR primer

<400> SEQUENCE: 21

```
ctctgtcgac ccgaagatct gaagattcct g                                     31
```

<210> SEQ ID NO 22
<211> LENGTH: 46
<212> TYPE: DNA
<213> ORGANISM: Artificial sequence
<220> FEATURE:
<223> OTHER INFORMATION: PCR primer

<400> SEQUENCE: 22

```
ctctgtcgac ggatccccat ggtgtgtctc ctctaaagat tgtagg                     46
```

<210> SEQ ID NO 23
<211> LENGTH: 36
<212> TYPE: DNA
<213> ORGANISM: Artificial Sequence

```
<220> FEATURE:
<223> OTHER INFORMATION: PCR primer

<400> SEQUENCE: 23
ctctgcatgc ccatggctgt tttggcggat gagaga                               36

<210> SEQ ID NO 24
<211> LENGTH: 41
<212> TYPE: DNA
<213> ORGANISM: Artificial sequence
<220> FEATURE:
<223> OTHER INFORMATION: PCR primer

<400> SEQUENCE: 24
ctctgcatgc tcatgaaaga gtttgtagaa acgcaaaaag g                         41

<210> SEQ ID NO 25
<211> LENGTH: 5118
<212> TYPE: DNA
<213> ORGANISM: Unknown
<220> FEATURE:
<223> OTHER INFORMATION: pCRB207

<400> SEQUENCE: 25
agatctaggt ttcccgactg gaaagcgggc agtgagcgca acgcaattaa tgtgagttag      60
ctcactcatt aggcacccca ggctttacac tttatgcttc cggctcgtat gttgtgtgga     120
attgtgagcg gataacaatt tcacacagga aacagctatg accatgatta cgaattcgag     180
ctcggtaccc ggggatcctc tagagtcgac ccgaagatct gaagattcct gatacaaatt     240
ctgttgtgac ggaagatttg ttggaagaaa tctagtcgct cgtctcataa aaacgaccga     300
gcctattggg attaccattg aagccagtgt gagttgcatc acactggctt caaatctgag     360
actttacttt gtggattcac gggggtgtag tgcaattcat aattagcccc attcggggga     420
gcagatcgcg gcgcgaacga tttcaggttc gttccctgca aaaactattt agcgcaagtg     480
ttggaaatgc cccgtctggg gtcaatgtc tattttgaa tgtgtttgta tgattttgaa      540
tccgctgcaa aatctttgtt tccccgctaa agttggggac aggttgacac ggagttgact     600
cgacgaatta tccaatgtga gtaggtttgg tgcgtgagtt ggaaaatttc gccatactcg     660
cccttgggtt ctgtcagctc aagaattctt gagtgaccga tgctctgatt gacctaactg     720
cttgacacat tgcatttcct acaatcttta gaggagacac accatggctg ttttggcgga     780
tgagagaaga ttttcagcct gatacagatt aaatcagaac gcagaagcgg tctgataaaa     840
cagaatttgc ctggcggcag tagcgcggtg gtcccacctg accccatgcc gaactcagaa     900
gtgaaacgcc gtagcgccga tggtagtgtg gggtctcccc atgcgagagt agggaactgc     960
caggcatcaa ataaaacgaa aggctcagtc gaaagactgg gcctttcgtt ttatctgttg    1020
tttgtcggtg aacgctctcc tgagtaggac aaatccgccg ggagcggatt tgaacgttgc    1080
gaagcaacgg cccggagggt ggcgggcagg acgcccgcca taaactgcca ggcatcaaat    1140
taagcagaag gccatcctga cggatggcct ttttgcgttt ctacaaactc tttcatgggg    1200
atccgtcgac ctgcaggcat gcaagcttgg cactggccgt cgttttacaa cgtcgtgact    1260
gggaaaaccc tggcgttacc caacttaatc gccttgcagc acatccccct ttcgccagct    1320
ggcgtaatag cgaagaggcc cgcaccgatc gcccttccca acagttgcgc agcctgaatg    1380
gcgaatgcga tttattcaac aaagccgccg tcccgtcaag tcagcgtaat gctctgccag    1440
tgttacaacc aattaaccaa ttctgattag aaaaactcat cgagcatcaa atgaaactgc    1500
```

```
aatttattca tatcaggatt atcaatacca tatttttgaa aaagccgttt ctgtaatgaa    1560
ggagaaaact caccgaggca gttccatagg atggcaagat cctggtatcg gtctgcgatt    1620
ccgactcgtc caacatcaat acaacctatt aatttcccct cgtcaaaaat aaggttatca    1680
agtgagaaat caccatgagt gacgactgaa tccggtgaga atggcaaaag cttatgcatt    1740
tctttccaga cttgttcaac aggccagcca ttacgctcgt catcaaaatc actcgcatca    1800
accaaaccgt tattcattcg tgattgcgcc tgagcgagac gaaatacgcg atcgctgtta    1860
aaaggacaat tacaaacagg aatcgaatgc aaccggcgca ggaacactgc cagcgcatca    1920
acaatatttt cacctgaatc aggatattct tctaatacct ggaatgctgt tttcccgggg    1980
atcgcagtgg tgagtaacca tgcatcatca ggagtacgga taaaatgctt gatggtcgga    2040
agaggcataa attccgtcag ccagtttagt ctgaccatct catctgtaac atcattggca    2100
acgctacctt tgccatgttt cagaaacaac tctggcgcat cgggcttccc atacaatcga    2160
tagattgtcg cacctgattg cccgacatta tcgcgagccc atttataccc atataaatca    2220
gcatccatgt tggaatttaa tcgcggcttc gagcaagacg tttcccgttg aatatggctc    2280
ataacacccc ttgtattact gtttatgtaa gcagacagtt ttattgttca tgatgatata    2340
tttttatctt gtgcaatgta acatcagaga ttttgagaca caacgtggct tgttgaata    2400 aatcgaactt tgctgagtt gaaggatcag atcacgcatc ttcccgacaa cgcagaccgt    2460
tccgtggcaa agcaaaagtt caaaatcacc aactggtcca cctacaacaa agctctcatc    2520
aaccgtggct ccctcacttt ctggctggat gatggggcga ttcaggcctg gtatgagtca    2580
gcaacacctt cttcacgagg cagacctctc gacggagttc cactgagcgt cagacccgt    2640 agaaaagatc aaaggatctt cttgagatcc ttttttttctg cgcgtaatct gctgcttgca    2700
aacaaaaaaa ccaccgctac cagcggtggt ttgtttgccg gatcaagagc taccaactct    2760
ttttccgaag gtaactggct tcagcagagc gcagatacca aatactgttc ttctagtgta    2820
gccgtagtta ggccaccact tcaagaactc tgtagcaccg cctacatacc tcgctctgct    2880
aatcctgtta ccagtggctg ctgccagtgg cgataagtcg tgtcttaccg ggttggactc    2940
aagacgatag ttaccggata aggcgcagcg gtcgggctga acggggggtt cgtgcacaca    3000
gcccagcttg gagcgaacga cctacaccga actgagatac ctacagcgtg agctatgaga    3060
aagcgccacg cttcccgaag ggagaaaggc ggacaggtat ccggtaagcg cagggtcgg    3120 aacaggagag cgcacgaggg agcttccagg gggaaacgcc tggtatcttt atagtcctgt    3180
cgggtttcgc cacctctgac ttgagcgtcg attttgtga tgctcgtcag gggggcggag    3240
cctatggaaa aacgccagca acgcggcctt tttacggttc ctggccttt gctggccttt    3300 tgctcacatg ttctttcctg cgttatcccc tgattctgtg ataaccgta ttaccgcctt    3360 tgagtgagct gataccgctc gccgcagccg aacgaccgag cgcagcgagt cagtgagcga    3420
ggaagcggaa gaagctcgca cattcagcag cgttttcag cgcgttttcg atcaacgttt    3480
caatgttggt atcaacacca ggtttaactt tgaacttatc ggcactgacg gttactgatt    3540
ttgaactttt gctttgccac ggaacggtct gcgttgtcgg gaagatgcgt gatctgatcc    3600
ttcaactcag caaaagttcg ccaatacgca aaccgcctct ccccgcgcgt tggccgattc    3660
attaatgcag ctggcacgag atctgacttg gttacgatgg actttgaaca cgccgaggt    3720 gactaaaccg ctggatttac gcggttttct tctcttcaac ttctttgacg tagcggtgaa    3780
ccgtgcccac cgagcaacca atctctgccg cgatagcgcg catggacaga cctttggcgc    3840
gcagctcctg gacgcgagca cgcttctcgt tggcacgttt aatgaacact tcacgcggtt    3900
```

```
cggaagtcca tcgttgagct gttctcaccg acataccggc acgttctgcc agctcgcggg    3960 ctgttttttcc gttgcgtgga taacgtgcat aaaccttagc caatgttcct ccaaagagta    4020
tgtccagcct cacgacgcac ctcagcgctt cgttgccagc cttcttccc gcgtgcggat      4080 tgcattgcgg tgaatgtggc gtcgtagacg gcggcgccgt ctgtccacat gcgtgacttg    4140
gtgatgatcc atttatggat tgacctggca atacagtcaa cttcggccac aggtagtggt    4200
tcatcaaaca gctcttggtt aagtgcttgc gcggtggttt ggattgcgcg gcctaggccg    4260
tcagcgtctc caaaatgctt tctgacctcc cgatatgccc acgtacgtgc gctttcaaag    4320
agtgcgcaat tacgacctag accaactggc gagaaccgcc gcgttttcct ccaggacgca    4380
ggcggcataa agccggtttc ttcgagccaa agcgcagct catcgagcgt atacagctta     4440
tcggtgatcc agtgactatc ccatgcagtg tgctcgggg ttttggtgat cagcccggag     4500
tatccgctat cgccatcgac agagcgccgt aggccttcgg tgacagccgc ggcataggcc    4560
aaaggcttgc gtttggcgta ttcggtgcgg gtaaatggct ccgcgagcgc ccagacagcg    4620
tgtgcgtgcc cgtttaaggg gttttcaacc accgcgttag gtctccagtc ctccctgtcc    4680
cacaaagagc gcaaaagcgc gtcctcctgg tcgatgtcaa cgaccaggag ttagagagc     4740 gcgtcgggat tggcttcgac gtagcgctta tccagcgcgt tcttccgtga ggtgcggtaa    4800
atgccctcac ggaggtcatc gcttgccaat ggccacagcg gcagccacag ctgctcaaag    4860
cgtccctcag ggcgggtagt tggtctcatg tagctgactt tctcacacga gcgtgcacgg    4920
tcggttttca ttcataatac gacatttaac caagtcagat gttttcccgg tttccggggg    4980
ttcccctgaa gaaccttcc agtgcgagcg aagcgagctc ctttggccgg cgcccctcag    5040
gtagccctct aaggctccca gggctccgcc cctccctgag gttggctcaa gcctcctggt    5100
ggctcctacg gacgttct                                                  5118

<210> SEQ ID NO 26
<211> LENGTH: 29
<212> TYPE: DNA
<213> ORGANISM: Artificial sequence
<220> FEATURE:
<223> OTHER INFORMATION: PCR primer

<400> SEQUENCE: 26
ctctcatatg ctgttttggc ggatgagag                                      29

<210> SEQ ID NO 27
<211> LENGTH: 33
<212> TYPE: DNA
<213> ORGANISM: Artificial sequence
<220> FEATURE:
<223> OTHER INFORMATION: PCR primer

<400> SEQUENCE: 27
ctctcatatg gtgtctcctc taaagattgt agg                                 33

<210> SEQ ID NO 28
<211> LENGTH: 1401
<212> TYPE: DNA
<213> ORGANISM: Corynebacterium glutamicum

<400> SEQUENCE: 28
atgaataggg gtgtgagttg gacagttgat atccctaaag aagttctccc tgatttgcca    60
ccattgccag aaggcatgca gcagcagttc gaggacacca tttcccgtga cgctaagcag   120
```

```
caacctacgt gggatcgtgc acaggcagaa acgtgcgca agatccttga gtcggttcct       180
ccaatcgttg ttgccectga ggtacttgag ctgaagcaga agcttgctga tgttgctaac       240
ggtaaggcct tcctcttgca gggtggtgac tgtgcggaaa ctttcgagtc aaacaccgag       300
ccgcacattc gcgccaacgt aaagactctg ctgcagatgg cagttgtttt gacctacggt       360
gcatccactc ccgtgatcaa gatggctcgt attgctggtc agtacgcaaa gcctcgctct       420
tctgatttgg atggaaatgg tctgccaaac taccgtggcg atatcgtcaa cggtgtggag       480 gcaaccctg aggctcgtcg ccacgatcct gccgcatga tccgtgctta cgctaacgct        540
tctgctgcga tgaacttggt gcgcgcgctc accagctctg gcaccgctga tctttaccgt       600
ctcagcgagt ggaaccgcga gttcgttgcg aactccccag ctggtgcacg ctacgaggct       660
cttgctcgtg agatcgactc cggtctgcgc ttcatggaag catgtggcgt gtccgatgag       720
tccctgcgcg ctgcagatat ttactgctcc cacgaggcac ttctcgtgga ttacgagcgc       780
tccatgctgc gtcttgcaac cgatgaggaa ggcaacgagg aactttacga tctttcagct       840
caccagctgt ggatcggcga gcgcaccgc ggtatggatg atttccatgt gaacttcgca        900
tccatgatct ctaacccaat cggcatcaag attggtcctg gtatcacccc tgaagaggct       960
gttgcatacg ctgacaagct cgatccgaac ttcgagcctg gccgtttgac catcgttgct      1020
cgcatgggcc acgacaaggt tcgctccgta cttcctggtg ttatccaggc tgttgaggca      1080
tccggacaca aggttatttg gcagtccgat ccgatgcacg gcaataccct caccgcatcc      1140
aatggctaca agaccgtca cttcgacaag gttatcgatg aggtccaggg cttcttcgag       1200
gtccaccgcg cattgggcac ccacccaggc ggaatccaca ttgagttcac tggtgaagat      1260
gtcaccgagt gcctcggtgg cgctgaagac atcaccgatg ttgatctgcc aggccgctac      1320
gagtccgcat gcgatcctcg cctgaacact cagcagtctt tggagttggc tttcctcgtt      1380
gcagaaatgc tgcgtaatta a                                                1401

<210> SEQ ID NO 29
<211> LENGTH: 28
<212> TYPE: DNA
<213> ORGANISM: Artificial sequence
<220> FEATURE:
<223> OTHER INFORMATION: PCR primer

<400> SEQUENCE: 29
ctctcatatg aatagggtg tgagttgg                                           28

<210> SEQ ID NO 30
<211> LENGTH: 35
<212> TYPE: DNA
<213> ORGANISM: Artificial sequence
<220> FEATURE:
<223> OTHER INFORMATION: PCR primer

<400> SEQUENCE: 30
ctctcatatg ttaattacgc agcatttctg caacg                                  35

<210> SEQ ID NO 31
<211> LENGTH: 498
<212> TYPE: DNA
<213> ORGANISM: Escherichia coli

<400> SEQUENCE: 31
atgtcacacc ccgcgttaac gcaactgcgt gcgctgcgct attgtaaaga gatccctgcc        60
ctggatccgc aactgctcga ctggctgttg ctggaggatt ccatgacaaa acgttttgaa       120
```

```
cagcagggaa aaacggtaag cgtgacgatg atccgcgaag ggtttgtcga gcagaatgaa    180
atccccgaag aactgccgct gctgccgaaa gagtctcgtt actggttacg tgaaattttg    240
ttatgtgccg atggtgaacc gtggcttgcc ggtcgtaccg tcgttcctgt gtcaacgtta    300
agcgggccgg agctggcgtt acaaaaattg gtaaaacgc cgttaggacg ctatctgttc     360
acatcatcga cattaacccg ggactttatt gagataggcc gtgatgccgg gctgtggggg    420
cgacgttccc gcctgcgatt aagcggtaaa ccgctgttgc taacagaact gttttaccg     480 gcgtcaccgt tgtactaa                                                  498
```

```
<210> SEQ ID NO 32
<211> LENGTH: 26
<212> TYPE: DNA
<213> ORGANISM: Artificial sequence
<220> FEATURE:
<223> OTHER INFORMATION: PCR primer

<400> SEQUENCE: 32
ctctcatatg tcacaccccg cgttaa                                          26
```

```
<210> SEQ ID NO 33
<211> LENGTH: 29
<212> TYPE: DNA
<213> ORGANISM: Artificial sequence
<220> FEATURE:
<223> OTHER INFORMATION: PCR primer

<400> SEQUENCE: 33
ctctcatatg ttagtacaac ggtgacgcc                                       29
```

```
<210> SEQ ID NO 34
<211> LENGTH: 558
<212> TYPE: DNA
<213> ORGANISM: Pseudomonas putida

<400> SEQUENCE: 34
gtgtcgtacg aatccccgca agcagccgct gtcgcgtggc tgccgtattc acagctggcg     60
accgacatcg accagcccac ccttgactgg ctgttcgacg agggctcgct gacccgccgc    120
ctgacccgtc tgtccattga tcactttttcc gtcaccccgt tgttcgaggg ctggcagccg    180
ctgcgcgatg acgaatgcca ggcgctgggc atcgctgccg gcgccgaagg ctgggtgcgc    240
gaagtgtatc tgcgcggcca tggccaacct tgggtattcg cccgcagcgt ggccagccgc    300
agcgccctgg aacgtggtgg cctggacctg gaaaccttgg gcagccgctc gctgggcgag    360
ctgctgttct gcgaccaggc gttcatccgt catccactcg aagtgtgcac ttatccacag    420
gcctggctgc cgtccgaagc tgcacatgcg gcgctttggg gccgccgctc gcgcttcgag    480
cgcaacggcc tggacctgct ggtggcagaa gtgttcctgc cggcattgtg gcaagcggcc    540
aaggaggaaa accgctga                                                  558
```

```
<210> SEQ ID NO 35
<211> LENGTH: 25
<212> TYPE: DNA
<213> ORGANISM: Artificial sequence
<220> FEATURE:
<223> OTHER INFORMATION: PCR primer

<400> SEQUENCE: 35
ctctcatatg tcgtacgaat ccccg                                           25
```

<210> SEQ ID NO 36
<211> LENGTH: 29
<212> TYPE: DNA
<213> ORGANISM: Artificial sequence
<220> FEATURE:
<223> OTHER INFORMATION: PCR primer

<400> SEQUENCE: 36

```
ctctcatatg tcagcggttt tcctccttg                                     29
```

<210> SEQ ID NO 37
<211> LENGTH: 2285
<212> TYPE: DNA
<213> ORGANISM: Bacillus subtilis

<400> SEQUENCE: 37

```
atgaaagcag aattcaagcg taaaggaggg ggcaaagtga aactcgttgt cggaatgaca      60
ggggcaacag gggccatttt cggggtcagg ctgctgcagt ggctgaaggc cgccggagtg     120
gaaacccatc tcgttgtgtc tccttgggca acgtcacga tcaaacacga aacaggctat     180
acgttacaag aagtagaaca actggccaca tacacttact cacataagga tcaggcggca     240
gccatttcaa gcgggtcgtt tgataccgat ggaatgattg ttgcgccgtg cagcatgaaa     300
tctctcgcaa gcattcgcac aggaatggcg gataatctgc tgacacgtgc ggcggatgtc     360
atgctcaagg agagaaaaaa actcgtcctc ttaacgagag acgcctttt gaaccaaatt     420
catctcgaaa atatgctagc gcttacgaaa tgggcacca tcattcttcc tccgatgccg     480
gcatttata atcggccgag aagcttagag gaaatggttg accatattgt ttttagaacg     540
ttggaccaat tcggcattcg gcttcctgaa gcgaagcgct ggaatgggat tgaaaaacaa     600
aaaggaggag cttgatcatg gcttatcaag atttcagaga atttctcgct gcccttgaaa     660
aagaaggaca gctgcttaca gtgaatgaag aggtaaagcc ggaaccggat ttaggggcct     720
ccgcacgggc agccagcaat cttggcgata aagcccctgc gctcttattt aacaacattt     780
acggctatca taacgcgcga attgcgatga atgtcatcgg ctcttggcca aaccatgcca     840
tgatgctggg catgccgaaa gacacaccgg taaaagaaca gttttttgaa ttcgcaaagc     900
gttatgacca gtttccgatg ccggtcaaac gtgaggaaac agcgccattt catgaaaatg     960
aaatcacaga agatatcaat ttgttcgata tactgcctct tttcagaatt aaccaggtg    1020
atggaggcta ctatttagac aaagcatgtg tcatttcccg tgatcttgag daccctgaca    1080
acttcggcaa acaaaatgtc ggcatttaca gaatgcaagt caaaggaaaa gaccgccttg    1140
gcattcagcc tgtcccgcag cacgatattg caatccatct gcgccaagct gaagaacgcg    1200
gcatcaacct tccggtcact attgcgctcg gctgtgagcc ggtcattaca acggcggcat    1260
cgactccgct tctctatgat caatcagaat acgaaatggc aggtgcgatt caaggcgaac    1320
catatcgcat cgtcaaatca agctgtctg atcttgatgt tccgtggggc gctgaagtgg    1380
tgcttgaagg tgagattatt gccggagagc gcgaaatga agggccgttc ggtgaattca    1440
caggccatta ttccggcgga cgcagcatgc cgattatcaa aattaaacgc gtctatcaca    1500
gaaacaatcc gatctttgaa catttatact taggcatgcc ttggacagaa tgcgattaca    1560
tgatcggcat taacacatgc gtgccgcttt atcagcagtt aaaagaagcg tatccgaacg    1620
aaattgtggc agtgaacgcc atgtacacac acggtttaat cgcgattgtt ccacaaaaaa    1680
cccgctatgg cggatttgcg aaagcggtcg gcatgcgcgc actcacaacg ccgcacggac    1740
tcggctactg caaaatggtc atagtcgttg atgaggatgt cgatccattc aaccttccgc    1800
```

```
aggtcatgtg ggcgctttcg accaaaatgc atccgaaaca tgatgcggtc atcattccgg    1860
acttatctgt cctgccgctt gatccgggat ccaatccatc aggaatcact cacaaaatga    1920
ttctcgacgc cactacaccg gttgcgccgg aaacaagagg ccattattca cagccgcttg    1980
attctccgct aacaacgaaa gaatgggaac aaaaactaat ggacttaatg aataaataag    2040
gaaaggatgt tcgaaatgca tacatgtcct cgatgcgact caaaaaaggg agaagtcatg    2100
agcaaatcgc ctgtagaagg cgcatgggaa gtttatcagt gccaaacatg ctttttaca     2160 tggagatcct gtgaaccgga agcattaca aatcccgaaa aatacaatcc agcgtttaaa     2220
attgatccaa aggaaacaga aacagcaatt gaagttccgg cggtgccgga acgaaaggct    2280
tgatc                                                                 2285

<210> SEQ ID NO 38
<211> LENGTH: 32
<212> TYPE: DNA
<213> ORGANISM: Artificial sequence
<220> FEATURE:
<223> OTHER INFORMATION: PCR primer

<400> SEQUENCE: 38
ctctcatatg aaagcagaat tcaagcgtaa ag                                   32

<210> SEQ ID NO 39
<211> LENGTH: 29
<212> TYPE: DNA
<213> ORGANISM: Artificial sequence
<220> FEATURE:
<223> OTHER INFORMATION: PCR primer

<400> SEQUENCE: 39
ctctcatatg gatcaagcct ttcgttccg                                       29

<210> SEQ ID NO 40
<211> LENGTH: 30
<212> TYPE: DNA
<213> ORGANISM: Artificial sequence
<220> FEATURE:
<223> OTHER INFORMATION: PCR primer

<400> SEQUENCE: 40
ctcttctaga gaaacgatca agtgcaccag                                      30

<210> SEQ ID NO 41
<211> LENGTH: 40
<212> TYPE: DNA
<213> ORGANISM: Artificial sequence
<220> FEATURE:
<223> OTHER INFORMATION: PCR primer

<400> SEQUENCE: 41
gacacgagcg tttatacctc taattgccac tggtacgtgg                           40

<210> SEQ ID NO 42
<211> LENGTH: 20
<212> TYPE: DNA
<213> ORGANISM: Artificial sequence
<220> FEATURE:
<223> OTHER INFORMATION: PCR primer

<400> SEQUENCE: 42
gaggtataaa cgctcgtgtc                                                 20
```

<210> SEQ ID NO 43
<211> LENGTH: 30
<212> TYPE: DNA
<213> ORGANISM: Artificial sequence
<220> FEATURE:
<223> OTHER INFORMATION: PCR primer

<400> SEQUENCE: 43

```
ctctgagctc gagaacacga accatacgag                                    30
```

<210> SEQ ID NO 44
<211> LENGTH: 2249
<212> TYPE: DNA
<213> ORGANISM: Bacillus atrophaeus

<400> SEQUENCE: 44

```
atgaaactcg ttgtcgggat gaccggagct acaggggcta ttttcggagt caggcttttta    60
gaatggctga aggccgcagg agcggaaact caccttgtcg tttctccttg ggctcatgtc    120
acaatcaaac atgaaacagg ttatagctta aagaagttg aagagcttgc ctcatatacg    180
tactctcata aggatcaggc ggctgccatt tcaagcgggt cttttcaaac ggacggcatg    240
atcgtcgccc cgtgcagtat gaagtcgctc gcaagcattc gcacggggat ggcggacaat    300
ctgctgaccc gggctgcaga tgtcatgctg aaagagagaa aaaagcttgt cctgctgacg    360
agagaaacgc cgcttaacca gattcattta gagaatatgc tcgcattaac aaagatggga    420
accattattc ttccgccaat gccggctttt tataatcagc cggcaagtct ggatgaaatg    480
gtggaccata ttgtattcag aacgctggat caattcggca ttcgccttcc tgaggcaaaa    540
cgctggaatg gaattgaaaa agaaaaagga ggagcttgat catggcttat caagatttca    600
gagaatttct cgctgccctg aaaaagagg acagctatt aaaagtggat gaagaggtga    660
agccggagcc ggatttagga gccgcagccc gcgcagccaa caacctcggt gataaaagcc    720
cggctctttt atttaacaat atttacggct acaacaatgc acaaatcgcg atgaatgtca    780
tcggttcttg gccgaaccac gcgatgatgc ttggcttgcc gaaagataca ccggttaaag    840
agcagttttt tgaatttgcg aagcgatatg aacagttttcc gatgccggtc aaacgcgaag    900
aaactgcgcc atttcatgaa atgaaatca cagaggacat caacctattc gatatattgc    960
ctctttttcag aattaaccag ggtgacgcg gctattattt agataaagcg tgtgtcattt    1020
cccgtgatct ggatgaccct gacaacttcg gcaagcagaa cgtcggaatt taccgcatgc    1080
aggtaaaagg gaaagaccgc ctcggcattc agccagttcc gcagcatgac atcgcgattc    1140
atcttcgcca agcagaagaa cgcggcatca atcttccggt caccatcgcg cttggctgtg    1200
agcctgtcat tacgaccgcg gcgtcaactc cgctcctata tgaccaatcg gaatatgaaa    1260
tggcgggagc gatccagggc gaaccgtata gaatcgtcaa atcaaagctg tctgaccttg    1320
atattccttg gggcgcagaa gtcgtgcttg aaggagaaat cattgccgga gaacgggaat    1380
atgaaggacc gttcggcgaa tttaccggcc attattcagg cggacgcagc atgccgatta    1440
tcaaaatcaa acgcgtatct catagaaatc atccggtatt gaacattta tatctcggca    1500
tgccttggac agagtgcgat tacatgatcg gcattaatac atgcgtgccg ctttatcagc    1560
agctgaaaga agcatatccg agtgaaattg tcgctgtgaa cgcaatgtac acacatggct    1620
taatcgccat tgtatctaca aaaacccgtt acggaggatt tgcaaaagct gtcggaatga    1680
gagccctgac tacaccgcac ggactcggct actgtaagat ggtgatcgtc gtggatgaag    1740
atgttgatcc gttcaaccctc ccgcaagtca tgtgggcgct ttcaacaaag atgcatccga    1800
```

| agcatgatgt cgtaactatt cctgatttat ccgtgctgcc gcttgatccg ggatcagacc | 1860 |
| catccggcat tactcataaa atgattctcg atgccacaac gcctgttgcg ccggaaacaa | 1920 |
| gaggccatta ttcacagccg cttgactctc ctttaacaac aaaagaatgg gaacaaaaac | 1980 |
| taatggactt gatgaataaa taagagaaag gatgatccga catgcataca tgtcctcgat | 2040 |
| gtgattcaaa aaagggagaa atcatgagca atcgcctgt agaaggcgct tgggaagtct | 2100 |
| accaatgcca acatgtttc ttcacatgga gatcatgtga accggaaagc attacaaacc | 2160 |
| cgaaacaata caatccatca tttaagatcg atccgaagga aacagaaaca gctgttgaag | 2220 |
| tgccggctgt tccggaaaga aaggcctga | 2249 |

<210> SEQ ID NO 45
<211> LENGTH: 28
<212> TYPE: DNA
<213> ORGANISM: Artificial sequence
<220> FEATURE:
<223> OTHER INFORMATION: PCR primer

<400> SEQUENCE: 45

| ctctcatatg aaactcgttg tcgggatg | 28 |

<210> SEQ ID NO 46
<211> LENGTH: 26
<212> TYPE: DNA
<213> ORGANISM: Artificial sequence
<220> FEATURE:
<223> OTHER INFORMATION: PCR primer

<400> SEQUENCE: 46

| ctctcatatg tcaggccttt ctttcc | 26 |

<210> SEQ ID NO 47
<211> LENGTH: 2283
<212> TYPE: DNA
<213> ORGANISM: Bacillus subtilis subsp.spizizenii

<400> SEQUENCE: 47

| atgaaagcag aattcaagcg taaaggaggg ggcaaagtga aactcgttgt cgggaatgaca | 60 |
| ggggcaacag gggctatttt cggggtcagg ctgctggagt ggctgaaggc ggccgaagta | 120 |
| gaaacccatc tcgtcgtgtc tccttgggct aacgtcacga tcaaacacga aacaggctat | 180 |
| accttaaaag aagtagaaca acttgccaca tacacgtatt cgcataagga ccaggcggca | 240 |
| gccatttcaa gcgggtcgtt tgataccgat ggcatgattg ttgcgccatg cagcatgaaa | 300 |
| tctctcgcaa gcattcgcac cgggatggcg gataatctgc tgacgcgtgc ggcggatgtc | 360 |
| atgctcaagg agagaaaaaa actcgtcctc ttaacgagag agacgccttt gaaccagatt | 420 |
| catctcgaaa atatgctagc gcttacgaaa atgggtacca tcattcttcc tccgatgccg | 480 |
| gcatttttata atcagccgag cagcttagag gaaatggttg accatattgt attcagaacg | 540 |
| ttggaccaat tcggcattcg ccttcctgaa gcgaaacgct ggaatgggat tgaaaaacaa | 600 |
| aaaggaggag cttgatcatg gcttatcaag atttcagaga atttctcgct gcccttgaaa | 660 |
| aagaaggaca gctgctaaca gtgaatgaag aggtaaagcc ggagccggat ataggggctg | 720 |
| cagcacgcgc agccagcaat cttggcgata aaagccccgc gctcttattt aataacattt | 780 |
| atggctatca caacgcgcaa attgcgatga atgtgatcgg ctcctggccg aaccatgcaa | 840 |
| tgatgctggg catgccgaaa gacacgccgg tgaaagaaca gttttttgaa tttgcgaaac | 900 |

```
gttatgacca gtttccgatg ccagtcaaac gtgaggaatc agcgccgttt catgaaaatg      960
aaatcacaga agatatcaat ttgttcgata tactgcctct tttcagaatt aaccaaggag     1020
acggcggtta ctatctagac aaagcatgtg tcatttcccg cgatcttgaa gatcctgaga     1080
atttcggcaa acaaaacgtc gggatttaca gaatgcaggt caaggaaaaa gaccgccttg     1140
gcattcagcc tgtgccgcag cacgatattg cgatccatct gcgtcaagct gaagaacgcg     1200
gcatcaatct tccggtcacc attgcgctcg gctgtgagcc ggtcataaca acggcggcat     1260
cgactccgct tctttatgat caatcagaat acgaaatggc aggcgcaatt caaggtgaac     1320
catatcgcat cgtgaaatct aagctgtctg atcttgatgt tccatggggc gctgaagtag     1380
tgcttgaagg tgaaatcatt gccggagagc gtgaatatga aggcccgttc ggtgagttca     1440
caggccatta ttccggcgga cgcagcatgc cgattattaa aattaaacga gtgtatcata     1500
gaaacaatcc gattttttgaa catttatact taggcatgcc ttggacagaa tgcgattaca     1560
tgattggcat taaacacttgt gtgccgcttt atcagcagtt aaaagaagcg tatccgaatg     1620
aaattgtggc tgtgaacgcc atgtacacac acggtttgat cgcgattgtt ccacaaaaaa     1680
cacgctatgg cggatttgcg aaagcagtcg gcatgcgcgc gctcacaaca ccgcacggac     1740
tcggctactg caaaatggtc attgtcgttg acgaggatgt cgatccattc aatctgccgc     1800
aggtcatgtg ggcgctttcg accaaaatgc atccgaagca cgatgcggtc atcattccag     1860
acttatctgt cctgccgctt gacccgggat ctaatccatc aggaatcact cacaaaatga     1920
ttcttgacgc cactacaccg gttgcgccgg aaacaagagg ccattattca cagccgcttg     1980
attcaccatt aacaacgaaa gaatgggaac aaaaactaat ggacttaatg aataaataag     2040
aaaaggatga tcgaaatgca tatatgtcct cgttgcgatt cgaaaagggg agaagtcatg     2100
agcaaatcgc ctgtagaagg cgcatgggaa gtttatcagt gtcaaacatg ttttttcaca     2160
tggagatcct gtgagccgga aagtattaca aatccggcga aatacaatcc agcgtttaaa     2220
attgatccga aggaaacaga aacagcaatt gaagttccgg ctgtgccgga acgaaaggct     2280
tga                                                                   2283
```

<210> SEQ ID NO 48
<211> LENGTH: 32
<212> TYPE: DNA
<213> ORGANISM: Artificial sequence
<220> FEATURE:
<223> OTHER INFORMATION: PCR primer

<400> SEQUENCE: 48
ctctcatatg aaagcagaat tcaagcgtaa ag                                     32

<210> SEQ ID NO 49
<211> LENGTH: 28
<212> TYPE: DNA
<213> ORGANISM: Artificial sequence
<220> FEATURE:
<223> OTHER INFORMATION: PCR primer

<400> SEQUENCE: 49
ctctcatatg tcaagccttt cgttccgg                                          28

<210> SEQ ID NO 50
<211> LENGTH: 2268
<212> TYPE: DNA
<213> ORGANISM: Citrobacter koseri

<400> SEQUENCE: 50

-continued

```
atgagactga ttgtggggat gaccggcgca acggggcgc cgctaggcat tgcgctgcta      60
caggcgctgc ggcaaatgcc gacagtagaa acacacctgg taatgtctaa gtgggccaaa    120
acgaccattg agctggaaac gccttacagt gcgcgagatg ttgccggact ggctgattac    180
tgccataacc cggcggatca ggcggcgacg atctcttccg gctcatttcg caccgacggc    240
atgatcatta tgccttgcag tatgaaaacg ctggcgggga ttcgcgcagg atatgccgag    300
gggttagttg ccgtgccgc cgatgtggtg ctgaaagaag ggcgcaaact ggtgctggtg     360
ccgcgtgaaa tgccgctcag cacgatccat ctggaaaaca tgctcgccct ttcccgcatg    420
ggggtcgcga tggtgccgcc catgcctgct ttctacaacc atccgcaaac tattgatgat    480
attacgcagc atattgtggc gcgtgtgctg gatcagtttg gtctggagca tccgcgtgcc    540
cggcgctggg aggggttgca gcaggcgcag aatttttcac aggagaatga ataatggcat    600
ttgatgactt acgcagcttt tgcaggcgc tcgacgagca ggggcaactg ctgaaaatca     660
gtgaagaagt gaatgcagag ccggatctgg ctgctgcggc taacgcaacc gggcgcattg    720
gcgacggcgc gcctgcgctg tggttcgata atatccgtgg cttcacggat gcgcgcgtgg    780
cgatgaacac cattggttcc tggcagaacc atgccatctc tttaggcttg ccgcctaatg    840
cgccagtaaa aaagcaaatt gatgaattta ccgccgctg gacacgttc cccgtcgccc      900
ccgagcgccg agccaacccg gcgtgggcgg aaaacaccgt tgatggcgag cgatcaacc     960
tgtttgatat tctgccgctg tttcgcctca acgatggcga tggcggcttc tatctggata   1020
aagcctgtgt cgtctcccgc gatccgctcg acccggatca cttcggcaag cagaatgtgg   1080
gtatctaccg gatggaagtg aaaggcaagc gcaagctggg cctgcaaccg gtgccaatgc   1140
acgatatcgc gctgcatctg cataaggcgg aagagcgtgg cgaagatctg ccgattgcta   1200
ttacgctcgg taacgatccg atcatcactc tgatgggcgc cacgccgctg aaatacgatc   1260
agtctgagta tgaaatggcg ggcgcgctgc gcgaaagccc ataccgatc gccaccgcgc    1320
cgctgaccgg ctttgatgtg ccgtggggtt cagaagtgat ccttgaaggg gtgatcgaaa   1380
gccgtaagcg tgaaattgaa gggccgtttg gcgagtttac cggccactat tctggtgggc   1440
gcaatatgac ggtggtgcgc atcgacaaag tgtcttatcg cactaaaccg atttttgaat   1500
cactctatct ggggatgccg tggactgaaa tcgactacct gatggggcca gcgacctgtg   1560
tgccgctgta tcagcagttg aaagcggaat tcccggaagt gcaggcggtt aacgccatgt   1620
atacccacgg tctgctggcg attatctcga ccaaaaaacg ctacggcgga tttgcccgcg   1680
cgatcggcct gcgggcaatg accacgccgc acggtctggg ctatgtgaag atggtgatta   1740
tggttgatga ggatgtcgat ccgttcaacc tgccgcaggt gatgtgggcg ctgtcgtcga   1800
aggtcaaccc ggcaggcgat ctggtgcagc tgccgaacat gtcggtgctg gaactggacc   1860
caggctcaag cccggcgggg atcactgaca aactgatcat cgacgccaca acgccggttg   1920
cgccggataa tcgcggccac tacagccagc cggtatgtga tttaccggaa accaaagcct   1980
gggctgaaaa gctgactgcc atgctggcca accgtaaata aggagtagca gatgatttgt   2040
ccacgttgtg ctgatgaaca tattgaattg atggcgacct ctccggtcaa agggatctgg   2100
acggtgtatc agtgccagca ttgtctgtac acctggcgtg ataccgagcc gctacgccgt   2160
accagccgtg aacattatcc gcaagcgttt cgcatgacgc agaaagatat tgatcaagcg   2220
ccgatggtgc cgggcattcc accgctgctg gcggaagata agcgttaa                2268
```

<210> SEQ ID NO 51

```
<211> LENGTH: 28
<212> TYPE: DNA
<213> ORGANISM: Artificial Sequence
<220> FEATURE:
<223> OTHER INFORMATION: PCR primer

<400> SEQUENCE: 51
ctctcatatg agactgattg tggggatg                                          28

<210> SEQ ID NO 52
<211> LENGTH: 31
<212> TYPE: DNA
<213> ORGANISM: Artificial sequence
<220> FEATURE:
<223> OTHER INFORMATION: PCR primer

<400> SEQUENCE: 52
ctctcatatg ttaacgctta tcttccgcca g                                      31

<210> SEQ ID NO 53
<211> LENGTH: 2268
<212> TYPE: DNA
<213> ORGANISM: Enterobacter aerogens

<400> SEQUENCE: 53
atgaaactga ttattgggat gaccggggcg accggcgcgc cgttaggcgt cgcgctgtta        60
caggcgctga tgaaatgcc ggatgtggaa acgcatctgg tcatgtcgaa atgggcaaaa        120
accaccattg agctggaaac gccctatagc gctcgtgatg tcgccgcgct ggcggacttc       180
tgccatagcc ctgcggatca ggccgcgacc atctcatcag gatcgtttcg taccgacggc       240
atgattgtta tccccctgcag catgaaaacg ctggcgggta ttcgcgctgg ctatgcggaa       300
gggttagtcg gccgcgcggc ggacgtggtg ctgaaagagg ggcgcaagct ggttctggtg       360
ccgcgtgaaa tgccgctgag caccattcat ctggagaaca tgctggcgct gtcgcgcatg       420
ggcgtggcga tggtgccgcc catgcctgcc tattacaacc acccggaaac ggtagaggat       480
atcaccaacc atatcgtgac ccgggtgctg gatcagtttg gtctcgaata tcacaaagcg       540
cgccgctgga acggcctgcg cgcggtcgag aatttatcac aggagaatta atcatggctt       600
tgatgatttt acgcagcttt ttgcaggcgc ttgatgagca ggggcaactg ctaaaaatta       660
gcgaagaggt gaatgccgag ccggatctcg ccgctgccgc taacgccaca gggcgcatcg       720
gtgacggcgc gccagcgttg tggtttgata acattcgcgg ctttaccgac gcccgtgtcg       780
ccatgaacac catcggttcc tggcaaaacc acgcgatttc gctggggctg ccgccaaaca       840
cgccggtgaa aaagcagatt gatgaattta ttcgccgctg ggataaattc ccggtaacgc       900
cggagcgtcg cgctaatcca gcgtgggcgg aaaacaccgt tgatggcgac gatatcaacc       960
tgttcgatat tctgccgctg ttccgcctga acgatggcga cggtggtttc tatctcgaca      1020
aagcctgtgt ggtttcgcgc gatccgcttg acccggacca ctttggcaaa cagaacgtcg      1080
gtatttaccg gatggaagtg aaaggcaagc gcaagctggg cctgcagccg gtaccgatgc      1140
acgatatcgc gctgcatctg cataaagcgg aagagcgcgg tgaggatctg cccattgcca      1200
tcaccctggg taacgacccg attattaccc tgatgggcgc gacgccgctg aaatatgacc      1260
agtcagaata tgagatggcg ggcgcgctgc gcgaaagccc gtatcccatc gccaccgcgc      1320
cgctgaccgg ctttgacgtt ccctggggct cagaggtgat ccttgaaggg gtgattgaag      1380 gcgcaagcg tgaaatcgaa gggccgttcg gcgagttcac cggccactac tcaggcggcc      1440
gcaatatgac ggtggtgcgt atcgataaag tctcttatcg cacaaaaccg attttttgaat      1500
```

```
cgttgtatct cggaatgccg tggaccgaaa tcgactatct gatgggcccg gcgacctgcg    1560
tgccgctgta ccagcagctg aaggcggagt tcccggaggt gcaggcggtc aatgccatgt    1620
acacccatgg tctgctggcg attatctcca ccaaaaaacg ctacggcggt tttgcccgcg    1680
cggtgggatt acgggcaatg actacccccgc acggcctcgg ttacgtgaaa atggtgatca    1740
tggtcgatga agatgtcgat ccgttcaacc tgccgcaggt gatgtgggcg ctctcctcga    1800
aggtcaaccc ggcgggcgac ctggtacagt tgccgaacat gtcggtgctg gagcttgacc    1860
ctggttccag tccggcgggg atcaccgaca aactgattat cgacgccacc accccggttg    1920
cgcctgacct tcgcggtcac tacagccagc cggttcagga tttaccggaa accaaagcct    1980
gggctgaaaa actgaccgcc atgttggcca accgtaaata aggagaagaa gatgatttgt    2040
ccacgttgcg ctgatgagca gattgaagtg atggcgacgt cgccggtaaa aggggtgtgg    2100
atcgtttacc agtgccagca ctgcctctat acctggcgta ataccgaacc gctgcgtcgt    2160
accagccgcg aacattatcc ggaagcgttc cgcatgacgc agaaagatat tgatgaggcg    2220
ccgcaggtgc cgcatattcc accgctgttg gcggcagata agcgttaa                2268
```

<210> SEQ ID NO 54
<211> LENGTH: 32
<212> TYPE: DNA
<213> ORGANISM: Artificial sequence
<220> FEATURE:
<223> OTHER INFORMATION: PCR primer

<400> SEQUENCE: 54

```
ctctcatatg aaactgatta ttgggatgac cg                                    32
```

<210> SEQ ID NO 55
<211> LENGTH: 29
<212> TYPE: DNA
<213> ORGANISM: Artificial sequence
<220> FEATURE:
<223> OTHER INFORMATION: PCR primer

<400> SEQUENCE: 55

```
ctctcatatg ttaacgctta tctgccgcc                                        29
```

<210> SEQ ID NO 56
<211> LENGTH: 2252
<212> TYPE: DNA
<213> ORGANISM: Enterobacter cloacae

<400> SEQUENCE: 56

```
atgagattga tcgtgggaat gacgggagca acaggtgctc cgctgggtgt ggctttactg     60
caggcgttac gtgacatgcc agaggttgaa acccatctgg tgatgtcgaa atgggcgaaa    120
accaccattg agctggaaac gccttatacc gcgcaggatg tcgccgccct ggcagatgtc    180
gttcacagtc ctgccgatca ggctgccacc atctcctccg gtcgtttcg taccgacggc    240
atgatcgtca ttccctgcag catgaaaacg ctggcgggta tccgcgcggg ctatgccgaa    300
gggctggtgg gccgtgcggc agacgtggtg ctgaaagagg ggcgcaagct ggtgctggtc    360
ccgcgtgaaa cgccgctcag caccattcat ctggagaaca tgctcgcgct ttcccgcatg    420
ggggtggcga tggtgccgcc catgcctgcg tattacaacc cccgcaaac cgccgatgat    480
atcacccagc atatcgtgac ccgcgtactc gaccagtttg gtctgagca caaaaaggcg    540
cgtcgctgga acggcctgca ggcggcgaaa cattttttcac aggagaataa cgatggcatt    600
```

```
tgatgatttg agaagcttcc tgcaggcgct agatgagcaa gggcaactgc tgaaaattga      660
agaagaggtc aatgcggagc cggatctggc ggcggccgct aacgcgacgg gacgtatcgg      720
tgatggtgcg cctgcgctgt ggttcgataa cattcgcggg tttaccgatg ccagggtggt      780
gatgaacacc atcggctcct ggcagaacca cgccatttcg atggggctgc ggcgaatac       840
cccggtcaaa aagcagatcg atgagtttat tcgccgctgg gataaattcc cggtcgcacc      900
ggagcgccgg gccaacccccg catgggcgca gaatacggtg gacggtgagg agattaacct     960
gttcgacatc ctgccgctgt ttcgcctgaa cgacgggac ggcggttttt atctcgacaa      1020
agcgtgcgtt gtctcgcgcg atccgctcga cccggaccat ttcggcaagc agaacgtcgg    1080
tatttaccgc atggaagtga agggcaaacg taagctcggc ctgcagccgg tgccgatgca    1140
tgatatcgcc ctgcatctgc ataaagccga agagcgtggt gaagacctgc cgattgcgat    1200
tacgttgggc aacgatccga tcatcaccct gatgggcgca acgccgctga aatacgatca    1260
gtccgagtat gaaatggccg gggcgctgcg tgaaagcccg tacccgattg cgaccgcgcc    1320
gttgaccggc ttcgatgtgc cgtggggtc tgaagtgatc ctggaagggg tgattgaagg    1380
ccgtaaacgt gaaattgaag ggccgttcgg tgagtttacc gggcactatt cgggcggacg    1440
caatatgacg gtggtccgta ttgataaagt ctcgtaccgc accaaaccga ttttcgaatc    1500
cctctatctc gggatgccct ggaccgagat cgactacctg atggggccag ccacctgtgt    1560
gccgctttac cagcaactga aagcggagtt ccctgaagtg caggcggtga acgcgatgta    1620
tacccacggt ctgctggcga tcatctccac caaaaaacgc tacggtggtt ttgcccgcgc    1680
ggtcggttta cgcgccatga ccacgccgca tggcctgggc tatgtgaaga tggtgattat    1740
ggtggatgaa gatgtcgatc cgttcaacct gccgcaggtg atgtgggcgc tgtcatcaaa    1800
agtgaacccg gcaggggatc tggtgcagct gccgaacatg tcggttcttg agcttgatcc    1860
tgggtccagc ccggcaggca tcaccgacaa gctgattatt gatgccacca cgcctgttgc    1920
gccggataac cgcggtcact acagccagcc ggtgcaggat ttacctgaaa ccaaagcctg    1980
ggctgaaaag ctgactgcga tgctggcagc acgccaataa ggaggaaaag atgatttgtc    2040
cacgttgtgc cgatgagcaa attgaggtga tggccacatc accggtgaaa gggatctgga    2100
cggtttatca gtgccagcat tgcctgtata cctggcgcga tactgagccg ctgcgtcgta    2160
ccagccgcga acattaccct gaagcgttcc gcatgacgca aaggatatt gatgaggcgc    2220
cgcaggtacc gaccattccg ccattgctgt aa                                   2252
```

<210> SEQ ID NO 57
<211> LENGTH: 30
<212> TYPE: DNA
<213> ORGANISM: Artificial sequence
<220> FEATURE:
<223> OTHER INFORMATION: PCR primer

<400> SEQUENCE: 57
ctctcatatg agattgatcg tgggaatgac                                        30

<210> SEQ ID NO 58
<211> LENGTH: 30
<212> TYPE: DNA
<213> ORGANISM: Artificial sequence
<220> FEATURE:
<223> OTHER INFORMATION: PCR primer

<400> SEQUENCE: 58
ctctcatatg ttacagcaat ggcggaatgg                                        30

<210> SEQ ID NO 59
<211> LENGTH: 2358
<212> TYPE: DNA
<213> ORGANISM: Enterobacter hormaechei

<400> SEQUENCE: 59

| | | | | | |
|---|---|---|---|---|---|
| atgagattga | ttgtgggaat | gacgggcgcg | acgggtgcgc | cattaggcgt | ggcgttgttg | 60 |
| caggcgctgc | gggaaatgcc | ggaggtggaa | acgcacctgg | tgatgacgaa | gtgggcaaaa | 120 |
| accacgattg | agctggaaac | gcccttcact | gcgcatgacg | ttgctgcact | ggcggatgtc | 180 |
| gtccacagtc | cggccgatca | ggctgccacc | atctcctccg | gctcgtttcg | caccgacggc | 240 |
| atgatcgtca | tcccgtgcag | catgaaaacg | ctggcgggga | tccgcgcggg | ctacgccgaa | 300 |
| gggctggtag | ggcgtgcggc | agacgtggtg | ctgaaagagg | gacgcaagct | ggtgctggtt | 360 |
| ccccgcgaga | cgccgctcag | caccattcat | cttgagaaca | tgcttgccct | tcccgcatg | 420 |
| ggcgtggcga | tggtgccgcc | tatgcctgcg | tactacaacc | acccgcaaac | cgccgatgac | 480 |
| attacccagc | atatcgtgac | ccgcgttctc | gaccagtttg | gtctggagca | taaaaaagcc | 540 |
| cgacgctggg | aaggtttgca | ggcagcgaaa | cattttttcac | aggagaataa | agatggcatt | 600 |
| tgatgatttg | agaagcttct | gcaggcgct | cgatgagcaa | gggcagctgc | tgaaaattga | 660 |
| ggaagaggta | aacgcggagc | cggatttagc | ggcggccgcc | aacgctaccg | ggcgcattgg | 720 |
| cgatggcgcg | cctgcgctgt | ggttcgataa | tattcgcggc | ttcaccgatg | cccgagtggt | 780 |
| gatgaacacc | atcggctcgt | ggcaaaaacca | cgccatttcg | atggggctgc | agcgaatac | 840 |
| ttcggtgaaa | aaacagatcg | acgagtttat | tcgtcgctgg | acaaattcc | ccgtcacgcc | 900 |
| agagcgtcgt | gccaatcctg | cctgggcgca | gaacacggtg | gacggagaag | atatcaacct | 960 |
| gttcgacatt | ttgccgctgt | tccgcctgaa | cgacggtgac | gggggctttt | atctcgataa | 1020 |
| agcgtgcgtt | gtctcccgcg | atccgctcga | ccccgaccac | ttcggcaagc | agaacgtcgg | 1080 |
| catttaccgt | atggaagtga | agggcaagcg | taagctcggc | ctgcaaccgg | tgccgatgca | 1140 |
| tgatattgcg | ctgcatctgc | ataaggcaga | agagcgtggc | gaagacctgc | ccattgccat | 1200 |
| tacgctgggt | aacgatccga | tcatcaccct | gatgggcgcc | acgccgctga | atacgatca | 1260 |
| atccgagtat | gagatggctg | gcgcgctacg | cgaaagcccg | tatccgattg | cgacggctcc | 1320 |
| gctgaccggt | tttgatgtgc | cgtggggtc | ggaagtgatc | ctggaagggg | tgattgaagg | 1380 |
| ccggaaacgt | gaaattgaag | gaccattcgg | tgagtttacc | ggacactact | ctggcgggcg | 1440 |
| caacatgacc | gttgtgcgca | ttgataaagt | ctcttaccgc | accaaaccca | ttttcgaatc | 1500 |
| tctctacctg | gggatgcctt | ggaccgagat | tgattatctg | atgggacccg | ccacctgcgt | 1560 |
| gccgctctat | cagcaactga | aggcggaatt | cccggaagtg | caggcggtaa | acgccatgta | 1620 |
| cacccacggt | ctgctggcaa | ttatctccac | taaaaagcgt | tacggcggtt | tgcccgtgc | 1680 |
| ggtcgggcta | cgcgccatga | ccacaccgca | cggtctgggt | tacgtgaaga | tggtgattat | 1740 |
| ggtggatgaa | gatgtcgatc | cgtttaacct | gccgcaggtc | atgtgggcgc | tttcatcgaa | 1800 |
| ggttaatccg | gcgggcgatc | tggtgcagct | tccgaatatg | tctgtgctgg | aacttgaccc | 1860 |
| tggctccagc | ccgcgcggga | tcaccgacaa | gctgatcatt | gatgccacca | cccctgttgc | 1920 |
| cccggacaac | cgtggtcact | acagccagcc | ggtacaggac | ctccctgaaa | ccaaagcctg | 1980 |
| ggccgaaaaa | ctgaccgcga | tgctggcagc | acgtcaataa | ggaggaaaaa | atgatttgtc | 2040 |
| cacgttgtgc | cgatgaacat | attgaagtaa | tggcaacatc | accggtgaaa | ggtgtctgga | 2100 |

-continued

| | | |
|---|---|---|
| cggtatatca gtgccagcac tgtctgtata cctggcgcga taccgaaccg ctacgccgta | 2160 | |
| ccagccgcga gcattacccg gaagccttcc gcatgacgca gaaggatatt gatgaggcgc | 2220 | |
| cgcaggtgcc aacaatcccg ccgctgctgt aaaaaaagcc cggtggcggc tgcgcttacc | 2280 | |
| gggcctacgg gttttgtagg ccgggtaagg cgaagccgcc acccggcaaa aaagaccgca | 2340 | |
| gagaactaaa ccagactc | 2358 | |

```
<210> SEQ ID NO 60
<211> LENGTH: 30
<212> TYPE: DNA
<213> ORGANISM: Artificial sequence
<220> FEATURE:
<223> OTHER INFORMATION: PCR primer

<400> SEQUENCE: 60
```
ctctcatatg agattgattg tgggaatgac                                30

```
<210> SEQ ID NO 61
<211> LENGTH: 31
<212> TYPE: DNA
<213> ORGANISM: Artificial sequence
<220> FEATURE:
<223> OTHER INFORMATION: PCR primer

<400> SEQUENCE: 61
```
ctctcatatg gagtctggtt tagttctctg c                              31

```
<210> SEQ ID NO 62
<211> LENGTH: 2284
<212> TYPE: DNA
<213> ORGANISM: Enterobacter sakazakii

<400> SEQUENCE: 62
```

| | |
|---|---|
| atgaggctaa ttgtcggaat gacgggcgca accggcgcgc cgcttggggt cgcgctgttg | 60 |
| caggcgctga aagcgatgcc tgaggtggaa acccatctgg tgatgtcaaa gtgggcgaaa | 120 |
| accacgatcg aactggaaac gccgttctcc tggcaggatg tcgcggggct ggcagatgtg | 180 |
| gtgcacagcc cggcggatca ggccgcgacg atctcctcag gatcgtttcg caccgacggc | 240 |
| atggtgatca ttccgtgcag catgaaaacc ctggcgggca tccgcgcggg ctacgccgac | 300 |
| gggctggtgg gccgcgccgc tgatgtggtg ctgaaagaga accgtaaact ggtgctggtg | 360 |
| ccgcgcgaaa caccgcttag caccattcat ctggaaaacc tgctggcgct ctcgaagatg | 420 |
| ggcgtggcca tcgtgccgcc catgcccgcc tggtacaacc atcccgcgac gatcgacgac | 480 |
| atcatcaacc atatcgtcgc gcgcgtgctc gatcagttcg ggctcgatgc ccgcaacgcc | 540 |
| cgccgctggc aggggctaaa tcctgcgaaa acagccgaca cccattcatc acgaggagga | 600 |
| aacacgcatg gcgtttgacg atctgcgcag cttttttgcag gcgcttgaag agcaggggca | 660 |
| actgctgagg atcagcgaag aggtgcaggc ggagccggat atcgcggcgg ccgccaacgc | 720 |
| gaccggacgc atcggcgaag gcgcgcccgc gctctggttt gacaatatcc gcggctttac | 780 |
| tgacgcgcgg gtggcgatga acaccattgg ttcatggccg aaccacgcga tctcgctcgg | 840 |
| tctgccgcct gccacaccgg taaagcagca gatagaagaa tttattcgcc gctgggatac | 900 |
| cttcccggtc gcgccggaac gccgcgataa tccgccatgg gcggaaaaca gcgtcgacgg | 960 |
| cgacgacatt aacctgttcg acattctgcc gctgtttcgc ttaaacgacg gcgacggcgg | 1020 |
| gttctacctt gataaagcgt gtgtggtctc gcgcgatccg ctcgatcccg aacacttcgg | 1080 |
| caagcagaat gtcggcatct accggatgga agtgaaaggc aagcgcaagc tcgggctgca | 1140 |

-continued

| | |
|---|---|
| accggtgccg atgcatgaca tcgcgctgca tctgcataag gccgaagagc gtggcgagga | 1200 |
| tttgccggtt gcgattacgc ttggcaacga tccgatcatc acgctgatgg gcgccacgcc | 1260 |
| gctgaaatac gatcagtcgg aatatgaaat ggcgggcgcg ctgcgcgaaa gcccgtaccc | 1320 |
| gatagccacc gcgccgctga ccggtttcga cgtgccgtgg gggtcggaag tgatccttga | 1380 |
| aggggtgatt gaaggacgca agcgcgagat agaagggccg ttcggcgagt ttaccgggca | 1440 |
| ctactccggc gggcgtaaca tgaccgtggt gcgtatcgat aaagtctctt atcgcaccaa | 1500 |
| accgattttc gaatcgctct atctcggcat gccgtggacc gaaatcgact acctgattgg | 1560 |
| cccggcgacc tgcgtgccgc tttaccagca gcttaaagcg gagttccgg aagtgcaggc | 1620 |
| ggtgaacgcg atgtataccc acgggctgct cgcgattatc tccaccaaga aacgctacgg | 1680 |
| cggtttcgcc cgcgcggtgg gcctgcgtgc gatgaccacg ccgcacgggc ttggctacgt | 1740 |
| gaagatggtg attatggtgg atgaggatgt cgatccgttc gatctgccgc aggtgatgtg | 1800 |
| ggcgctgtcg tcaaaagtga acccggcggg cgatctggtg cagttgccga atatgtcggt | 1860 |
| gctggagctt gatcctggct caagcccggc ggggattacc gacaagctga ttatcgacgc | 1920 |
| cactacgccg gttgcgccgg ataaccgcgg gcattacagc cagccggtga agacctgcc | 1980 |
| ggaaaccccg cagtgggtag agaagctgac cgccatgctg gctaaccgta aaaaataagg | 2040 |
| agacgagatg atttgtccac gttgtgccga tgaaaccatc gaaatcatgg cgacgtcgcc | 2100 |
| ggtgaaaggc gtctggacgg tgtatcagtg ccagcattgt ttgtacacct ggcgcgacac | 2160 |
| cgagccgctg cgccgtacca gccgcgagca ttaccccgag cgttccgga tgacgcaggc | 2220 |
| cgatatcgat aacgcgccgg aagtgccaac ggtgccgccg ctgctggcgg atggtaagcg | 2280 |
| ttaa | 2284 |

<210> SEQ ID NO 63
<211> LENGTH: 30
<212> TYPE: DNA
<213> ORGANISM: Artificial sequence
<220> FEATURE:
<223> OTHER INFORMATION: PCR primer

<400> SEQUENCE: 63

| | |
|---|---|
| ctctcatatg aggctaattg tcggaatgac | 30 |

<210> SEQ ID NO 64
<211> LENGTH: 29
<212> TYPE: DNA
<213> ORGANISM: Artificial sequence
<220> FEATURE:
<223> OTHER INFORMATION: PCR primer

<400> SEQUENCE: 64

| | |
|---|---|
| ctctcatatg ttaacgctta ccatccgcc | 29 |

<210> SEQ ID NO 65
<211> LENGTH: 2268
<212> TYPE: DNA
<213> ORGANISM: Escherichia coli

<400> SEQUENCE: 65

| | |
|---|---|
| atgaaactga tcgtcgggat gacaggggct accggtgcgc tcttggtgt ggcattactg | 60 |
| caagcgctgc gggagatgcc gaatgtcgag actcatctgg tgatgtcgaa gtgggcgaaa | 120 |
| accaccattg aactggaaac gccttacagc gctcgcgatg ttgctgccct cgcagacttc | 180 |

```
agccataacc cggcggatca ggcggcgatc atctcatccg gttcttttcg taccgacggc    240
atgatcgtta ttccgtgcag tatgaaaacg ctcgccggta tccgcgctgg ttacgccgat    300
ggcctggtag ggcgcgcggc ggacgtcgtg ctcaaagaag gccgcaaact ggtgctggtg    360
ccgcgtgaaa tgccgcttag caccatccat ctcgaaaata tgctcgcact ttcacgcatg    420
ggcgtggcga tggtgccgcc gatgcctgcc ttttataacc atcccgaaac ggtagatgac    480
attgtccacc atgtggtagc ccgcgtgctg atcaatttg gcctcgaaca tccccacgcc     540
aggcgctggc aaggattgcc gcaggcccgg aattttctc aggagaatga ataatggcat     600
ttgatgattt acgcagcttt ttacaggcgc ttgatgacca cggccagtta ctgaaaatca    660
gcgaagaagt gaacgccgag ccggatctgg cagcagcagc taacgccacc gggcgtatcg    720 gcgacgcgc cccgcgctg tggtttgata atattcgcgg ctttaccgat gcccgcgtgg      780
cgatgaacac catcggttcc tggcagaacc acgcgatttc cctcggcctg ccgccaaatg    840
ccccggttaa aaagcagatt gatgagttta tccgccgctg ggataacttc ccgattgccc    900
cggagcgccg cgccaatcca gcctgggcgc agaacaccgt tgatgcgac gagatcaacc     960 tgttcgatat cctgccgctg tttcgtttaa acgatggcga tggcggtttc tatctcgaca    1020
aagcgtgcgt ggtttcccgc gatccgctcg acccggataa cttcggcaag cagaacgtcg    1080
gcatctaccg catggaagtg aagggcaagc gtaagctcgg cctgcaaccg gtgccgatgc    1140
acgatatcgc cctgcatctg cataaagcag aagagcgcgg tgaagatctg ccgattgcga    1200
tcacgctcgg taacgatccg atcatcacgc tgatgggggc cacgccgctg aaatatgatc    1260
agtccgagta cgaaatggca ggcgcgctgc gtgaaagccc gtacccgatc gccaccgccc    1320
cgttgaccgg ttttgatgtg ccgtgggggtt cagaagtgat cctcgaaggg gtcatcgaaa    1380
gccgtaaacg cgaaatcgaa gggccgttcg gtgagtttac cggcactac tccggcgggc      1440 gtaacatgac cgtggtgcgc atcgataaag tctcttaccg caccaggccg attttcgaat    1500
cgctgtacct cggtatgccg tggaccgaaa tcgactacct gatggggcca gccacctgcg    1560
tgccgctgta tcagcagctg aaagccgagt ccctgaagt gcaggcggta acgccatgt      1620 acacccatgg cctgctggcg attatctcca ccaaaaaacg ctacggcggc tttgcccgcg    1680
cggtgggcct gcgcgcaatg accacgccgc atggtctggg ctacgtgaag atggtgatta    1740
tggtcgatga agacgttgac ccgttcaacc tgccgcaggt gatgtgggcg ctctcctcga    1800
aagtgaaccc ggcaggggat ttggtgcagt tgccgaatat gtccgtgctg gaactcgatc    1860
caggctcaag ccctgcgggg atcaccgaca agctgattat cgacgccact acgcctgtcg    1920
ccccggacaa ccgtggtcac tacagccaac cggtggtgga tttaccggaa accaaagcct    1980
gggctgaaaa actgaccgct atgctggctg cacgtaaata aggagaagaa gatgatttgt    2040
ccacgttgtg ccgatgaaca gattgaagtg atggcgaaat cgccggtgaa agatgtctgg    2100
acggtatatc agtgccagca ttgccttat acctggcgcg ataccgaacc gctgcgccgt      2160
accagccgcg aacattatcc cgaagcgttc cgcatgacgc agaaagatat tgatgacgcg    2220
ccaatggtgc cgagcatccc gccgctgctg gtggaaggta gcgctaa                  2268
```

<210> SEQ ID NO 66
<211> LENGTH: 28
<212> TYPE: DNA
<213> ORGANISM: Artificial sequence
<220> FEATURE:
<223> OTHER INFORMATION: PCR primer

<400> SEQUENCE: 66

```
ctctcatatg aaactgatcg tcgggatg                                          28
```

<210> SEQ ID NO 67
<211> LENGTH: 28
<212> TYPE: DNA
<213> ORGANISM: Artificial sequence
<220> FEATURE:
<223> OTHER INFORMATION: PCR primer

<400> SEQUENCE: 67

```
ctctcatatg ttagcgctta ccttccgc                                          28
```

<210> SEQ ID NO 68
<211> LENGTH: 2268
<212> TYPE: DNA
<213> ORGANISM: Escherichia fergusonii

<400> SEQUENCE: 68

```
atgagactga tcgtcgggat gacaggggcc accggagcgc tcttggtgt ggcattactg          60
caagcgctgc gggagatgcc gaatgtcgag actcatctgg tgatgtcgaa gtgggcgaaa        120
accaccattg aactgaaaac gccttacaac gcccgcgatg ttgctgccct cgcagacttc        180
tgccataacc cggcggatca ggccgcaacc atctcctcag gttccttttcg taccgacggt       240
atgatcgtta ttccgtgcag tatgaaaacg ctcgccggta tccgcgctgg ttacgccgat        300
ggcctggtag ggcgcgcggc ggacgtcgtg ctcaaagaag gccgcaaact ggtgctggtg        360
ccgcgtgaaa tgccgcttag caccatccat ctcgaaaata tgctcgcact ttcgcgcatg       420
ggcgtggcga tggtgccgcc gatgcctgcc ttttataacc atcccgaaac ggtagatgac        480
attgtccacc acgtggtagc ccgcgtgctg gatcaatttg gcctcgaaca tcctcacgcc        540
aggcgctggc aaggattgcc gcaggcccgg aattttttccc aggagaatga ataatggcat      600
ttgatgattt acgcagcttt ttacaggcgc ttgatgacta cggtcagtta ctgaaaatca       660
gtgaagaagt gaacgccgag ccggatctgg cagccgctgc caacgccacc gggcgtatcg       720
gcgacggtgc accggcgctg tggtttgaca atattcgcgg ctttaccgat gcccgcgtgg       780
caatgaacac catcggctcc tggcagaacc acgcgatttc cctcggcctg ccgccaaaca       840
ccccggttaa aaaacagatt gatgagttta tccgccgctg ggataacttt cccattgccc       900
cggagcgccg tgcgaatccg gtctgggcgc agaacaccgt cgatgcgac gagattaatt        960
tgttcgatat tctgccgctg tttcgtttaa acgatggcga tggcggtttc tatctcgaca      1020
aagcgtgcgt ggtttcccgc gatccgctcg acccggataa tttcggcaag cagaatgtcg      1080
gcatctaccg catggaagtg aagggcaagc gtaagctcgg cctgcaaccg gtgccgatgc      1140
acgatatcgc cctgcatctg cataaagcag aagagcgcgg tgaagatctg ccgattgcga      1200
tcacgctcgg taacgatccg atcatcaccc tgatgggggc caccccgctg aaatacgatc      1260
aatcagagta cgaaatggct ggcgcactac gcgaaagccc gtaccgatc gccaccgccc       1320
cgctgaccgg ttttgatgtg ccgtggggct cagaagtgat cctcgaaggc gttatcgaaa      1380
gccgtaaacg cgagattgaa gggccgttcg gtgaatttac cggccactac tccggcgggc      1440
gcaacatgac cgtagtgcgc atcgataaag tctcttaccg caccaaaccg atttttgaat      1500
cgctctatct cggtatgccg tggaccgaaa tcgactacct gatggggcca gccacctgtg      1560
tgccgctgta tcagcaactg aaagccgagt tcccggaagt gcaggcggtg aacgccatgt      1620
acacccacgg cctgctggcg attatctcca ccaaaaaacg ctacggcggc tttgcccgcg      1680
```

| | |
|---|---|
| cggtgggcct gcgtgcgatg accacgccgc acggtctggg ctacgtgaag atggtgatta | 1740 |
| tggtcgatga agacgttgat ccgttcaacc tgccgcaggt gatgtgggcg ctttcgtcga | 1800 |
| aagtgaaccc ggcaggggat ctggtgcagt tgccgaatat gtcagtactg gaactcgacc | 1860 |
| ctggctcaag cccggcgggg atcaccgata agctgattat cgacgccact acgcctgtcg | 1920 |
| ccccggacaa ccgtggtcac tacagccagc cggtggtgga cttaccggaa accaaagcct | 1980 |
| gggctgaaaa actgaccgct atgctggccg cacgtaaata aggagaacaa gatgatttgt | 2040 |
| ccacgttgtg ccgatgaaca gattgaagtg atggcgaaat cgccggtgaa agatgtctgg | 2100 |
| acggtctacc agtgccagca ttgcctttat acctggcgcg atactgaacc gctacgccgc | 2160 |
| accagccgcg aacattaccc gcaagcgttc cgtatgactc aaaaagatat tgatgacgcg | 2220 |
| ccaatggtgc cgagcattcc gccgctgctg gcggcagata agcgctaa | 2268 |

<210> SEQ ID NO 69
<211> LENGTH: 27
<212> TYPE: DNA
<213> ORGANISM: Artificial sequence
<220> FEATURE:
<223> OTHER INFORMATION: PCR primer

<400> SEQUENCE: 69

| | |
|---|---|
| ctctcatatg agactgatcg tcgggat | 27 |

<210> SEQ ID NO 70
<211> LENGTH: 28
<212> TYPE: DNA
<213> ORGANISM: Artificial Sequence
<220> FEATURE:
<223> OTHER INFORMATION: PCR primer

<400> SEQUENCE: 70

| | |
|---|---|
| ctctcatatg ttagcgctta tctgccgc | 28 |

<210> SEQ ID NO 71
<211> LENGTH: 2304
<212> TYPE: DNA
<213> ORGANISM: Paenibacillus polymyxa

<400> SEQUENCE: 71

| | |
|---|---|
| atgaagaaaa tcattgtagg aatatcggga gcgacagggt caatctttgg tatccgtata | 60 |
| ttgcaaaaat tacgggaggc tggagtccaa agccatctgg tgctatcccc gtgggctatt | 120 |
| gccaacattc cctatgagac aggctacacg gtgaaggatg tgaaggcaat ggcggatgca | 180 |
| gtctactcgt ataaggatca ggccgcacgt atttctagcg gctccttccg ggtagatggt | 240 |
| atggtcgtcg ctccttgcag tatgaagact cttgcctcta ttcgtatcgg tatggcggac | 300 |
| aacctgctta cccgatcagc ggatgtgata ctgaaggagc gaaagaagct gctgctcatg | 360 |
| accagagaaa caccattaag cagtatccat ctggaaaata tgctggagct gtcacgtatg | 420 |
| ggcgtgatga tcctgccgcc gatgcctgcc ttttataatc atcctgcaag tatcgaggaa | 480 |
| ttagtggatc atattgtttt tcgcgcattg gatcagttcg gtattgtcac aaccgcagcc | 540 |
| aaacgctggg atgggatgaa gcagaatgac tccaggctgc accagaattg agaaatcgaa | 600 |
| agacgaagga gaatgaatga tggcttataa agactttcgc gattttctac acaccttgga | 660 |
| aaaggaggga caattactca cgatcagcga tgaggtaaag ccggagccgg acctcgcagc | 720 |
| agctaacaga gcattaaaca atcttggaga taagacgcct gctctcttt tcaacaacat | 780 |
| ctatggatat acggatgctc gtattgcaat gaatgtgatg ggctcctggc ccaatcatgc | 840 |

```
cctcatgatg ggaatgccca aaaatacgcc gctcaaggag cagttttttg aatttgccag    900
acgctatgaa caatttccgg tgcccgtgaa gcgggaagaa gccgctcctt ttcatgaagt    960
cgaaattacg gagaatatta atttgtttga tattttgccg ttgtttcgtt tgaatcaggg   1020
ggacggaggg ttttatttgg ataaagcaat tctaatttca cgcgatctgg atgacccgga   1080
cacctacggt aagcaaaatg tcggcttata ccggatgcag gtgaaaggca agaaccgttt   1140
gggcatccag cctgtaccac agcatgatat tgcgatccat atccgtcagg ctgaggagcg   1200
tggcgaaaat ctgaaggtgg ctattgccct cggatgtgag cctgtgatta acggctgc    1260 ttctacgcca ctgctgtacg atcaatccga atatgagatg gcgggcgcca ttcagggcga   1320
gccttatcgt gtggtcaaag cgaaggatgc agatctggat ctgccttggg gagccgaggt   1380
cattttggaa ggcgaagtgt tagcaggtga acgtgagtat gaaggtccat tcggtgaatt   1440
cacaggtcac tattccggcg gtcgcgcgat gccagtcatt cagattaatc gtgtatatca   1500
ccgcaaacag cctatctttg agcatctgta catcggatg ccttggacgg aaacggatta    1560
tatgatcggt gtgaatacaa gtgtaccgtt gtttcagcag cttaaggatg cttttcctaa   1620
tgaaatcgta gctgttaatg ccatgtatac gcatgggctg gtcgctatta tttccacgaa   1680
aacccggtat ggcggctttg cgaaggctgt gggaatgcgt gcgttaacga ctccgcatgg   1740
attggggtat tgcaagctgg tgattgtggt ggacgaggag gtcgatccgt tcaatctgcc   1800
gcaagtcatg tgggctttat ccaccaagct tcatccaaag catgatgctg tcattgttcc   1860
tggcttgtct attttaccgc ttgaccccgg ctctgatccg gcaggtatga cgcacaaaat   1920
gatactggat gcgacgacac ctgtagcacc ggatattaga ggccattact cgcagccgct   1980
cgattccccg ctgggtgtag cggaatggga gaaaaagttg agccaaatgc ttcgctaaat   2040
atttttaaaa acaaagaaaa tttaaaggag tgctgacaga tgcatatttg tccccgttgt   2100
gagtccaatc gttcagaagt cgtttcccat tcgccggtta aggtgcctg ggaggttttg    2160 ttgtgccctg tatgcctgtt cacatggcga acctcagaac cggatagcat tactgatcca   2220
gcaaagtata atcggcgtt caaggtaaac ccccaagata ttccggatgc tgctcatgtt     2280
cctcctattc cagagcggat atag                                          2304
```

```
<210> SEQ ID NO 72
<211> LENGTH: 35
<212> TYPE: DNA
<213> ORGANISM: Artificial sequence
<220> FEATURE:
<223> OTHER INFORMATION: PCR primer

<400> SEQUENCE: 72
ctctcatatg aagaaaatca ttgtaggaat atcgg                                35

<210> SEQ ID NO 73
<211> LENGTH: 31
<212> TYPE: DNA
<213> ORGANISM: Artificial sequence
<220> FEATURE:
<223> OTHER INFORMATION: PCR primer

<400> SEQUENCE: 73
ctctcatatg ctatatccgc tctggaatag g                                    31

<210> SEQ ID NO 74
<211> LENGTH: 2318
<212> TYPE: DNA
```

<213> ORGANISM: Pantoea ananatis

<400> SEQUENCE: 74

```
atgagtagat tactgttaat ttcattcgta cacgaacgtt atttgcaagg aagtcagatg      60
agaattgtaa tcggtatgac gggagcaaca ggtgcccctt taggggtggc tctgctcagc    120
attttgcagg aaatcaaaga ggttgaaact catctgattt tgagcaagtg ggctaaaacc    180
acaattgaac tcgaaacgcc tttttcatcg cgtgaggtga tgagcatggc tgatgttgtg    240
tatggcccgt ccgaccaggc cgctactctc tcgtcaggtt cttttcacac cgatgggatg    300
gtcattattc cttgcagtat gaaaaccttc gcgggaattc gcatgggata cgcggaaggc    360
cttattggac gggctgctga tgtcgtcatt aaagaaggca gaaaacttgt gctggtcccc    420
agagagacgc ctctcagcac cattcacctg gaaaatatgc tagccctttc ccgtcttggc    480
gtatccatgg ttccgcccat gcccgctttt tataaccacc ccgcagtaat tgatgatgtg    540
atcgatcatg tcgtttctcg tgttctcgac cagtttggga ttgcctcgcc aaaggcaaat    600
cgctggaaag gcctgaacaa ttctaagaaa tccctgagta tggagagtaa ataatggctt    660
ttgatgacct acgtagcttc cttaaggctc tggacgagca ggggcagctt cttgagattg    720
atgaagaggt tttacccgaa cctgatattg ccgcggccgc taatgctaca ggccgaattg    780
gtgaaggtgc accggcaatc tcattcaaaa aaataaaggg gttcaatcat gctcatgttg    840
tgatgaacac tattggttcc tggcaaaacc atgcaatttc actgggcctc ccaatgaata    900
ccccagtgaa acagcagata gatgaattca ttcgtcgctg ggacactttt cctgtggcac    960
cagagcggcg cgacaatgcg ccctggtcag aaaataccgt tgattgtgaa gagatcaatc   1020
tcttcgacat ccttcccctg ttccgcctga cgacggcga cggcggtttc tatcttgata   1080
aggcctgcgt agtatcacgt gacccgcttg atccagaaca tttcggtaag caaaacgtcg   1140
gcatttaccg gatggaggtg aaaggtaaac gtaaactcgg gctccagccc gtgccgatgc   1200
atgacattgc acttcatctc cataaggccg aagaacgcgg cgacgatctg ccagtggcta   1260
ttacgctggg caatgacccc attattacat tgatgggcgc cacgccgctg aaatacgacc   1320
agtcagaata tgagatggca ggtgcgctgc gtgaaagccc gtaccccatc gcctccgcgc   1380
ctctgaccgg cttttgatgtg ccgtggggat cggaagtcat tcttgaaggc gtgatagaag   1440
ggcgcaaacg tgagattgaa ggaccgtttg gcgaattcac cggccattat tccggcggtc   1500
gcaatatgac cgttgtgcgg attgataagg tctcctaccg cactaagcca atattcgagt   1560
cattgtatct gggaatgccc tggaccgaaa ttgattatct gatgggcccg gcaacctgtg   1620
tcccttttgta tcaacagctg aaagcggatt ccctgaggt gcaggctgta aatgcaatgt   1680
atacacacgg attactggcc attatttcta caaagaaacg ttatggtgga tttgcccgtg   1740
ctgtaggcgt acgggcgatg acaaccccgc atggtctggg ctacgtcaag atggtgatca   1800
tggtcgatga ggatgtcgat ccctttaacc tgcctcaggt gatgtgggcg ctgtcttcaa   1860
aggtcaatcc gcaaggcgat ctcgttcaac tgccaaacat gtccgtactg gaactggacc   1920
cgggttccag ccctgcggga atcacggata aacttgtgat cgatgcgacg actcccgtgg   1980
caccggatac ccgcggccac tacagtcagc cggtaaaaga cctgccagaa acttcaatct   2040
gggttgagaa gttaacgtcc ctgttatcaa atcgcggtta aggagaaagt atgatttgtc   2100
cacgttgtgc tgatgaacac attgaaatca tggcaacatc cccagttgag gggatatgga   2160
cggtgcatca gtgtcagcat tgcctgtaca catggcgcaa tacagagcca gcccgaagaa   2220
cggagcggga acattatcct gaagccttcc ggatgactca acgtgatatt gataatgcgc   2280
```
cggaagtccc gtctgtccct cctctgttag ctaagtaa                                2318

<210> SEQ ID NO 75
<211> LENGTH: 38
<212> TYPE: DNA
<213> ORGANISM: Artificial sequence
<220> FEATURE:
<223> OTHER INFORMATION: PCR primer

<400> SEQUENCE: 75
ctctcatatg agtagattac tgttaatttc attcgtac                                38

<210> SEQ ID NO 76
<211> LENGTH: 32
<212> TYPE: DNA
<213> ORGANISM: Artificial sequence
<220> FEATURE:
<223> OTHER INFORMATION: PCR primer

<400> SEQUENCE: 76
ctctcatatg ttacttagct aacagaggag gg                                      32

<210> SEQ ID NO 77
<211> LENGTH: 29
<212> TYPE: DNA
<213> ORGANISM: Artificial Sequence
<220> FEATURE:
<223> OTHER INFORMATION: PCR Primer

<400> SEQUENCE: 77
ctcttctaga tacgtcctaa acacccgac                                          29

<210> SEQ ID NO 78
<211> LENGTH: 40
<212> TYPE: DNA
<213> ORGANISM: Artificial sequence
<220> FEATURE:
<223> OTHER INFORMATION: PCR primer

<400> SEQUENCE: 78
gaccaaccat tgctgacttg cgtatccata gtcaggcttc                              40

<210> SEQ ID NO 79
<211> LENGTH: 20
<212> TYPE: DNA
<213> ORGANISM: Artificial sequence
<220> FEATURE:
<223> OTHER INFORMATION: PCR primer

<400> SEQUENCE: 79
caagtcagca atggttggtc                                                    20

<210> SEQ ID NO 80
<211> LENGTH: 30
<212> TYPE: DNA
<213> ORGANISM: Artificial sequence
<220> FEATURE:
<223> OTHER INFORMATION: PCR primer

<400> SEQUENCE: 80
ctcttctaga tgatcagtac caagggtgag                                         30

<210> SEQ ID NO 81
<211> LENGTH: 510
<212> TYPE: DNA

<213> ORGANISM: Acinetobacter baumannii

<400> SEQUENCE: 81

```
atgcgtaaac gacaaccagt acttaagcag gaaaagactt taaatcctga attgaaaaca    60
tggttgtatg cgtctggttc tctgacacaa caactcactg agctgggtgg ggggaagttc   120
agcgtaaagc ctttcaaaga acatttccag cgtttaactt ttgccgacag tcaatggatg   180
aacatgcccc atactcacac ttcttgggta agggaaacct atttatatgg cagtgatgta   240
gagccttggg tgaaagcaaa aagtattttt ccaattcaaa gtttacaaaa aaaagcccgt   300
atatttcagc atattggttc taagccgata ggtctttttt tatttcaaag aacaacacca   360
ctttgtgatc gccgggttat tcgtttacct gaaggctgga cgcgacaaag ttgctatact   420
tggcatggat gtaaatttat tgttcaagaa acattcttac cggcttttga agcttttta   480
tatcagcagc acgacaagga attactatga                                    510
```

<210> SEQ ID NO 82
<211> LENGTH: 552
<212> TYPE: DNA
<213> ORGANISM: Azotobacter vinelandii

<400> SEQUENCE: 82

```
gtgaccgctg ctcccgcttt ccaatggctc ggcgccgacc aactgcatcc cgccccccg     60
gccgtcctgg ccgactggct gttcgacagc ggctcgctga cccgccggct gaccgccctt   120
tccgccggcc gtttcgccgt gacgccgctg ccgaaggct ggcaggtgct gcgcgacgac    180
gaatgcaccg ccctcgacgt ggtgccgggc agcaccggct gggtacgcga ggtctacctg   240
ctcggcgccg agcggccctg ggtgttcgcc cgcagcgtgg cggcccgcga ggctctggcg   300
ggtttctccg gcgtactcgc cgaactcggc cggcggcccc tcggcgaact gctgttcagc   360
gacccagcct tcgcccgcgg cccgctgcag gccacgcact atccgccgga ctggctgccg   420
gccgggatac gctgccccgg actctgggga cggcgctccc gtttccaccg ggaaaccctg   480
agcgtgctgg tggcggaagt cttcctgccg gagctctggc gctaccaggg aatcgacccg   540
gacacccctat aa                                                      552
```

<210> SEQ ID NO 83
<211> LENGTH: 552
<212> TYPE: DNA
<213> ORGANISM: Chromobacter salexigens

<400> SEQUENCE: 83

```
atgtctcctg accgcttccc aggctggccg cactggctgc ccatcgccgc gcagcgtcct    60
cgaatgagcc ccgactggtg gccctgggtg gcctctcgcg attcactgac cgcgcgcttg   120
cgcatcgcca gccccgtcc attctcggtg cgtctgctca cccagggcgt gaccaggcca   180
cgcctcgacg aagcccaggc actggggctg ccgcaccgca cgcacgtctg caccgggaa   240
gtcctgttgc ggctgggcaa tgcctcctgg gttgcggccc gttccgtggc accgctggag   300
ggactgtccg gcgcacggct atgcacgctg ggagagcgtt cgctgggcag ttggctatttt 360
cggcaaccta acctcgagcg cggccccatc gaagcgatcc gtgcgccggc catgacgggg   420
ctggacgcct ggcgaggcga cgccggcccc tggggcggc gctcgctcct gcgcgtgggc   480
agaaccagga ttctcgtcca ggaattcttt ctcgccgcga tggccgctga cctctcgctg   540
ccatcgcgct aa                                                      552
```

```
<210> SEQ ID NO 84
<211> LENGTH: 498
<212> TYPE: DNA
<213> ORGANISM: Citrobacter koseri

<400> SEQUENCE: 84
atgtcacacc ctgcgttaac gcaactgcgt gcgctgcgct attttaaaga gattcctgcg      60
ctggattccc ggttgctcga ctggttactt ctggaagatt ccatgaccaa acgttttgag     120
caagaaggga acgggtaag cgtgacattg cttcgggaag cgtttgttgg tccacatgaa      180
gtggctgaag aggtggcgct gctaccggtc gaatcccgct actggttacg tgaaattttg     240
ttatgtgcag acggcgaacc ctggcttgcc gggcgtaccg tcgtgcctga atcaacgttg     300
tgcggccctg agctggcctt acaaaatctg ggaaaaacgc cgttagggcg ctacctgttt     360
acatcatcaa cgttgacccg agattttatt gagattggtc gtgatgccgc actgtggggg     420
cgtcgttccc gcctgcgtct gagcggtaag ccgctgatgc ttaccgagct gttttttgccc    480 gcatcaccgt tgtattaa                                                   498

<210> SEQ ID NO 85
<211> LENGTH: 498
<212> TYPE: DNA
<213> ORGANISM: Citrobacter youngae

<400> SEQUENCE: 85
atgccacacc ctgcgttaac gcaactgcgt gcgctgcgtt attttgatga gatcccggcg     60 ctggaccccgc agctgctcga ctggttgtta ctggaagatt cgatgaccaa acgttttgag    120
cagcagggaa acaagtcac cgttacgttg attcgcgaag cgttcgttgg gcaaaatgag     180
gtggctgaag aactgatgct gctgcctaaa gaatcccgct actggttacg cgaaatcctg    240
ttatgcgcgg atggtgagcc ctggcttgcc gggcgtaccg tggtgcctga atcaaccctg    300
tgcggccctg aactggcctt acaaaatctg gggaaaaccc cgctcggacg ctacctgttt    360
acgtcatcga cattgacccg agattttatt gagattggcc gcgatgcagc gctgtggggg    420
cgacgttccc gcctgcggct gagcggtaag ccattgatgc ttaccgagct ttttctacct   480
gcatcgccgt tgtactga                                                  498

<210> SEQ ID NO 86
<211> LENGTH: 498
<212> TYPE: DNA
<213> ORGANISM: Enterobacter cloacae

<400> SEQUENCE: 86
atgtcacacc ctgcgctaac gcaactgcgt tcgctgcgct atttcgacca aatacctgcg     60 cttgaccccgc agcagcttga ctggttgctg ctggaagatt ccatgactaa acgttttgag   120
caacagggca agacggttac ggtgacgatg attcaggaag ggtttgtcac ctccgctgac   180
attgccagtg agctgccgct gttaccaaaa gaagaacgcg actggttgcg tgaaattctg    240
ctctgcgcgg atggtgagcc gtggctcgcc ggacgaaccg tggtgcctga atccacccttt   300 tccgggcctg agctggcact gcaacggctg ggaaacaccc cgctcgggcg gtaccttttc   360
acctcgtctg aacttacccg ggattttatt gaaattggac gcgatgccga actgtgggga   420
cgtcgttccc gtcttcgcct gagcggtaaa ccgttaatac tgacggagct tttttttaccg   480 gcatcgccgt tgtactga                                                  498

<210> SEQ ID NO 87
```

```
<211> LENGTH: 567
<212> TYPE: DNA
<213> ORGANISM: Marinobacter aquaeolei

<400> SEQUENCE: 87
atgccgttaa aggactgtga ccagccccc  gagctgagca tacctcccac gttctggtac      60
cggtcgctgg tggcggccgg cctttactgt cctgaggttc atggcccggc ccgctactgg     120
ctaacagtag agggatcgtt tacccgggcc ctgcagcaaa aatgtcagga acgctttcac     180
gttgagattc tcagggaggg ttttttcgacc ccaacccctg aagaggcaaa gcgcctgaac    240
ctggcaccac gccagctcgc ctgggtacgg aagttcgcc tttgcggtga cggccgccct      300
tgggtgctgg cccggacagt gatcccacag acctgtctgc atggccatgg ccgccgcctg    360
cgcaatcttg gcaacaagcc cctgggcgcc tatctgttca gcagcccgga gtggcagcgg    420
gggcctctgg aaacaggtct ctgtaaagcc cgtagcaacg gtcaccctcg tcttgcccgc    480
agatccctgt tccaccgggg ttcctgcgct cttctggtgg gggaatatct tctaccccgg    540
ttataccagt cgcccaaccg gggttaa                                        567

<210> SEQ ID NO 88
<211> LENGTH: 540
<212> TYPE: DNA
<213> ORGANISM: Marinomonas mediterranea

<400> SEQUENCE: 88
atgacgttac tcaataaaaa cgctgcccga caatttgact acgaatggca cgcactaagc     60
tgcgtcaatc gacaacagat tcccagtaac attcttcctt gggtgagtac gccagactcg    120
ttgacggcaa agctgcaaca agcagggtca tttaaggtgg aggtcattag cgattacatt    180
ggcttaccaa cacagagaga gcgtaaccga ctcaacttac acgctcgtga gcaagcgaga    240
atccgtaccg tgttacttta ctgcaaccac cacgttgtta tttatggtcg ctcaattatt    300
cctttacgct cgttacgagg ccattggcgc tgtctgtcta agctcgcaga taagccactt    360
ggtggctacc ttttcaagaa taagcaactt tcacgcagtc ctatcgaagt tactcagctt    420
cccgctggat taatgcaaaa cacggaagag agtttatggg caaggcggtc tattttctat    480
ggctatggtc cgggtatctt ggttaatgaa gcattttacc ctaccatagg ccagctgtag    540

<210> SEQ ID NO 89
<211> LENGTH: 513
<212> TYPE: DNA
<213> ORGANISM: Pantoea ananatis

<400> SEQUENCE: 89
atgacgcaag acccgctccg ttcgttacgt tcacttaact ggctggcgct ggacgatgcc     60
gcattgacgc aaccgcttcg tgactggcta atggaagagg attccatgac gcgacgcttt    120
gaacagcatt gccagaaggt cagggtggaa cctgtacgtg aggactttat ctccgccgat    180
gaactcggcg atgaaggggc attactccct gccgatcagc gttctggct  gcgagaagtc    240
attctctacg gggatgagga accttggctg gcagggcgca cgctggtgcc agaaagtacc    300
ctcaacggcc cggaagcgat gttacagcaa ctcggtacgc gcccgctggg gcgttatctg    360
ttctcgtcat caacgctgac ccgcgatttc attgagcctg gccgcgttga tgcgctctgg    420
ggacgccgct cgcgcctgcg actgtcaggg aaaccgctgc tgttaacgga actgtttta   480
ccggcttcgc cgctctatcg tgatcaaggt taa                                 513
```

<210> SEQ ID NO 90
<211> LENGTH: 546
<212> TYPE: DNA
<213> ORGANISM: Pseudoalteromonas haloplanktis

<400> SEQUENCE: 90

```
gtgattactt tccctgtttc attatctgcc gattggcaat gtgcctcact gtttagtgat    60
ttatcgagtg cagagcaaga gtggttattt gaaccgcatt cattaacagc caaattaaaa   120
agtcgctcac agtgttttag tgtaaaagta cttagtgagc aagagtttga gcttagtgca   180
gagcaacaac aattattagg ctgtacgcaa actactgcgc ttaaccgtga ggtactttta   240
ctttgcgaca ataaaccggt tgtatatgcg caaagctggt tgccagcaag tgttaacgcc   300
gcaaataata aattacataa tatggggggag cgaccattag gcgatgtgat ttttcaagat   360
ccacaattaa cccgcacaga tatagaaatt gcgcgcttta atacccagca ttcattacaa   420
cagcttgttg cacaattaaa gttaccatcg caaagtttac ttggccgtcg cagtctatt    480
tcgcttaaag actataaatt tttagtgtgt gaagtgtttt taccaggagc gtatttgtac   540
tcatga                                                             546
```

<210> SEQ ID NO 91
<211> LENGTH: 663
<212> TYPE: DNA
<213> ORGANISM: Ralstonia eutropha

<400> SEQUENCE: 91

```
atgagcgcgc agtccgcgcg ccgctgcagc tggagcccgc acctggcctt tgatgcagcc    60
atcacgccca acctgcggcg ctgggtgacc ggtgacgacg gctcgctgac cgcgcgcctg   120
gtggcagcat cggagcgctt cgcgtggcg cgcctgctgc agcgcccgca gcgcccgctc   180
gccgatgaat ggcaggtgct gggccagcac gaccgcaccc ccgcgctgac gcgcgaggtg   240
ctgctgatct cgacgatat ccccgccata tttgcccata ctgtggtgcg ccagcgccat   300
gcgcgccgcg actggccgtt cctgcgcggg ctgggcgagc gcccgctggg cggccggctg   360
tttgtcgacc cggcggtggc gcgcgagccg ttccagtttg cgcggctgct gccgcaccat   420
ccgctgcgcc aggccttgca gcgtgtgctg ccggccatgg cgccactgcc catgctgccg   480
gcgcggcgct cggtgttccg gcgcggcgac ggcgtcatgc tcgtgacaga agtgttcctg   540
ccggacctgc tgtcgcggcc atccccgggg accgaggcga ttccgtatcc caggtatttg   600
cggactacag accgaagccc ctctacacac actaccgaaa ccaagaaaga gaccacgaga   660
tga                                                                 663
```

<210> SEQ ID NO 92
<211> LENGTH: 561
<212> TYPE: DNA
<213> ORGANISM: Shewanella putrefaciens

<400> SEQUENCE: 92

```
atgaatgtga ctagcttaag cttcccctat ggtgaatcta ttcaatggtt tgtgctgat     60
cgtaccgata aacttccccc gtcaccgcta aaagagtggt tactcgcccc aggcagcctg   120
acaaaaaac tcaaaacctg ctgcaatcag tttgaagtca aagtcctcgg tgaaggccaa   180
ctcgcccct tcaaagatga atatcctcag caaggctctg tttgggttcg tgaagtattg   240
ctatgccttg ataatgttcc ttgggtgttt gccagaacct taatcccact ctctttgctg   300
tctgaacgag aagcggattt tctcggtttg ggttctcgtc cccttggcga attactcttt   360
```

```
agccaagata actttatccc cggcagaata gaagtcgcca gctttgatac aggtagtcgt    420
cttgcacact tagctgcaag tttagatcaa agggttgaac atctcctgtg gggacgccgt    480
cgctattttc accacggcca ggatgagatg atcgtcagtg aaatattttt acctgcggcc    540
gagcgagcaa tttgccagtg a                                              561
```

```
<210> SEQ ID NO 93
<211> LENGTH: 564
<212> TYPE: DNA
<213> ORGANISM: Thiobacillus denitrificans

<400> SEQUENCE: 93
```

```
gtgatcgcca cgcgcgacga cgtttgccgg caggccggtc tgcagtatgg ctggctgccc     60
catgccttcc aggcgccgcg gacgctcgcg ggctggctgt ccgatcgcgg ttcgctcacc    120
cagcgcctgc ggtcccgtta ccgtgatttc cgcgtgcttc cggtgctgcg cggcgtcgcg    180
gcgccttttc ccgacgaaag cggcgcgctc ggcctcgcgc gcgatgcaag cgcctacgtg    240
cgcgacgtcc tgctcctcgg cgatggcaag gcccgcgttt cgcgcacag cgtgctgccg    300 cgcgcggcct tgcgcggcgg atggaacggc atcgcccggc tcggcacgag accgctcggc    360
gaagcactgt ttcgcacccc ccgtgtccgc cgtctggcca tgacgatgcg ccgggtcgac    420
gcgcggcacc cgctttattg cgccgcgcgc cgccatgccg aggtcgccga gcgcgcactg    480
tgggcgcggc gctcggtatt ttgcctggac ggccacccac tgctggtcag tgaagtcttt    540
ttgcccgccc tattaacgcc atga                                           564
```

```
<210> SEQ ID NO 94
<211> LENGTH: 29
<212> TYPE: DNA
<213> ORGANISM: Artificial sequence
<220> FEATURE:
<223> OTHER INFORMATION: PCR primer

<400> SEQUENCE: 94
ctctcatatg cgtaaacgac aaccagtac                                       29
```

```
<210> SEQ ID NO 95
<211> LENGTH: 34
<212> TYPE: DNA
<213> ORGANISM: Artificial sequence
<220> FEATURE:
<223> OTHER INFORMATION: PCR primer

<400> SEQUENCE: 95
ctctcatatg tcatagtaat tccttgtcgt gctg                                 34
```

```
<210> SEQ ID NO 96
<211> LENGTH: 23
<212> TYPE: DNA
<213> ORGANISM: Artificial sequence
<220> FEATURE:
<223> OTHER INFORMATION: PCR primer

<400> SEQUENCE: 96
ctctcatatg accgctgctc ccg                                             23
```

```
<210> SEQ ID NO 97
<211> LENGTH: 28
<212> TYPE: DNA
<213> ORGANISM: Artificial sequence
<220> FEATURE:
<223> OTHER INFORMATION: PCR primer
```

```
<400> SEQUENCE: 97
ctctcatatg ttatagggtg tccgggtc                                28

<210> SEQ ID NO 98
<211> LENGTH: 25
<212> TYPE: DNA
<213> ORGANISM: Artificial sequence
<220> FEATURE:
<223> OTHER INFORMATION: PCR primer

<400> SEQUENCE: 98
ctctcatatg tctcctgacc gcttc                                   25

<210> SEQ ID NO 99
<211> LENGTH: 27
<212> TYPE: DNA
<213> ORGANISM: Artificial sequence
<220> FEATURE:
<223> OTHER INFORMATION: PCR primer

<400> SEQUENCE: 99
ctctcatatg ttagcgcgat ggcagcg                                 27

<210> SEQ ID NO 100
<211> LENGTH: 27
<212> TYPE: DNA
<213> ORGANISM: Artificial sequence
<220> FEATURE:
<223> OTHER INFORMATION: PCR primer

<400> SEQUENCE: 100
ctctcatatg tcacaccctg cgttaac                                 27

<210> SEQ ID NO 101
<211> LENGTH: 31
<212> TYPE: DNA
<213> ORGANISM: Artificial sequence
<220> FEATURE:
<223> OTHER INFORMATION: PCR primer

<400> SEQUENCE: 101
ctctcatatg ttaatacaac ggtgatgcgg g                            31

<210> SEQ ID NO 102
<211> LENGTH: 26
<212> TYPE: DNA
<213> ORGANISM: Artificial sequence
<220> FEATURE:
<223> OTHER INFORMATION: PCR primer

<400> SEQUENCE: 102
ctctcatatg ccacaccctg cgttaa                                  26

<210> SEQ ID NO 103
<211> LENGTH: 29
<212> TYPE: DNA
<213> ORGANISM: Artificial sequence
<220> FEATURE:
<223> OTHER INFORMATION: PCR primer

<400> SEQUENCE: 103
ctctcatatg tcagtacaac ggcgatgca                               29

<210> SEQ ID NO 104
```

```
<211> LENGTH: 26
<212> TYPE: DNA
<213> ORGANISM: Artificial sequence
<220> FEATURE:
<223> OTHER INFORMATION: PCR primer

<400> SEQUENCE: 104
ctctcatatg tcacaccctg cgctaa                                              26

<210> SEQ ID NO 105
<211> LENGTH: 28
<212> TYPE: DNA
<213> ORGANISM: Artificial sequence
<220> FEATURE:
<223> OTHER INFORMATION: PCR primer

<400> SEQUENCE: 105
ctctcatatg tcagtacaac ggcgatgc                                            28

<210> SEQ ID NO 106
<211> LENGTH: 28
<212> TYPE: DNA
<213> ORGANISM: Artificial sequence
<220> FEATURE:
<223> OTHER INFORMATION: PCR primer

<400> SEQUENCE: 106
ctctcatatg ccgttaaagg actgtgac                                            28

<210> SEQ ID NO 107
<211> LENGTH: 26
<212> TYPE: DNA
<213> ORGANISM: Artificial sequence
<220> FEATURE:
<223> OTHER INFORMATION: PCR primer

<400> SEQUENCE: 107
ctctcatatg ttaaccccgg ttgggc                                              26

<210> SEQ ID NO 108
<211> LENGTH: 32
<212> TYPE: DNA
<213> ORGANISM: Artificial sequence
<220> FEATURE:
<223> OTHER INFORMATION: PCR primer

<400> SEQUENCE: 108
ctctcatatg acgttactca ataaaaacgc tg                                       32

<210> SEQ ID NO 109
<211> LENGTH: 29
<212> TYPE: DNA
<213> ORGANISM: Artificial sequence
<220> FEATURE:
<223> OTHER INFORMATION: PCR primer

<400> SEQUENCE: 109
ctctcatatg ctacagctgg cctatggta                                           29

<210> SEQ ID NO 110
<211> LENGTH: 24
<212> TYPE: DNA
<213> ORGANISM: Artificial sequence
<220> FEATURE:
<223> OTHER INFORMATION: PCR primer

<400> SEQUENCE: 110
```

-continued

```
ctctcatatg acgcaagacc cgct                                          24

<210> SEQ ID NO 111
<211> LENGTH: 33
<212> TYPE: DNA
<213> ORGANISM: Artificial sequence
<220> FEATURE:
<223> OTHER INFORMATION: PCR primer

<400> SEQUENCE: 111
ctctcatatg ttaaccttga tcacgataga gcg                                33

<210> SEQ ID NO 112
<211> LENGTH: 36
<212> TYPE: DNA
<213> ORGANISM: Artificial sequence
<220> FEATURE:
<223> OTHER INFORMATION: PCR primer

<400> SEQUENCE: 112
ctctcatatg attactttcc ctgtttcatt atctgc                             36

<210> SEQ ID NO 113
<211> LENGTH: 33
<212> TYPE: DNA
<213> ORGANISM: Artificial sequence
<220> FEATURE:
<223> OTHER INFORMATION: PCR primer

<400> SEQUENCE: 113
ctctcatatg tcatgagtac aaatacgctc ctg                                33

<210> SEQ ID NO 114
<211> LENGTH: 23
<212> TYPE: DNA
<213> ORGANISM: Artificial sequence
<220> FEATURE:
<223> OTHER INFORMATION: PCR primer

<400> SEQUENCE: 114
ctctcatatg agcgcgcagt ccg                                           23

<210> SEQ ID NO 115
<211> LENGTH: 32
<212> TYPE: DNA
<213> ORGANISM: Artificial sequence
<220> FEATURE:
<223> OTHER INFORMATION: PCR primer

<400> SEQUENCE: 115
ctctcatatg tcatctcgtg gtctctttct tg                                 32

<210> SEQ ID NO 116
<211> LENGTH: 32
<212> TYPE: DNA
<213> ORGANISM: Artificial sequence
<220> FEATURE:
<223> OTHER INFORMATION: PCR primer

<400> SEQUENCE: 116
ctctcatatg aatgtgacta gcttaagctt cc                                 32

<210> SEQ ID NO 117
<211> LENGTH: 29
<212> TYPE: DNA
```

<213> ORGANISM: Artificial sequence
<220> FEATURE:
<223> OTHER INFORMATION: PCR primer

<400> SEQUENCE: 117

| ctctcatatg tcactggcaa attgctcgc | 29 |

<210> SEQ ID NO 118
<211> LENGTH: 23
<212> TYPE: DNA
<213> ORGANISM: Artificial sequence
<220> FEATURE:
<223> OTHER INFORMATION: PCR primer

<400> SEQUENCE: 118

| ctctcatatg atcgccacgc gcg | 23 |

<210> SEQ ID NO 119
<211> LENGTH: 29
<212> TYPE: DNA
<213> ORGANISM: Artificial sequence
<220> FEATURE:
<223> OTHER INFORMATION: PCR primer

<400> SEQUENCE: 119

| ctctcatatg tcatggcgtt aatagggcg | 29 |

<210> SEQ ID NO 120
<211> LENGTH: 1443
<212> TYPE: DNA
<213> ORGANISM: Corynebacterium efficiens

<400> SEQUENCE: 120

| gtgcagcaca ctccttttca gtgtaaaaggt ctcaggcgtg ctatgaatag gggtgtgagt | 60 |
| tggacagttg atatccccaa ggaagttctc ccggatctgc cgcccctgcc cgagggcatg | 120 |
| aacgagcagt tccaggacac catcgcccgt gacgccaagc agcagcccac ctgggaccgt | 180 |
| gcccaggccg acaacgtgcg ccgtatcctc gaatcggttc ctccgatcgt ggtggcccct | 240 |
| gaggtcatcg agctgaagaa gaagctcgca gatgtggcca acggcaaggc attcctgctc | 300 |
| cagggtggtg actgcgccga gaccttcgag tccaataccg agccccatat ccgggccaat | 360 |
| atcaagactc tcctccagat ggccgtggtg ctcacctatg gtgcctccac acccgtcatc | 420 |
| aagatggccc gtatcgccgg ccagtacgcc aagccacggt ccgccgatct ggatgccaac | 480 |
| ggtctgccaa actaccgcgg tgacatcgtc aacggtgtgg aagccacacc ggaggcacgc | 540 |
| cggcatgacc ccgcgcgcat gatccgcgcc tacgccaact cctccgccgc catgaacctg | 600 |
| gtgcgtgccc tgaccagctc cgggaccgcc aacctctacc gcctcagtga ctggaaccgc | 660 |
| gagttcgtcg ccaactcccc cgccggtgcg cgctatgagg cgctcgcccg agagatcgac | 720 |
| tccggtctgc gcttcatgga ggcctgtggc gtgtccgatg aatccctgcg caccgcggag | 780 |
| atctactgct cccacgaggc tctcctcgtg gattatgagc gctccatgct gcgcctgggt | 840 |
| gaggatgaaa acggtgagca ggccctctat gatctctctg cacaccagct gtggatcggt | 900 |
| gagcgcaccc gtggcatgga tgatttccac gtcaatttcg ccgccatgat cgccaacccg | 960 |
| gtgggcatca agatcggccc gggcatcaca cccgaggaag ccgtggccta tgccgataaa | 1020 |
| ctggacccca acttcgaacc gggtcgcctc accatggttg cccgcatggg tcatgacaag | 1080 |
| gtccgttccg tgctccccgg tgtcatccag gctgtggagg cttccggtca aaggtcatc | 1140 |
| tggcagtccg accccatgca cggcaacacc ttcaccgcct ccaatggtta caagacccgt | 1200 |

```
cacttcgaca aggtcatcga tgaggtgcag ggattcttcg aggtccaccg cgcactgggc    1260
acccacccgg gtggtatcca cattgaattc accggtgagg atgtcaccga atgccttggc    1320
ggtgcagagg acatcaccga cgtggatctg ccgggccgtt atgagtccgc ctgcgacccc    1380
cgtctgaaca cccagcagtc ccttgaactg tccttcctcg tggcggagat gctgcgtaat    1440
tag                                                                  1443
```

<210> SEQ ID NO 121
<211> LENGTH: 1395
<212> TYPE: DNA
<213> ORGANISM: Corynebacterium smegmatis

<400> SEQUENCE: 121

```
gtgaactgga ccgtcgacat ccccatcgac cagctaccgc ctttgccgcc gctgtccgac     60
gagcttcggc aacggctgga ttcggcactg gccaagccgg ctgtccagca gcccagctgg    120
gaccccgatg ccgccaaggc catgcgcacg gtcctggaga gcgtgccgcc ggtcaccgtg    180
ccgtcggaga tcgagaagct caagggtctg ctcgccgacg tcgcgcaggg caaggcgttc    240
ctgctgcagg gcggtgactg cgccgagacc ttcgtcgaca caccgaacc gcacatccgc     300 gccaacatcc gcacgctgct gcagatggcg gtggtgctga cctacggcgc gagcatgccg    360
gtggtgaagg ttgcccgcat cgccgggcag tacgccaagc cgcggcctc cgacgtcgac     420 gcgctgggc tcaagtccta ccgcggcgac atgatcaacg gtttcgcccc cgatgccgcg    480
gcccgcgaac atgatccgtc gcgtctggtg cgcgcgtacg ccaacgcgag cgcggcgatg    540
aacctgatgc gtgcgctgac ctcgtcgggg ctggcgtcgc tgcatctggt gcacgagtgg    600
aaccgcgaat tcgtccgcac gtcgcccgcc ggagcgcgtt acgaggcgct ggccggtgag    660
atcgaccgcg gcctgaactt catgtcggcc tgcggtgtcg ccgaccgcaa cctgcagacc    720
gccgagatct tcgcgagcca cgaggccctg gtgctcgact acgagcgcgc gatgctgcgc    780
ctgtccaacc cggccgagac cgacggtgcg gccaagctgt acgaccagtc ggcgcactac    840
ctgtggatcg gtgagcgcac acggcaactc gacggcgcgc acgtcgcgtt cgccgaggtg    900
atcgccaacc cgatcggcgt caagctcggt ccgaccacca cgccggaact cgccgtcgag    960
tacgtcgagc gccttgaccc gaacaacgaa ccgggccggc tgacgctcgt gacccgcatg   1020
ggcaacaaca aggtgcgcga cctgctgccg ccgatcatcg agaaggtgca ggccaccgga   1080
catcaggtga tctggcagtg cgacccgatg cacggcaaca cccatgagtc gtccacgggg   1140
tacaagacca ggcacttcga ccgcatcgtc gacgaggtgc agggctttt cgaggtgcac   1200 cacgcgctgg gcacgcatcc cggcggcatc cacgtcgaga tcaccggcga aaacgtcacc   1260
gaatgtctcg gtgggcaca ggacatttcg gattccgacc tggccggccg ctacgagacc   1320
gcgtgcgatc cgcgcctcaa cacccagcag agcctggaac tcgcgttctt ggtcgcggag   1380
atgctccgcg attag                                                    1395
```

<210> SEQ ID NO 122
<211> LENGTH: 1386
<212> TYPE: DNA
<213> ORGANISM: Rhodococcus opacus

<400> SEQUENCE: 122

```
gtgaactgga ctgtcgacgt gccgatcgac cgcttgcccg aactcccgcc gctgcccacc     60
gagatgcgtg agcgcctcga cgcagcgctg gccaagcccg ctgcccagca gccgcaatgg    120
```

```
                                                               -continued cccgaaggtc aggccgccgc gatgcggacc gtcctcgaga gcgtgccccc catcacggtg      180
gccagcgagg tcgtggccct gcaggagaag ctcgcccagg tcgcgcgcgg cgaggcgttc      240
ctcctccagg gcggtgactg cgccgagacg ttcgcggaca acaccgagcc gcacatcaag      300
ggcaacatcc gcaccctgct gcagatggcc gtcgtcctga cgtacggcgc gagcctgccc      360
gtcgtcaagg tcgcgcgcat cgccggtcag tacgcgaagc cgcggtcgtc caacgtcgac      420
gccctgggcc tgcagtccta ccgcggcgac atgatcaact ccctcgtcgc ggacgaggcc      480
gtgcgcgccc acgacccgtc gcggctcgtg cgggcgtacg cgaacgccag cgccgcgatg      540
aacctggtcc gcgcactcac cggcgcgggc atggccgacc tgcacaaggt gcacgactgg      600
aaccgcgaat tcgtgtcgtc gtcgccgccc ggggcccggt acgaggcgct cgccgcggag      660
atcgaccgcg ggctgcagtt catgaacgcc tgcggtgtca ccgatcccag cctgcatcac      720
gcccagatct tcgccagcca cgaggcgctc gtcctcgact acgagcgcgc gatgctgcgc      780
ctcgacaacg acgacgacca cgccaagctg tacgacctgt ccgcccactt cctgtggatc      840
ggcgaccgca cccgtcagct cgacggagcg cacatcgcgt tcgccgaact cgtgtcgaac      900
ccgatcggcc tgaagatcgg accgagcacc accccggaga tggcggtcga atacgtcgaa      960
cgcctcgacc ccaccaacaa gccgggccgg ctcacgctga tctcgcgcat gggcaacaac     1020
aaggtgcgcg acctgctgcc gcccatcatc gagaaggtgc aggccaccgg tcaccaggtg     1080
atctggcagt gcgacccgat gcacggcaac acgcacgagg cgtccaccgg ctacaagacc     1140
cgccacttcg accgcatcgt cgacgaggtc cagggattct tcgaggtcca caatggtctc     1200
ggcacctacc cgggcggcat ccacgtcgaa ctcaccggtg agaacgtcac cgaatgcctc     1260
ggcggcgcgc aggacatctc cgacctcgac ctgtccggtc gctacgagac ggcgtgcgac     1320
ccccgcctca acacccagca gtcgctggaa ctggcgttcc tcgtcgcgga gatgctgcgc     1380
ggctga                                                              1386
```

CORYNEFORM BACTERIUM TRANSFORMANT AND PROCESS FOR PRODUCING PHENOL USING THE SAME

TECHNICAL FIELD

The present invention relates to a technique for producing phenol. In more detail, the present invention relates to a coryneform bacterium transformant constructed by specific gene recombination and thereby provided with a phenol-producing function, and relates to an efficient phenol-producing process using the transformant.

BACKGROUND ART

Against the backdrop of global warming and exhaustion of fossil resources, production of chemical products using renewable resources, along with production of biofuels, is recognized as an emerging industry, biorefinery, which is an important means for realizing a low-carbon society, and has attracted keen attention.

However, production of biophenol using renewable resources is less productive as compared to production of lactic acid or ethanol because the metabolic reaction from a raw material saccharide consists of a great many steps. In addition, for the reasons that produced phenol inhibits bacterial proliferation and that phenol is cytotoxic, industrial production of phenol has been considered to be impossible.

Important use of phenol is phenol resins. A phenol resin, which is produced by addition condensation of phenol and aldehyde, is one of the oldest plastics, and with its properties including excellent heat resistance and durability, is used for various purposes, such as an alternative automotive material to metal, a semiconductor seal material, and a circuit board even today. Due to extremely high reactivity of phenol and aldehyde as raw materials and to the complicated three-dimensional network structure of resulting phenol resin polymers, precise structural designing and development into nanomaterials thereof had been considered difficult and so had been application to high-value-added use. However, in recent years, the theory of physical-properties of polymers and the simulation thereof have rapidly developed, and therefore it has gradually become possible to create highly functional materials from phenol resins by refining the network structure. Under the circumstances, the phenol resin production in Japan is also increasing year by year.

The currently employed industrial production process of phenol (cumene process) is a typical energy-consumptive process in the chemical industry using petroleum-derived benzene and propylene as raw materials, and requiring great amounts of solvent and thermal energy. Therefore, in the light of global environment conservation and greenhouse gas reduction, there is an urgent need to develop an environment-conscious, energy saving process that allows production of phenol from renewable resources and can reduce carbon dioxide emissions and waste products, that is, to establish biophenol production technologies.

There have not been reported phenol-producing bacteria in nature so far.

Also, there have not been known recombinant bacteria-based phenol-producing technologies to achieve a practically sufficient phenol productivity.

SUMMARY OF INVENTION

Technical Problem

An object of the present invention is to provide a microorganism capable of efficiently producing phenol from a saccharide, and a process for efficiently producing phenol from a saccharide.

Solution to Problem

The present inventors have wholeheartedly carried out investigations in order to achieve the object described above and obtained the following findings.
(i) A transformant constructed by transferring a chorismate-pyruvate lyase gene and a 4-hydroxybenzoate decarboxylase gene into a coryneform bacterium can efficiently produce phenol.
(ii) The transformant can further efficiently produce phenol in the case where the 4-hydroxybenzoate hydroxylase gene on the chromosome of the coryneform bacterium as the host has a disruption or deletion.
(iii) The transformant further efficiently produces phenol in the case where the 3-deoxy-D-arabinoheptulosonate 7-phosphate (DAHP) synthetase gene is more highly expressed as compared to the gene expression level before transformation.
(iv) The transformant has a particularly higher phenol productivity when proliferation is substantially inhibited in a reaction mixture under reducing conditions.

The present invention, which has been completed based on the above-mentioned findings, provides the following transformant and process for producing phenol.
[1] A phenol-producing transformant constructed by transferring a gene which encodes an enzyme having chorismate-pyruvate lyase activity and a gene which encodes an enzyme having 4-hydroxybenzoate decarboxylase activity into a coryneform bacterium as a host.
[2] The transformant of the above [1], wherein the gene which encodes an enzyme having chorismate-pyruvate lyase activity is a gene derived from *Escherichia coli*; a gene derived from *Pseudomonas putida*; a gene derived from *Acinetobacter baumannii*; a gene derived from *Azotobacter vinelandii*; a gene derived from *Chromohalobacter salexigens*; a gene derived from members of the genus *Citrobacter*, such as *Citrobacter koseri* and *Citrobacter youngae*; a gene derived from *Enterobacter cloacae*; a gene derived from *Marinobacter aquaeolei*; a gene derived from *Marinomonas mediterranea*; a gene derived from *Pantoea ananatis*; a gene derived from *Pseudoalteromonas haloplanktis*; a gene derived from *Ralstonia eutropha*; a gene derived from *Shewanella putrefaciens*; or a gene derived from *Thiobacillus denitrificans*.
[3] The transformant of the above [1], wherein the gene which encodes an enzyme having 4-hydroxybenzoate decarboxylase activity is a gene derived from *Bacillus subtilis*, a gene derived from *Bacillus atrophaeus*, a gene derived from *Bacillus subtilis* subsp. *spizizenii*, a gene derived from *Citrobacter koseri*, a gene derived from *Enterobacter aerogenes*, a gene derived from *Enterobacter cloacae*, a gene derived from *Enterobacter hormaechei*, a gene derived from *Enterobacter sakazakii*, a gene derived from *Escherichia coli*, a gene derived from *Escherichia fergusonii*, a gene derived from *Paenibacillus polymyxa*, or a gene derived from *Pantoea ananatis*.
[4] The transformant of the above [1], wherein the gene which encodes an enzyme having chorismate-pyruvate lyase activity is the DNA of the following (a) or (b).

(a) a DNA consisting of the base sequence of SEQ ID NO: 31, SEQ ID NO: 34, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, or SEQ ID NO: 93
(b) a DNA which hybridizes to a DNA consisting of a complementary base sequence of any of the DNAs of (a) under stringent conditions and which encodes a polypeptide having chorismate-pyruvate lyase activity

[5] The transformant of the above [1], wherein the gene which encodes an enzyme having 4-hydroxybenzoate decarboxylase activity is the DNA of the following (c) or (d).
(c) a DNA consisting of the base sequence of SEQ ID NO: 37, SEQ ID NO: 44, SEQ ID NO: 47, SEQ ID NO: 50, SEQ ID NO: 53, SEQ ID NO: 56, SEQ ID NO: 59, SEQ ID NO: 62, SEQ ID NO: 65, NO: 68, SEQ ID NO: 71, or SEQ ID NO: 74
(d) a DNA which hybridizes to a DNA consisting of a complementary base sequence of any of the DNAs of (c) under stringent conditions and which encodes a polypeptide having 4-hydroxybenzoate decarboxylase activity

[6] The transformant of any one of the above [1] to [5], wherein the coryneform bacterium as the host is a coryneform bacterium in which a gene which encodes an enzyme having 4-hydroxybenzoate hydroxylase activity on the chromosome is disrupted or deleted.

[7] The transformant of any one of the above [1] to [6], wherein the coryneform bacterium as the host is a coryneform bacterium in which a gene which encodes an enzyme having phenol 2-monooxygenase activity on the chromosome is disrupted or deleted.

[8] The transformant of any one of the above [1] to [7], wherein a gene which encodes an enzyme having 3-deoxy-D-arabino-heptulosonate 7-phosphate (DAHP) synthase activity is highly expressed in the coryneform bacterium as the host.

[9] The transformant of any one of the above [1] to [8], wherein the coryneform bacterium as the host is *Corynebacterium glutamicum*.

[10] The transformant of any one of the above [1] to [5], wherein the coryneform bacterium as the host is *Corynebacterium glutamicum* R (FERM BP-18976), ATCC13032, or ATCC13869.

[11] The transformant of any one of the above [1] to [5], wherein the coryneform bacterium as the host is a strain of *Corynebacterium glutamicum* R (FERM BP-18976), ATCC13032, or ATCC13869 in which a gene which encodes an enzyme having 4-hydroxybenzoate hydroxylase activity on the chromosome is disrupted or deleted.

[12] The transformant of any one of the above [1] to [5], wherein the coryneform bacterium as the host is a strain of *Corynebacterium glutamicum* R (FERM BP-18976), ATCC13032, or ATCC13869 in which a gene which encodes an enzyme having phenol 2-monooxygenase activity on the chromosome is disrupted or deleted.

[13] The transformant of anyone of the above [1] to [5], wherein the coryneform bacterium as the host is a strain of *Corynebacterium glutamicum* R (FERM BP-18976), ATCC13032, or ATCC13869 in which a gene which encodes an enzyme having 3-deoxy-D-arabino-heptulosonate 7-phosphate (DAHP) synthase activity is highly expressed.

[14] *Corynebacterium glutamicum* transformant PHE18 (Accession Number: NITE BP-995), PHE11, PHE12, PHE13, PHE14, PHE15, PHE16, PHE17, PHE19-1, PHE19-2, PHE19-3, PHE19-4, PHE19-5, PHE19-6, PHE19-7, PHE19-8, PHE19-9, PHE19-10, PHE19-11, PHE19-12, PHE20-1, PHE20-2, PHE20-3, PHE20-4, PHE20-5, PHE20-6, PHE20-7, PHE20-8, PHE20-9, PHE20-10, PHE20-11, PHE20-12, PHE20-13, or PHE20-14.

[15] A process for producing phenol, which comprises a step of allowing the transformant of any one of the above [1] to [14] to react in a reaction mixture containing a saccharide under reducing conditions, and a step of collecting phenol from the reaction mixture.

[16] The process of the above [15], wherein the transformant does not substantially proliferate in the reaction step.

[17] The process of the above [15] or [16], wherein the oxidation-reduction potential of the reaction mixture under reducing conditions is −200 mV to −500 mV.

[18] The process of any one of the above [15] to [17], wherein the saccharide is selected from the group consisting of glucose, fructose, mannose, xylose, arabinose, galactose, sucrose, maltose, lactose, cellobiose, xylobiose, trehalose, and mannitol.

Advantageous Effects of Invention

With the use of the transformant of the present invention, phenol can be efficiently produced from a saccharide.

Generally, growth of microorganisms is inhibited by a solvent, such as a phenol, because of its cytotoxicity, and therefore phenol production with the use of microorganisms was difficult. According to the process of the present invention, however, phenol production with the use of microorganisms can be achieved with a practically sufficient efficiency.

DESCRIPTION OF EMBODIMENTS

Figure 1:
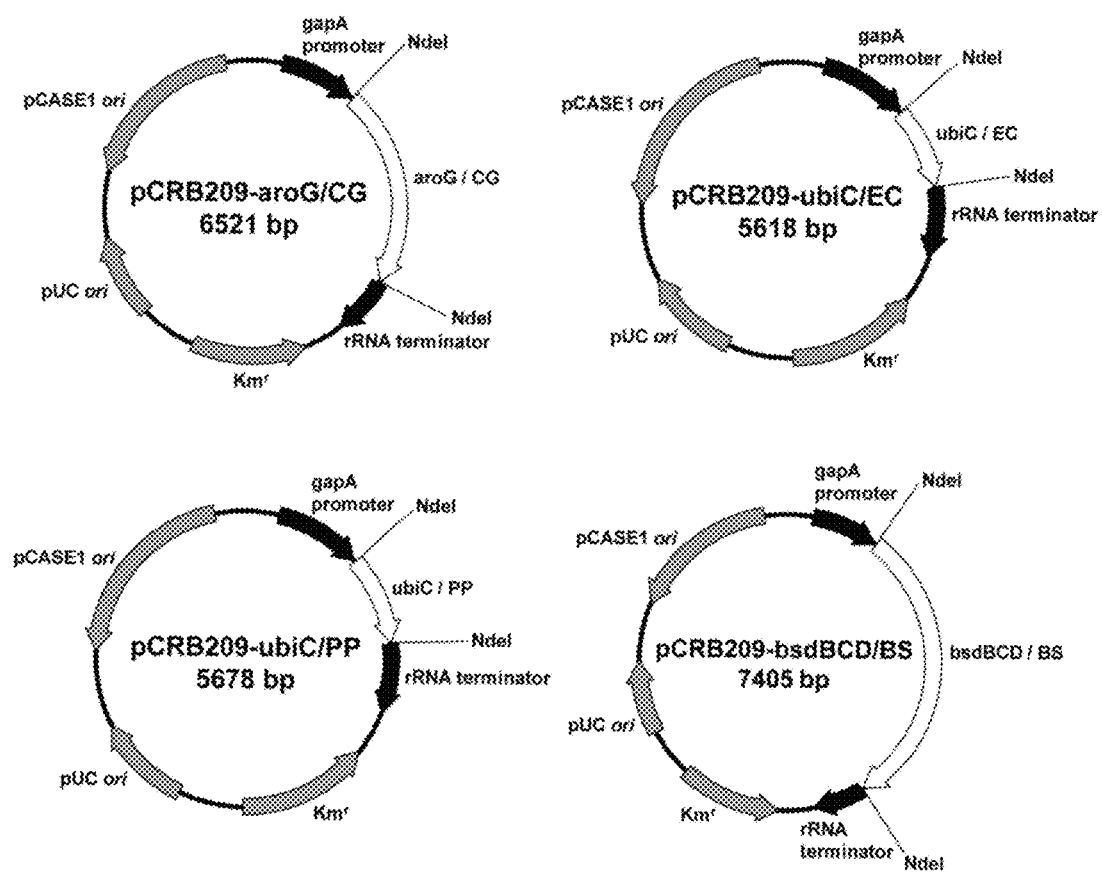
FIG. 1 shows the construct of various plasmids used in Examples.

Hereinafter, the present invention will be described in detail.

(I) Phenol-Producing Transformant

The transformant of the present invention capable of producing phenol is a transformant constructed by transferring a gene which encodes an enzyme having chorismate-pyruvate lyase activity and a gene which encodes an enzyme having 4-hydroxybenzoate decarboxylase activity into a coryneform bacterium as a host.

Host

The coryneform bacterium is a group of microorganisms defined in Bergey's Manual of Determinative Bacteriology, Vol. 8, 599 (1974), and is not particularly limited as long as it proliferates under normal aerobic conditions.

The specific examples include *Corynebacterium, Brevibacterium, Arthrobacter, Mycobacterium* and *Micrococcus*. Among the coryneform bacteria, *Corynebacterium* is preferred.

Examples of the *Corynebacterium* include *Corynebacterium glutamicum, Corynebacterium efficiens, Corynebacte-*

*rium ammoniagenes, Corynebacterium halotolerance,* and *Corynebacterium alkanolyticum.*

Inter alia, *Corynebacterium glutamicum* is preferred for safety and high phenol production. Examples of preferred strains include *Corynebacterium glutamicum* R (FERM P-18976), ATCC13032, ATCC13869, ATCC13058, ATCC13059, ATCC13060, ATCC13232, ATCC13286, ATCC13287, ATCC13655, ATCC13745, ATCC13746, ATCC13761, ATCC14020, ATCC31831, MJ-233 (FERM BP-1497), and MJ-233AB-41 (FERM BP-1498). Inter alia, strains R (FERM P-18976), ATCC13032, and ATCC13869 are preferred.

According to molecular biological classification, names of some species of coryneform bacteria, such as *Brevibacterium flavum, Brevibacterium lactofermentum, Brevibacterium divaricatum,* and *Corynebacterium lilium* are standardized to *Corynebacterium glutamicum* (Liebl, W. et al., Transfer of *Brevibacterium divaricatum* DSM 20297T, "*Brevibacterium flavum*" DSM 20411, "*Brevibacterium lactofermentum*" DSM 20412 and DSM 1412, and *Corynebacterium glutamicum* and their distinction by rRNA gene restriction patterns. Int. J. Syst. Bacteriol. 41: 255-260. (1991); and Kazuo Komagata et al., "Classification of the coryneform group of bacteria", Fermentation and industry, 45: 944-963 (1987)).

*Brevibacterium lactofermentum* ATCC13869, *Brevibacterium flavum* MJ-233 (FERM BP-1497) and MJ-233AB-41 (FERM BP-1498), etc. of the old classification are also suitable as *Corynebacterium glutamicum*.

Examples of the *Brevibacterium* include *Brevibacterium ammoniagenes* (for example, ATCC6872).

Examples of the *Arthrobacter* include *Arthrobacter globiformis* (for example, ATCC8010, ATCC4336, ATCC21056, ATCC31250, ATCC31738 and ATCC35698).

Examples of the *Mycobacterium* include *Mycobacterium bovis* (for example, ATCC19210 and ATCC27289).

Examples of the *Micrococcus* include *Micrococcus freudenreichii* (for example, NO. 239 (FERM P-13221)), *Micrococcus leuteus* (for example, NO. 240 (FERM P-13222)), *Micrococcus ureae* (for example, IAM1010), and *Micrococcus roseus* (for example, IFO3764).

The coryneform bacteria may be, let alone a wild strain, a mutant thereof or an artificial recombinant thereof. Examples thereof include disruptants in which a gene of lactate dehydrogenase, phosphoenolpyruvate carboxylase, or malate dehydrogenase is disrupted. Using such a disruptant as a host can improve phenol productivity and reduce production of by-products.

Inter alia, preferred is a disruptant in which a lactate dehydrogenase gene is disrupted. In the disruptant, the lactate dehydrogenase gene is disrupted and the metabolic pathway from pyruvic acid to lactic acid is blocked. Inter alia, especially preferred is a disruptant of *Corynebacterium glutamicum* R (FERM P-18976) strain in which the lactate dehydrogenase gene is disrupted.

Such a disruptant can be prepared based on a conventional gene engineering process. Such a lactate dehydrogenase disruptant and the preparation process thereof are described in WO 2005/010182 A1.

Chorismate-Pyruvate Lyase Gene (ubiC)

Chorismate-pyruvate lyase is an enzyme that catalyzes a reaction in which 4-hydroxybenzoate is produced by elimination of pyruvic acid from chorismate.

The gene which encodes an enzyme having chorismate-pyruvate lyase activity may be of any origin without particular limitation, and preferred examples thereof include a gene derived from *Escherichia coli*; a gene derived from *Pseudomonas putida*; a gene derived from *Acinetobacter baumannii*; a gene derived from *Azotobacter vinelandii*; a gene derived from *Chromohalobacter salexigens*; a gene derived from members of the genus *Citrobacter*, such as *Citrobacter koseri* and *Citrobacter youngae*; a gene derived from *Enterobacter cloacae*; a gene derived from *Marinobacter aquaeolei*; a gene derived from *Marinomonas mediterranea*; a gene derived from *Pantoea ananatis*; a gene derived from *Pseudoalteromonas haloplanktis*; a gene derived from *Ralstonia eutropha*; a gene derived from *Shewanella putrefaciens*; and a gene derived from *Thiobacillus denitrificans*. More preferred is a gene derived from *Pseudomonas putida*.

Examples of the chorismate-pyruvate lyase gene derived from *Escherichia coli* include the DNA consisting of the base sequence of SEQ ID NO: 31, examples of the chorismate-pyruvate lyase gene derived from *Pseudomonas putida* include the DNA consisting of the base sequence of SEQ ID NO: 34, examples of the chorismate-pyruvate lyase gene derived from *Acinetobacter baumannii* include the DNA consisting of the base sequence of SEQ ID NO: 81, examples of the chorismate-pyruvate lyase gene derived from *Azotobacter vinelandii* include the DNA consisting of the base sequence of SEQ ID NO: 82, examples of the chorismate-pyruvate lyase gene derived from *Chromohalobacter salexigens* include the DNA consisting of the base sequence of SEQ ID NO: 83, examples of the chorismate-pyruvate lyase gene derived from *Citrobacter koseri* include the DNA consisting of the base sequence of SEQ ID NO: 84, examples of the chorismate-pyruvate lyase gene derived from *Citrobacter youngae* include the DNA consisting of the base sequence of SEQ ID NO: 85, examples of the chorismate-pyruvate lyase gene derived from *Enterobacter cloacae* include the DNA consisting of the base sequence of SEQ ID NO: 86, examples of the chorismate-pyruvate lyase gene derived from *Marinobacter aquaeolei* include the DNA consisting of the base sequence of SEQ ID NO: 87, examples of the chorismate-pyruvate lyase gene derived from *Marinomonas mediterranea* include the DNA consisting of the base sequence of SEQ ID NO: 88, examples of the chorismate-pyruvate lyase gene derived from *Pantoea ananatis* include the DNA consisting of the base sequence of SEQ ID NO: 89, examples of the chorismate-pyruvate lyase gene derived from *Pseudoalteromonas haloplanktis* include the DNA consisting of the base sequence of SEQ ID NO: 90, examples of the chorismate-pyruvate lyase gene derived from *Ralstonia eutropha* include the DNA consisting of the base sequence of SEQ ID NO: 91, examples of the chorismate-pyruvate lyase gene derived from *Shewanella putrefaciens* include the DNA consisting of the base sequence of SEQ ID NO: 92, and examples of the chorismate-pyruvate lyase gene derived from *Thiobacillus denitrificans* include the DNA consisting of the base sequence of SEQ ID NO: 93.

In the present invention, a DNA which hybridizes to a DNA consisting of a complementary base sequence of the base sequence of SEQ ID NO: 31, 34, 81, 82, 83, 84, 85, 86, 87, 88, 89, 90, 91, 92, or 93 under stringent conditions and which encodes a polypeptide having chorismate-pyruvate lyase activity can also be used.

The "stringent conditions" as used herein means general conditions, for example, the conditions described in Molecular Cloning, A Laboratory Manual, Second edition, 1989, Vol. 2, p. 11. 45. It means, in particular, conditions where hybridization occurs at a temperature 5 to 10° C. below the melting temperature (Tm) of a perfect hybrid.

The chorismate-pyruvate lyase activity can be measured by the method described in Journal of Bacteriology, 174, 5309-

5316 (1992) "Materials and Methods". Briefly, by adding a test enzyme to a liquid for testing, a reaction mixture containing 50 mM tris-HCL (pH 7.5), 5 mM EDTA, 10 mM β-mercaptoethanol, 60 μM chorismic acid, and the enzyme is prepared, and then the slope of the absorbance at 240 nm (initial rate) is determined. The same measurement is performed using a system without the addition of chorismic acid to obtain a background value. The difference between the two measured values will be regarded as the chorismate-pyruvate lyase activity.

In the present invention, a DNA consisting of a base sequence which has 90% or more, preferably 95% or more, more preferably 98% or more homology with the base sequence of SEQ ID NO: 31, 34, 81, 82, 83, 84, 85, 86, 87, 88, 89, 90, 91, 92, or 93 and which encodes a polypeptide having chorismate-pyruvate lyase activity can also be used.

The base sequence homology was calculated using GENE-TYX Ver. 8 (made by Genetyx).

The homologue of the DNA consisting of the base sequence of SEQ ID NO: 31, 34, 81, 82, 83, 84, 85, 86, 87, 88, 89, 90, 91, 92, or 93 can be selected from a DNA library of a different species by, for example, PCR or hybridization using a primer or a probe designed based on these base sequences, according to a conventional method, and as a result, a DNA which encodes a polypeptide having chorismate-pyruvate lyase activity can be obtained with a high probability.

4-Hydroxybenzoate Decarboxylase Gene (bsdBCD or Dca)

4-Hydroxybenzoate decarboxylase is an enzyme that catalyzes a phenol-producing reaction in which 4-hydroxybenzoate is decarboxylated.

The gene which encodes an enzyme having 4-hydroxybenzoate decarboxylase activity may be of any origin without particular limitation, and examples thereof include genes derived from members of the genus *Bacillus*, such as *Bacillus subtilis*, *Bacillus megaterium*, *Bacillus licheniformis*, *Bacillus atrophaeus*, and *Bacillus subtilis* subsp. *spizizenii*; *Citrobacter koseri*; members of the genus *Enterobacter*, such as *Enterobacter aerogenes*, *Enterobacter cloacae*, *Enterobacter hormaechei*, and *Enterobacter sakazakii*; members of the genus *Escherichia*, such as *Escherichia coli* and *Escherichia fergusonii*; *Paenibacillus polymyxa*; and *Pantoea ananatis*. Inter alia, preferred is a gene derived from members of the genus *Bacillus*, in particular *Bacillus subtilis*; members of the genus *Enterobacter*, in particular *Enterobacter cloacae*; or members of the genus *Escherichia*, in particular *Escherichia coli*.

A gene which encodes an enzyme having 4-hydroxybenzoate decarboxylase activity is called by an abbreviated name that varies according to the origin. For example, a 4-hydroxybenzoate decarboxylase gene derived from *Bacillus subtilis* is called by an abbreviation bsdBCD. Herein, a 4-hydroxybenzoate decarboxylase gene may be called by an abbreviation "dca" regardless of the origin.

Examples of the 4-hydroxybenzoate decarboxylase gene derived from *Bacillus subtilis* include the DNA consisting of the base sequence of SEQ ID NO: 37, examples of the 4-hydroxybenzoate decarboxylase gene derived from *Bacillus atrophaeus* include the DNA consisting of the base sequence of SEQ ID NO: 44, examples of the 4-hydroxybenzoate decarboxylase gene derived from *Bacillus subtilis* subsp. *spizizenii* include the DNA consisting of the base sequence of SEQ ID NO: 47, examples of the 4-hydroxybenzoate decarboxylase gene derived from *Citrobacter koseri* include the DNA consisting of the base sequence of SEQ ID NO: 50, examples of the 4-hydroxybenzoate decarboxylase gene derived from *Enterobacter aerogenes* include the DNA consisting of the base sequence of SEQ ID NO: 53, examples of the 4-hydroxybenzoate decarboxylase gene derived from *Enterobacter cloacae* include the DNA consisting of the base sequence of SEQ ID NO: 56, examples of the 4-hydroxybenzoate decarboxylase gene derived from *Enterobacter hormaechei* include the DNA consisting of the base sequence of SEQ ID NO: 59, examples of the 4-hydroxybenzoate decarboxylase gene derived from *Enterobacter sakazakii* include the DNA consisting of the base sequence of SEQ ID NO: 62, examples of the 4-hydroxybenzoate decarboxylase gene derived from *Escherichia coli* include the DNA consisting of the base sequence of SEQ ID NO: 65, examples of the 4-hydroxybenzoate decarboxylase gene derived from *Escherichia fergusonii* include the DNA consisting of the base sequence of SEQ ID NO: 68, examples of the 4-hydroxybenzoate decarboxylase gene derived from *Paenibacillus polymyxa* include the DNA consisting of the base sequence of SEQ ID NO: 71, and examples of the 4-hydroxybenzoate decarboxylase gene derived from *Pantoea ananatis* include the DNA consisting of the base sequence of SEQ ID NO: 74.

In the present invention, a DNA which hybridizes to a DNA consisting of a complementary base sequence of the base sequence of SEQ ID NO: 37, 44, 47, 50, 53, 56, 59, 62, 65, 68, 71, or 74 under stringent conditions and which encodes a polypeptide having 4-hydroxybenzoate decarboxylase activity can also be used.

The 4-hydroxybenzoate decarboxylase activity can be measured by the method described in Genomics, 86, 342-351 (2005) "Materials and Methods". Briefly, by adding a test enzyme to a liquid for testing, a reaction mixture containing 100 mM MES (pH 6.0), 1 mM DTT, 5 mM 4-hydroxybenzoate, and the enzyme is prepared, and then the slope of the absorbance at 270 nm (initial rate) is determined. The same measurement is performed using a system without the addition of 4-hydroxybenzoate to obtain a background value. The difference between the two measured values will be regarded as the 4-hydroxybenzoate decarboxylase activity.

In the present invention, a DNA consisting of a base sequence which has 90% or more, preferably 95% or more, more preferably 98% or more homology with the base sequence of SEQ ID NO: 37, 44, 47, 50, 53, 56, 59, 62, 65, 68, 71, or 74 and which encodes a polypeptide having 4-hydroxybenzoate decarboxylase activity can also be used.

The homologue of the DNA consisting of the base sequence of SEQ ID NO: 37, 44, 47, 50, 53, 56, 59, 62, 65, 68, 71, or 74 can be obtained by the method described above.

Construction of Vector for Transformation

The DNA which encodes chorismate-pyruvate lyase and the DNA which encodes 4-hydroxybenzoate decarboxylase are separately amplified by PCR and then cloned into a suitable vector which is replicable in a host.

The plasmid vector may be any plasmid vector as long as it comprises a gene responsible for autonomously replicating function in a coryneform bacterium. Specific examples of the plasmid vector include pAM330 derived from *Brevibacterium lactofermentum* 2256 (JP 58-67699 A; Miwa, K. et al., Cryptic plasmids in glutamic acid-producing bacteria. Agric. Biol. Chem. 48:2901-2903 (1984); and Yamaguchi, R. et al., Determination of the complete nucleotide sequence of the *Brevibacterium lactofermentum* plasmid pAM330 and the analysis of its genetic information. Nucleic Acids Symp. Ser. 16:265-267 (1985)); pHM1519 derived from *Corynebacterium glutamicum* ATCC13058 (Miwa, K. et al., Cryptic plasmids in glutamic acid-producing bacteria. Agric. Biol. Chem. 48:2901-2903 (1984)) and pCRY30 derived from the same (Kurusu, Y. et al., Identification of plasmid partition function in coryneform bacteria. Appl. Environ. Microbiol. 57:759-764 (1991)); pCG4 derived from *Corynebacterium*

*glutamicum* T250 (JP 57-183799 A; and Katsumata, R. et al., Protoplast transformation of glutamate-producing bacteria with plasmid DNA. J. Bacteriol., 159:306-311 (1984)), pAG1, pAG3, pAG14 and pAG50 derived from the same (JP 62-166890 A), and pEK0, pEC5 and pEKEx1 derived from the same (Eikmanns, B. J. et al., A family of *Corynebacterium glutamicum/Escherichia coli* shuttle vectors for cloning, controlled gene expression, and promoter probing. Gene, 102: 93-98 (1991)); etc.

Examples of a preferred promoter include promoter PgapA as a promoter of the glyceraldehyde-3-phosphate dehydrogenase A gene (gapA), promoter Pmdh as a promoter of the malate dehydrogenase gene (mdh), and promoter PldhA as a promoter of lactate dehydrogenase A gene (ldhA), all of which are derived from *Corynebacterium glutamicum* R, and inter alia, PgapA is preferred.

Examples of a preferred terminator include terminator rrnB T1T2 of *Escherichia coli* rRNA operon, terminator trpA of *Escherichia coli*, and terminator trp of *Brevibacterium lactofermentum*, and inter alia, terminator rrnB T1T2 is preferred.

Transformation

As a method of transformation, any publicly known method can be used without limitation. Examples of such a known method include the calcium chloride/rubidium chloride method, the calcium phosphate method, DEAE-dextran transfection, and electroporation. Inter alia, preferred for a coryneform bacterium is electroporation, which can be performed by a known method (Kurusu, Y. et al., Electroporation-transformation system for Coryneform bacteria by auxotrophic complementation., Agric. Biol. Chem. 54:443-447 (1990); and Vertes A. A. et al., Presence of mrr- and mcr-like restriction systems in Coryneform bacteria. Res. Microbiol. 144:181-185 (1993)).

The transformant is cultured using a culture medium usually used for culture of microorganisms. The culture medium may be a natural or synthetic medium containing a carbon source, a nitrogen source, inorganic salts, other nutritional substances, etc.

Examples of the carbon source include carbohydrates and sugar alcohols such as glucose, fructose, sucrose, mannose, maltose, mannitol, xylose, arabinose, galactose, starch, molasses, sorbitol and glycerol; organic acids such as acetic acid, citric acid, lactic acid, fumaric acid, maleic acid and gluconic acid; and alcohols such as ethanol and propanol. Hydrocarbons, such as normal paraffin, etc. may also be used as desired. These carbon sources may be used alone or as a mixture of two or more thereof. The concentration of these carbon sources in the culture medium is usually about 0.1 to 10 w/v %.

Examples of the nitrogen source include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N—Z-amine, protein hydrolysate, amino acid, etc. may also be used. These nitrogen sources may be used alone or as a mixture of two or more thereof. The concentration of these nitrogen sources in the culture medium varies depending on the kind of the nitrogen compound, but is usually about 0.1 to 10 w/v %.

Examples of the inorganic salts include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. These inorganic salts may be used alone or as a mixture of two or more thereof. The concentration of the inorganic salts in the culture medium varies depending on the kind of the inorganic salts, but is usually about 0.01 to 1 w/v %

Examples of the nutritional substances include meat extract, peptone, polypeptone, yeast extract, dry yeast, corn steep liquor, skim milk powder, defatted soybean hydrochloric acid hydrolysate, and extract from animals, plants or microorganisms, and degradation products thereof. The concentration of the nutritional substances in the culture medium varies depending on the kind of the nutritional substances, but is usually about 0.1 to 10 w/v %. Further, vitamins may be added as needed. Examples of the vitamins include biotin, thiamine (vitamin B1), pyridoxine (vitamin B6), pantothenic acid, inositol, nicotinic acid, etc.

The pH of the culture medium is preferably about 5 to 8.

Examples of the preferable microbial culture medium include A medium (Inui, M. et al., Metabolic analysis of *Corynebacterium glutamicum* during lactate and succinate productions under oxygen deprivation conditions. J. Mol. Microbiol. Biotechnol. 7:182-196 (2004)), BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)), etc.

The culture temperature is about 15 to 45° C., and the culture period is about 1 to 7 days.

Disruption or Deletion in Host Chromosomal Gene

In the coryneform bacterium as a host, the gene which encodes an enzyme having 4-hydroxybenzoate hydroxylase activity (pobA) on the chromosome preferably has a disruption or deletion for further efficient phenol production. In addition, in the coryneform bacterium as a host, the gene which encodes an enzyme having phenol 2-monooxygenase activity (poxF) on the chromosome preferably has a disruption or deletion for further efficient phenol production.

Particularly preferred is that both of pobA and poxF have a disruption or deletion.

Replacement of a gene on the chromosome with the corresponding gene having an disruption or deletion can be achieved by creating a gene with deletion mutation for not allowing production of a normally functioning enzyme protein, and transforming a bacterium with a DNA comprising the mutated gene for recombination in which the gene on the chromosome and the mutated gene are exchanged. An enzyme protein encoded by a gene having a disruption or deletion, even when produced, has a conformation different from that of the wild type, and has no or reduced function. The gene deletion or gene disruption by way of gene replacement through such homologous recombination has already been established, and examples thereof include a method using a plasmid containing a temperature sensitive replication origin or a plasmid capable of conjugal transfer, and a method using a suicide vector not having a replication origin that works in a host (U.S. Pat. No. 6,303,383 and JP 05-007491 A).

Specifically, by the method described in Example 1, a coryneform bacterium in which the 4-hydroxybenzoate hydroxylase gene (pobA) is disrupted or deleted can be obtained. In addition, in a similar way, a coryneform bacterium in which the phenol 2-monooxygenase gene (poxF) is disrupted or deleted can be obtained.

High Expression of Metabolic Gene

It is preferred that the 3-deoxy-D-arabino-heptulosonate 7-phosphate (DAHP) synthase gene (aroG) is expressed at a higher level in the coryneform bacterium as a host as compared with the original level in the host, i.e., the level in the wild type host. Such high expression is achieved by transformation via gene transfer or by increase in the number of copies of the desired gene(s) on the chromosome of the host.

Regarding the transformation, the DAHP synthetase gene may be the same or substantially same as that of the host, or of a different type. Preferably, the DAHP synthetase gene may be the same or substantially same as that of the host.

Examples of the DAHP synthetase gene derived from *Corynebacterium glutamicum* include the DNA consisting of the base sequence of SEQ ID NO: 28.

Examples of the DAHP synthetase gene derived from a different type of coryneform bacteria include a gene derived from *Corynebacterium efficiens* (SEQ ID NO: 120, DNA Data Bank of Japan: CE2073), a gene derived from *Mycobacterium smegmatis* (SEQ ID NO: 121, DNA Data Bank of Japan: MSMEG_4244), and a gene derived from *Rhodococcus opacus* (SEQ ID NO: 122, DNA Data Bank of Japan: ROP_08400).

Regarding the DAHP synthetase gene, examples of the "substantially same gene" include a DNA which encodes a polypeptide having 90% or more, preferably 95% or more, and more preferably 98% or more homology with the amino acid sequence of a polypeptide encoded by the gene, and having a DAHP synthetase activity. Regarding the DAHP synthetase gene, examples of the "substantially same gene" include a DNA which has 90% or more, preferably 95% or more, and more preferably 98% or more homology with the gene, and which encodes a polypeptide having a DAHP synthetase activity.

The DAHP synthetase activity can be determined by the reaction of phosphoenolpyruvic acid and erythrose-4-phosphate as substrates followed by quantification of produced 3-deoxy-D-arabino-heptulosonate 7-phosphate (DAHP) by a chromogenic method with the use of thiobarbituric acid (Appl. Environ. Microbiol., 74: 5497-5503 (2008)).

To increase the number of copies of the DAHP synthetase gene on the chromosome of the host, multiple copies of the gene may be transferred onto the chromosomal DNA. To transfer multiple copies of a gene onto the chromosomal DNA of a microorganism, homologous recombination (Experiments in Molecular Genetics, Cold Spring Harbor Lab. (1972)) may be performed using, as a target, a sequence that exists as multiple copies on the chromosomal DNA. As the sequence that exists as multiple copies on the chromosomal DNA, a repetitive DNA or an inverted repeat that exists at the end of a transposon may be used. Also, as disclosed in JP 02-109985 A, it is feasible to transfer multiple copies of the desired gene with a transposon onto the chromosomal DNA. Alternatively, by a method using Mu phage (JP 02-109985 A), the desired gene may be transferred onto a host chromosome.

Substitution of an expression control sequence, such as a promoter, of the DAHP synthetase gene with a stronger one can also increase the expression of such a gene. For example, a tac promoter, a lac promoter, a trc promoter, a trp promoter, etc. are known as a strong promoter. Further, as disclosed in WO00/18935, it is also feasible to alter a promoter to a stronger one by substitution of a few bases in the promoter region of the gene. Examples of the evaluation method of the strength of a promoter and examples of such a promoter are described in a paper by Goldstein et al. "Prokaryotic promoters in biotechnology". Biotechnol. Annu. Rev., 1995, 1, 105-128, etc. Substitution of an expression control sequence can be performed in a similar way to the gene substitution with the use of a temperature sensitive plasmid, for example.

Further, it is known that substitution of a spacer between a ribosomal binding site (RBS) and an initiator codon, in particular substitution of a few nucleotides in a sequence immediately upstream of the initiator codon has a great influence on the efficiency of mRNA translation. Therefore, the alteration thereof can improve the amount of translation.

Examples of the method for the above-mentioned gene substitution include a method using a plasmid containing a temperature sensitive replication origin or a plasmid capable of conjugal transfer, and a method using a suicide vector not having a replication origin that works in a host (U.S. Pat. No. 6,303,383 and JP 05-007491 A).

(II) Process for Producing Phenol

Phenol can be produced by a process comprising a step of allowing the above-described transformant of the present invention to react in a reaction mixture containing a saccharide, and a step of collecting phenol from the reaction mixture.

Proliferation of Microorganism

Before the reaction, the transformant is preferably cultured and proliferated under aerobic conditions at about 25 to 38° C. for about 12 to 48 hours.

The culture medium used for aerobic culture of the transformant before the reaction may be a natural or synthetic medium containing a carbon source, a nitrogen source, inorganic salts, other nutritional substances, etc.

Examples of the carbon source that can be used include saccharides (monosaccharides such as glucose, fructose, mannose, xylose, arabinose, and galactose; disaccharides such as sucrose, maltose, lactose, cellobiose, xylobiose, and trehalose; polysaccharides such as starch; and molasses); sugar alcohols such as mannitol, sorbitol, xylitol, and glycerol; organic acids such as acetic acid, citric acid, lactic acid, fumaric acid, maleic acid and gluconic acid; alcohols such as ethanol and propanol; and hydrocarbons such as normal paraffin.

These carbon sources may be used alone or as a mixture of two or more thereof.

Examples of the nitrogen source that can be used include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N—Z-amine, protein hydrolysate, amino acid, etc. may also be used. These nitrogen sources may be used alone or as a mixture of two or more thereof. The concentration of these nitrogen sources in the culture medium varies depending on the kind of the nitrogen compound, but is usually about 0.1 to 10 w/v %.

Examples of the inorganic salts include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. These inorganic salts may be used alone or as a mixture of two or more thereof. The concentration of the inorganic salts in the culture medium varies depending on the kind of the inorganic salts, but is usually about 0.01 to 1 w/v %

Examples of the nutritional substances include meat extract, peptone, polypeptone, yeast extract, dry yeast, corn steep liquor, skim milk powder, defatted soybean hydrochloric acid hydrolysate, and extract from animals, plants or microorganisms, and degradation products thereof. The concentration of the nutritional substances in the culture medium varies depending on the kind of the nutritional substances, but is usually about 0.1 to 10 w/v %.

Further, vitamins may be added as needed. Examples of the vitamins include biotin, thiamine (vitamin B1), pyridoxine (vitamin B6), pantothenic acid, inositol, nicotinic acid, etc.

The pH of the culture medium is preferably about 6 to 8.

Specific examples of the preferable culture medium for coryneform bacteria include A medium (Inui, M. et al., Metabolic analysis of *Corynebacterium glutamicum* during lactate and succinate productions under oxygen deprivation conditions. J. Mol. Microbiol. Biotechnol. 7:182-196 (2004)), BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)), etc. Such a culture medium can be used after prepared so as to contain a saccharide at a concentration in the above-mentioned range.

Reaction Mixture

The reaction mixture may be a natural or synthetic medium containing a carbon source, a nitrogen source, inorganic salts, other nutritional substances, etc.

As the carbon source, a saccharide is used. Examples of the saccharide include monosaccharides such as glucose, fructose, mannose, xylose, arabinose, and galactose; disaccharides such as sucrose, maltose, lactose, cellobiose, xylobiose, and trehalose; polysaccharides such as starch; and molasses. Inter alia, a monosaccharide is preferred, and glucose is more preferred.

As the carbon source, besides saccharides, sugar alcohols such as mannitol, sorbitol, xylitol, and glycerol; organic acids such as acetic acid, citric acid, lactic acid, fumaric acid, maleic acid and gluconic acid; alcohols such as ethanol and propanol; and hydrocarbons such as normal paraffin can also be used.

These carbon sources may be used alone or as a mixture of two or more thereof.

The concentration of the saccharide in the reaction mixture is preferably about 1 to 20 w/v %, more preferably about 2 to 10 w/v %, and still more preferably about 2 to 5 w/v %.

The total concentration of the carbon sources including the saccharide in the reaction mixture is usually about 2 to 5 w/v %.

Examples of the nitrogen source that can be used include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N—Z-amine, protein hydrolysate, amino acid, etc. may also be used. These nitrogen sources may be used alone or as a mixture of two or more thereof. The concentration of these nitrogen sources in the reaction mixture varies depending on the kind of the nitrogen compound, but is usually about 0.1 to 10 w/v %.

Examples of the inorganic salts include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. These inorganic salts may be used alone or as a mixture of two or more thereof. The concentration of the inorganic salts in the reaction mixture varies depending on the kind of the inorganic salts, but is usually about 0.01 to 1 w/v %

Examples of the nutritional substances include meat extract, peptone, polypeptone, yeast extract, dry yeast, corn steep liquor, skim milk powder, defatted soybean hydrochloric acid hydrolysate, and extract from animals, plants or microorganisms, and degradation products thereof. The concentration of the nutritional substances in the reaction mixture varies depending on the kind of the nutritional substances, but is usually about 0.1 to 10 w/v %.

Further, vitamins may be added as needed. Examples of the vitamins include biotin, thiamine (vitamin B1), pyridoxine (vitamin B6), pantothenic acid, inositol, nicotinic acid, etc.

The pH of the reaction mixture is preferably about 6 to 8.

Specific examples of the preferable culture medium for coryneform bacteria include A medium and BT medium as described above. Such a culture medium can be used after prepared so as to contain a saccharide at a concentration in the above-mentioned range.

Reaction Conditions

The reaction temperature, that is, the temperature for keeping the transformant alive during the reaction is preferably about 20 to 50° C., and more preferably about 25 to 40° C. When the temperature is in the above range, phenol can be efficiently produced.

The reaction period is preferably about 1 to 7 days, and more preferably about 1 to 3 days.

The culture may be a batch process, a fed-batch process, or a continuous process. Inter alia, a batch process is preferred.

<Reducing Conditions>

The reaction may be performed under aerobic conditions or reducing conditions, but preferably is performed under reducing conditions. Under reducing conditions, coryneform bacteria do not substantially proliferate and can further efficiently produce phenol.

The "reducing conditions" is defined based on the oxidation-reduction potential of the reaction mixture. The oxidation-reduction potential of the reaction mixture is preferably about −200 mV to −500 mV, and more preferably about −250 mV to −500 mV.

The reducing conditions of the reaction mixture can be simply estimated with the use of resazurin indicator (in reducing conditions, decolorization from blue to colorless is observed). However, for precise measurement, a redox-potential meter (for example, ORP Electrodes made by BROADLEY JAMES) is used.

As a method of preparing a reaction mixture under reducing conditions, any publicly known method can be used without limitation. For example, as a liquid medium for preparation of the reaction mixture, an aqueous solution for a reaction mixture may be used instead of distilled water or the like. As reference for preparation of the aqueous solution for a reaction mixture, for example, the method for preparing a culture medium for strictly anaerobic microorganisms, such as sulfate-reducing microorganisms (Pfennig, N. et al.: The dissimilatory sulfate-reducing bacteria, In The Prokaryotes, A Handbook on Habitats, Isolation and Identification of Bacteria, Ed. by Starr, M. P. et al. Berlin, Springer Verlag, 926-940, 1981, or *Nogeikagaku Jikkensho*, Ed. by Kyoto Daigaku Nogakubu Nogeikagaku Kyoshitsu, Vol. 3, Sangyo Tosho, 1990, Issue 26) may be used, and such a method provides an aqueous solution under desired reducing conditions.

Specifically, by treating distilled water or the like with heat or under reduced pressure for removal of dissolved gases, an aqueous solution for a reaction mixture under reducing conditions can be obtained. In this case, for removal of dissolved gases, especially dissolved oxygen, distilled water or the like may be treated under reduced pressure of about 10 mmHg or less, preferably about 5 mmHg or less, more preferably about 3 mmHg or less, for about 1 to 60 minutes, preferably for about 5 to 40 minutes.

Alternatively, by adding a suitable reducing agent (for example, thioglycolic acid, ascorbic acid, cysteine hydrochloride, mercaptoacetic acid, thiol acetic acid, glutathione, sodium sulfide, etc.), an aqueous solution for a reaction mixture under reducing conditions can be prepared.

These methods may be suitably combined to prepare an effective aqueous solution for a reaction mixture under reducing conditions.

It is preferred to maintain the reducing conditions of the reaction mixture during the reaction. For maintenance of reducing conditions, it is preferred that oxygen from the outside of the reaction system is prevented to the utmost extent from entering the system. Specific examples of the method employed for this purpose include a method comprising encapsulating the reaction system with inert gas, such as nitrogen gas, carbon dioxide gas, etc. In some cases, for allowing the metabolic functions in the cells of the aerobic bacterium of the present invention to work effectively during the reaction, addition of a solution of various nutrients or a reagent solution for adjusting and maintaining the pH of the reaction system may be needed. In such a case, for more effective prevention of oxygen incorporation, it is effective to remove oxygen in the solutions to be added, in advance.

Collection of Phenol

Through the culture performed in the above manner, phenol is produced in the reaction mixture. Phenol can be collected by collecting the reaction mixture, and it is also feasible to isolate phenol from the reaction mixture by a known method. Examples of such a known method include distillation, the membrane permeation method, and the organic solvent extraction method.

EXAMPLES

Example 1

Cloning and Expression of Phenol-Producing Genes (1) Extraction of Chromosomal DNA from Microorganisms To extract chromosomal DNA from *Corynebacterium glutamicum* R (FERM P-18976), the bacterium was inoculated, with the use of a platinum loop, into A medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O+0.042\%$ (w/v) $MnSO_4.2H_2O$, 1 mL of 0.02% (w/v) biotin solution, 2 mL of 0.01% (w/v) thiamin solution, 2 g of yeast extract, and 7 g of vitamin assay casamino acid were dissolved in 1 L of distilled water), which was supplemented with 50% (w/v) glucose as a carbon source to a final concentration of 4%, and cultured with shaking at 33° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Escherichia coli* (K-12 MG1655), the bacterium was inoculated into LB Medium (10 g of tryptone, 5 g of yeast extract, and 5 g of NaCl were dissolved in 1 L of distilled water) with the use of a platinum loop, and cultured with shaking at 37° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Pseudomonas putida* (KT2440) ATCC 47054, the bacterium was inoculated into LB Medium (10 g of tryptone, 5 g of yeast extract, and 5 g of NaCl were dissolved in 1 L of distilled water) with the use of a platinum loop, and cultured with shaking at 37° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Acinetobacter baumannii* (JCM 6841), the bacterium was inoculated into JCM Medium No. 12 (5 g of peptone, 3 g of beef extract, and 5 g of NaCl were dissolved in 1 L of distilled water) with the use of a platinum loop, and cultured with shaking at 37° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Azotobacter vinelandii* (ATCC 9104), the bacterium was inoculated into NBRC Medium No. 805 (1 g of east extract, 5 g of mannitol, 0.7 g of $K_2HPO_4$, 0.1 g of $KH_2PO_4$, 0.2 g of $MgSO_4.7H_2O$, and 1 g of NaCl were dissolved in 1 L of distilled water) with the use of a platinum loop, and cultured with shaking at 30° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Chromohalobacter salexigens* (ATCC BAA-138), the bacterium was inoculated into Nutrient Broth with NaCl Medium (8 g of Nutrient Broth (made by Becton, Dickinson and Company, catalog No. 234000) and 100 g of NaCl were dissolved in 1 L of distilled water) with the use of a platinum loop, and cultured with shaking at 37° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Citrobacter youngae* (ATCC 29220), the bacterium was inoculated into Nutrient Broth Medium (8 g of Nutrient Broth (made by Becton, Dickinson and Company, catalog No. 234000) was dissolved in 1 L of distilled water) with the use of a platinum loop, and cultured with shaking at 37° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

The chromosomal DNA of *Marinobacter aquaeolei* ATCC 700491 (catalog No. 700491D-5) was obtained from American Type Culture Collection (ATCC).

To extract chromosomal DNA from *Marinomonas mediterranea* (NBRC 103028), the bacterium was inoculated into NBRC Medium No. 340 (37.4 g of Bacto Marine Broth 2216 (made by Becton, Dickinson and Company, catalog No. 279110) was dissolved in 1 L of distilled water) with the use of a platinum loop, and cultured with shaking at 25° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Pseudoalteromonas haloplanktis* (NBRC 102225), the bacterium was inoculated into NBRC Medium No. 340 (37.4 g of Bacto Marine Broth 2216 (made by Becton, Dickinson and Company, catalog No. 279110) was dissolved in 1 L of distilled water) with the use of a platinum loop, and cultured with shaking at 25° C. until the logarithmic growth phase. After the bacterial cells were collected, chromosomal DNA was recovered from the collected cells with the use of a DNA extraction kit (trade name:

GenomicPrep Cells and Tissue DNA Isolation Kit, made by Amersham) according to the instruction manual.

To extract chromosomal DNA from *Ralstonia eutropha* (IAM 12368), the bacterium was inoculated into Nutrient Broth Medium (8 g of Nutrient Broth (made by Becton, Dickinson and Company, catalog No. 234000) was dissolved in 1 L of distilled water) with the use of a platinum loop, and cultured with shaking at 26° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Shewanella putrefaciens* (JCM 20190), the bacterium was inoculated into Nutrient Broth Medium (8 g of Nutrient Broth (made by Becton, Dickinson and Company, catalog No. 234000) was dissolved in 1 L of distilled water) with the use of a platinum loop, and cultured with shaking at 25° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Thiobacillus denitrificans* (ATCC 25259, JCM 20190), the bacterium was inoculated into JCM Medium No. 91 (5 g of $KNO_3$ and 0.5 g of $NaHCO_3$ were dissolved in 1 L of S6 medium (1.8 g of $KH_2PO_4$, 1.2 g of $Na_2HPO_4$, 0.1 g of $(NH_4)_2SO_4$, 0.1 g of $MgSO_4.7H_2O$, 30 mg of $FeCl_3.6H_2O$, 30 mg of $MnSO_4.xH_2O$, 40 mg of $CaCl_2.2H_2O$, and 100 mL of 10% $Na_2S_2O_3$ solution were dissolved in 900 mL of distilled water)) with the use of a platinum loop, and cultured with shaking at 30° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Bacillus subtilis* NBRC 14144, the bacterium was inoculated into NBRC Medium No. 802 (10 g of polypeptone, 2 g of yeast extract, and 1 g of $MgSO_4.7H_2O$ were dissolved in 1 L of distilled water) with the use of a platinum loop, and cultured with shaking at 37° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Bacillus atrophaeus* JCM 9070, the bacterium was inoculated into JCM Medium No. 22 (10 g of polypeptone, 10 g of beef extract, and 5 g of NaCl were dissolved in 1 L of distilled water) with the use of a platinum loop, and cultured with shaking at 30° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Bacillus subtilis* subsp. *spizizenii* NBRC 101239, the bacterium was inoculated into NBRC Medium No. 802 (10 g of polypeptone, 2 g of yeast extract, and 1 g of $MgSO_4.7H_2O$ were dissolved in 1 L of distilled water) with the use of a platinum loop, and cultured with shaking at 37° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

The chromosomal DNA of *Citrobacter koseri* ATCC BAA-895 (catalog No. BAA-895D-5) was obtained from American Type Culture Collection (ATCC).

To extract chromosomal DNA from *Enterobacter aerogenes* NBRC 13534, the bacterium was inoculated into NBRC Medium No. 802 (10 g of polypeptone, 2 g of yeast extract, and 1 g of $MgSO_4.7H_2O$ were dissolved in 1 L of distilled water) with the use of a platinum loop, and cultured with shaking at 37° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Enterobacter cloacae* NBRC 13535, the bacterium was inoculated into NBRC Medium No. 802 (10 g of polypeptone, 2 g of yeast extract, and 1 g of $MgSO_4.7H_2O$ were dissolved in 1 L of distilled water) with the use of a platinum loop, and cultured with shaking at 37° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Enterobacter hormaechei* ATCC 49162, the bacterium was inoculated into Tryptic Soy Broth Medium (30 g of Tryptic Soy Broth (made by Becton Dickinson and Company, catalog No. 211825) was dissolved in 1 L of distilled water) with the use of a platinum loop, and cultured with shaking at 30° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

The chromosomal DNA of *Enterobacter sakazakii* ATCC BAA-894 (catalog No. BAA-894D-5) was obtained from American Type Culture Collection (ATCC).

To extract chromosomal DNA from *Escherichia coli* W NBRC 13500, the bacterium was inoculated into NBRC Medium No. 802 (10 g of polypeptone, 2 g of yeast extract, and 1 g of $MgSO_4.7H_2O$ were dissolved in 1 L of distilled water) with the use of a platinum loop, and cultured with shaking at 30° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Escherichia fergusonii* NBRC 102419, the bacterium was inoculated into NBRC Medium No. 802 (10 g of polypeptone, 2 g of yeast extract, and 1 g of $MgSO_4.7H_2O$ were dissolved in 1 L of distilled water) with the use of a platinum loop, and cultured with shaking at 30° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Paenibacillus polymyxa* NBRC 15309, the bacterium was inoculated into NBRC Medium No. 802 (10 g of polypeptone, 2 g of yeast extract, and 1 g of MgSO$_4$.7H$_2$O were dissolved in 1 L of distilled water) with the use of a platinum loop, and cultured with shaking at 30° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Pantoea ananatis* LMG 20103, the bacterium was inoculated into BCCM/LMG BateriCulture Medium No. 1 (1 g of beef extract, 2 g of yeast extract, 5 g of peptone, and 5 g of NaCl were dissolved in 1 L of distilled water) with the use of a platinum loop, and cultured with shaking at 30° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

(2) Construction of Cloning Vectors Construction of Cloning Vector pCRB22

A DNA fragment comprising a DNA replication origin sequence of pCASE1, a plasmid derived from *Corynebacterium casei* JCM12072 (hereinafter abbreviated as pCASE1-ori) and a DNA fragment comprising a cloning vector pHSG298 (made by Takara Bio, Inc.) were amplified by the following PCR method.

In the PCR, the following sets of primers were synthesized based on SEQ ID NO: 1 (pCASE1-ori sequence) and SEQ ID NO: 2 (cloning vector pHSG298) for cloning of the pCASE1-ori sequence and the cloning vector pHSG298, and were used.

Primers for pCASE1-Ori Sequence Amplification

```
                                         (SEQ ID NO: 3)
(a-1); 5'-AT AGATCT AGAACGTCCGTAGGAGC-3'

(SEQ ID NO: 4)
(b-1); 5'-AT AGATCT GACTTGGTTACGATGGAC-3'
```

Primers (a-1) and (b-1) each have a BglII restriction enzyme site added thereto.

Primers for Cloning Vector pHSG298 Amplification

```
                                         (SEQ ID NO: 5)
(a-2): 5'-AT AGATCT AGGTTTCCCGACTGGAAAG-3'

(SEQ ID NO: 6)
(b-2): 5'-AT AGATCT CGTGCCAGCTGCATTAATGA-3'
```

Primers (a-2) and (b-2) each have a BglII restriction enzyme site added thereto.

As the template DNA, total DNA extracted from *Corynebacterium casei* JCM12072 obtained from Japan Collection of Microorganisms (JCM) and cloning vector pHSG298 (made by Takara Bio, Inc.) were used.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/µL) | 0.5 µL |
| 10× LA PCR ™ Buffer II (Mg$^{2+}$ free) | 5 µL |
| 25 mM MgCl$_2$ | 5 µL |
| dNTP Mixture (2.5 mM each) | 8 µL |
| Template DNA | 5 µL (DNA content: 1 µg or less) |
| The above 2 primers*$^)$ | 0.5 µL each (final conc.: 1 µM) |
| Sterile distilled water | 25.5 µL |

The above ingredients were mixed, and 50 µL of the reaction mixture was subjected to PCR.
*$^)$For amplification of the pCASE1-ori sequence, a combination of primers (a-1) and (b-1), and for amplification of the cloning vector pHSG298, a combination of primers (a-2) and (b-2) were used.

PCR Cycle:

Denaturation step: 94° C., 60 seconds

Annealing step: 52° C., 60 seconds

Extension step: 72° C.

pCASE1-ori sequence: 150 seconds

Cloning vector pHSG298: 180 seconds

A cycle consisting of the above 3 steps was repeated 30 times.

Using 10 µL of the above-produced reaction mixture, 0.8% agarose gel electrophoresis was performed. In the case of the pCASE1-ori sequence, an about 1.4-kb DNA fragment was detected. In the case of the cloning vector pHSG298, an about 2.7-kb DNA fragment was detected.

10 µL of the about 1.4-kb DNA fragment comprising the pCASE1-ori sequence derived from *Corynebacterium casei*, and 10 µL of the about 2.7-kb DNA fragment comprising the cloning vector pHSG298, both amplified by the above PCR, were each cut with the use of restriction enzyme BglII and processed at 70° C. for 10 minutes for deactivation of the restriction enzyme. Both were mixed, and 1 µL of T4 DNA ligase 10× buffer solution and 1 unit of T4 DNA ligase (made by Takara Bio, Inc.) were added thereto. Sterile distilled water was added thereto so that the total volume was 10 µL, and the mixture was allowed to react at 15° C. for 3 hours for ligation. This was named Ligation Liquid A.

With the use of the Ligation Liquid A, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture and cut with the use of restriction enzyme BglII to confirm the inserted fragment. As a result, in addition to an about 2.7-kb DNA fragment of the cloning vector pHSG298, an about 1.4-kb DNA fragment of the pCASE-ori sequence was confirmed.

The cloning vector comprising the pCASE1-ori sequence was named pCRB22.

Construction of Cloning Vector pCRB11

A DNA fragment comprising a DNA replication origin sequence of pCG1 (JP 57-134500 A), which is a plasmid replicable in *Corynebacterium glutamicum* (hereinafter abbreviated as pCG1-ori) and a DNA fragment comprising a cloning vector pHSG398 (made by Takara Bio, Inc.) were amplified by the following PCR method.

In the PCR, the following sets of primers were synthesized based on SEQ ID NO: 7 (pCG1-ori sequence) and SEQ ID NO: 8 (cloning vector pHSG398) for cloning of the pCG1-ori sequence and the cloning vector pHSG398, and were used.

Primers for pCG1-Ori Sequence Amplification (SEQ ID NO: 9)
(a-3): 5'-AT AGATCT AGCATGGTCGTCACAGAG-3'

(SEQ ID NO: 10)
(b-3): 5'-AT AGATCT GGAACCGTTATCTGCCTATG-3'

Primers (a-3) and (b-3) each have a BglII restriction enzyme site added thereto.
Primers for Cloning Vector pHSG398 Amplification (SEQ ID NO: 11)
(a-4): 5'-AT AGATCT GTCGAACGGAAGATCACTTC-3'

(SEQ ID NO: 12)
(b-4): 5'-AT AGATCT AGTTCCACTGAGCGTCAG-3'

Primers (a-4) and (b-4) each have a BglII restriction enzyme site added thereto.

As the template DNA, pCG1 (JP 57-134500 A) and cloning vector pHSG398 (made by Takara Bio, Inc.) were used.

Actual PCR was performed with use of a thermal cycler, GeneAmp PCR System 9700 (made by Applied Biosystems) and TaKaRa LA Taq (made by Takara Bio, Inc.) as a reaction reagent under the conditions described below.
Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*$^)$ | 0.5 μL each (final conc.: 1 μM) |
| Sterile distilled water: | 25.5 μL |

The above ingredients were mixed, and 50 μL of the reaction mixture was subjected to PCR.
*$^)$For amplification of the pCG1-ori sequence, a combination of primers (a-3) and (b-3), and for amplification of the cloning vector pHSG398, a combination of primers (a-4) and (b-4) were used.

PCR Cycle:
  Denaturation step: 94° C., 60 seconds
  Annealing step: 52° C., 60 seconds
  Extension step: 72° C.
  pCG1-ori sequence: 120 seconds
  Cloning vector pHSG398: 150 seconds
  A cycle consisting of the above 3 steps was repeated 30 times.

Using 10 μL of the above-produced reaction mixture, 0.8% agarose gel electrophoresis was performed. In the case of the pCG1-ori sequence, an about 1.9-kb DNA fragment was detected. In the case of the cloning vector pHSG398, an about 2.2-kb DNA fragment was detected.

10 μL of the about 1.9-kb DNA fragment comprising the pCG1-ori gene, which is derived from a plasmid pCG1, and 10 μL of the about 2.2-kb DNA fragment comprising the cloning vector pHSG398, both amplified by the above PCR, were each cut with use of a restriction enzyme BglII and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total amount was 10 μL, and the mixture was allowed to react at 15° C. for 3 hours for ligation. This was named Ligation Liquid B.

With use of the Ligation Liquid B, *Escherichia coli* JM109 was transformed by the calcium chloride method (Journal of Molecular Biology, 53, 159 (1970)) and was applied to LB agar medium (1% of polypeptone, 0.5% of yeast extract, 0.5% of sodium chloride, and 1.5% of agar) containing 50 μg/mL of chloramphenicol.

A growing strain on the culture medium was subjected to liquid culture in the usual manner. Plasmid DNA was extracted from the culture medium and cut with use of a restriction enzyme BglII to confirm the inserted fragment. As a result, in addition to an about 2.2-kb DNA fragment of the cloning vector pHSG398, an about 1.9-kb DNA fragment of pCG1-ori sequence was confirmed.

The plasmid comprising the pCG1-ori sequence was named pCRB11.

Construction of Cloning Vector pCRB15

A DNA fragment comprising a cloning vector pCRB11 and a DNA fragment comprising a zeocin resistance gene derived from pSELECT-zeo-mcs (made by Invitrogen Corp.) were amplified by the following PCR method.

In the PCR, the following sets of primers were synthesized based on SEQ ID NO: 13 (pCRB11) and SEQ ID NO: 14 (zeocin resistance gene) for cloning of the cloning vector pCRB11 and the zeocin resistance gene, and were used.
Primers for Cloning Vector pCRB11 Amplification (SEQ ID NO: 15)
(a-5): 5'-AT GATATC CGAAGTGATCTTCCGTTCGA-3'

(SEQ ID NO: 16)
(b-5): 5'-AT GATATC AAGGCAGTTATTGGTGCCCT-3'

Primers (a-5) and (b-5) each have an EcoRV restriction enzyme site added thereto.
Primers for Zeocin Resistance Gene Amplification (SEQ ID NO: 17)
(a-6): 5'-AT GATATC TAGCTTATCCTCAGTCCTGC-3'

(SEQ ID NO: 18)
(b-6): 5'-AT GATATC CCATCCACGCTGTTTTGACA-3'

Primers (a-6) and (b-6) each have an EcoRV restriction enzyme site added thereto.

As the template DNA, cloning vector pCRB11 and pSELECT-zeo-mcs (made by Invitrogen Corp.) were used.

Actual PCR was performed with use of a thermal cycler, GeneAmp PCR System 9700 (made by Applied Biosystems) and TaKaRa LA Tag (made by Takara Bio, Inc.) as a reaction reagent under the conditions described below.
Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*$^)$ | 0.5 μL each (final conc.: 1 μM) |
| Sterile distilled water: | 25.5 μL |

The above ingredients were mixed, and 50 μL of the reaction mixture was subjected to PCR.
*$^)$For amplification of the cloning vector pCRB11 sequence, a combination of primers (a-5) and (b-5), and for amplification of the zeocin resistance gene, a combination of primers (a-6) and (b-6) were used.

PCR Cycle:
  Denaturation step: 94° C., 60 seconds
  Annealing step: 52° C., 60 seconds
  Extension step: 72° C.
  pCRB11 sequence: 200 seconds
  Zeocin resistance gene: 45 seconds A cycle consisting of the above 3 steps was repeated 30 times.

Using 10 μL of the above-produced reaction mixture, 0.8% agarose gel electrophoresis was performed. In the case of the cloning vector pCRB11 sequence, an about 3.3-kb DNA fragment was detected. In the case of the zeocin resistance gene, an about 0.5-kb DNA fragment was detected.

10 μL of the about 3.3-kb DNA fragment comprising the cloning vector pCRB11 and 10 μL of the about 0.5-kb DNA fragment comprising the zeocin resistance gene derived from a plasmid pSELECT-zeo-mcs, both amplified by the above PCR, were each cut with use of a restriction enzyme EcoRV and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total amount was 10 μL, and the mixture was allowed to react at 15° C. for 3 hours for ligation. This was named Ligation Liquid C.

Construction of Cloning Vector pCRB207

A DNA fragment comprising a promoter sequence of the gapA gene encoding the glyceraldehyde-3-phosphate dehydrogenase (hereinafter abbreviated as PgapA) derived from *Corynebacterium glutamicum* R, and a DNA fragment comprising an rrnBT1T2 bidirectional terminator sequence (hereinafter abbreviated as terminator sequence) derived from a cloning vector pKK223-3 (made by Pharmacia) were amplified by the following method.

In the PCR, the following sets of primers were synthesized based on SEQ ID NO: 19 (PgapA sequence) and SEQ ID NO: 20 (terminator sequence) for cloning of the PgapA sequence and the terminator sequence, and were used.

Primers for PgapA Sequence Amplification

```
(a-7);
                                      (SEQ ID NO: 21)
5'-CTCT GTCGAC CCGAAGATCTGAAGATTCCTG-3'

(b-7);
                                      (SEQ ID NO: 22)
5'-CTCT GTCGAC GGATCC CCATGG

TGTGTCTCCTCTAAAGATTGTAGG-3'
```

Primer (a-7) has a SalI restriction enzyme site added thereto, and primer (b-7) has SalI, BamHI, and NcoI restriction enzyme sites added thereto.

Primers for Terminator Sequence Amplification

```
(a-8);
                                      (SEQ ID NO: 23)
5'-CTCT GCATGC CCATGG CTGTTTTGGCGGATGAGAGA-3'

(b-8);
                                      (SEQ ID NO: 24)
5'-CTCT GCATGC TCATGA

AAGAGTTTGTAGAAACGCAAAAAGG-3'
```

Primer (a-8) has SphI and NcoI restriction enzyme sites added thereto, and primer (b-8) has SphI and BspHI restriction enzyme sites added thereto.

As the template DNA, the chromosomal DNA extracted from *Corynebacterium glutamicum* R (FERM P-18976) and the plasmid pKK223-3 (made by Pharmacia) were used.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*⁾ | 0.5 μL each (final conc.: 1 μM) |
| Sterile distilled water | 25.5 μL |

The above ingredients were mixed, and 50 μL of the reaction mixture was subjected to PCR.
*⁾For amplification of the PgapA sequence, a combination of primers (a-7) and (b-7), and for amplification of the terminator sequence, a combination of primers (a-8) and (b-8) were used.

PCR Cycle:
Denaturation step: 94° C., 60 seconds
Annealing step: 52° C., 60 seconds
Extension step: 72° C.
PgapA sequence: 45 seconds
Terminator sequence: 30 seconds A cycle consisting of the above 3 steps was repeated 30 times.

Using 10 μL of the above-produced reaction mixture, 0.8% agarose gel electrophoresis was performed. In the case of the PgapA sequence, an about 0.6-kb DNA fragment was detected. In the case of the terminator sequence, an about 0.4-kb DNA fragment was detected.

10 μL of the about 0.6-kb DNA fragment comprising the PgapA sequence derived from *Corynebacterium glutamicum* R, which was amplified by the above PCR, and the about 4.1-kb cloning vector pCRB22 were each cut with the use of restriction enzyme SalI and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named Ligation Liquid D.

With the use of the Ligation Liquid D, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of restriction enzyme SalI to confirm the inserted fragment. As a result, in addition to an about 4.1-kb DNA fragment of the cloning vector pCRB22, an about 0.6-kb DNA fragment of the PgapA sequence was confirmed.

The cloning vector comprising the PgapA sequence was named pCRB206.

10 μL of the about 0.4-kb DNA fragment comprising the terminator sequence derived from the plasmid pKK223-3, which was amplified by the above PCR, was cut with the use of restriction enzymes NcoI and BspHI, 2 μL of the above cloning vector pCRB206 was cut with the use of restriction enzyme NcoI, and both were processed at 70° C. for 10 minutes for deactivation of the restriction enzymes. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named Ligation Liquid E.

With the use of the Ligation Liquid E, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture and cut with the use of the restriction enzyme to confirm the inserted fragment. As a result, in addition to an about 4.7-kb DNA fragment of the cloning vector pCRB206, an about 0.4-kb DNA fragment of the terminator sequence was confirmed.

The cloning vector comprising the rrnBT1T2 terminator sequence was named pCRB207.

Construction of Cloning Vector pCRB209

A DNA fragment comprising a promoter sequence of the gapA (glyceraldehyde 3-phosphate dehydrogenase A) gene (hereinafter abbreviated as PgapA) derived from *Corynebacterium glutamicum* R was amplified by the following method.

In the PCR, the following set of primers was synthesized based on SEQ ID NO: 25 (pCRB207) for cloning of the pCRB207 sequence, and was used.

Primers for pCRB207 Sequence Amplification

```
                                            (SEQ ID NO: 26)
(a-9); 5'-CTCT CATATG CTGTTTTGGCGGATGAGAG-3'

(SEQ ID NO: 27)
(b-9); 5'-CTCT CATATG GTGTCTCCTCTAAAGATTGTAGG-3'
```

Primers (a-9) and (b-9) each have an NdeI restriction enzyme site added thereto.

As the template DNA, the cloning vector pCRB207 comprising a gapA promoter and a rrnBT1T2 terminator sequence was used.

Actual PCR was performed with the use of a thermal cycler, GeneAmp PCR System 9700 (made by Applied Biosystems) and TaKaRa LA Taq (made by Takara SHUZO) as a reaction reagent under the conditions described below.

Reaction Mixture:

| | |
|---|---|
| TaKaRa LA Taq ™ (5 units/µL) | 0.5 µL |
| 10× LA PCR ™ Buffer II (Mg²⁺ free) | 5 µL |
| 25 mM MgCl₂ | 5 µL |
| dNTP Mixture (2.5 mM each) | 8 µL |
| Template DNA | 5 µL (DNA content: 1 µg or less) |
| The above 2 primers*⁾ | 0.5 µL each (final conc.: 1 µM) |
| Sterile distilled water | 25.5 µL |

The above ingredients were mixed, and 50 µL of the reaction mixture was subjected to PCR.
*⁾For amplification of the pCRB207 sequence, a combination of primers (a-9) and (b-9) was used.

PCR Cycle:
Denaturation step: 94° C., 60 seconds
Annealing step: 52° C., 60 seconds
Extension step: 72° C., 307 seconds A cycle consisting of the above 3 steps was repeated 30 times.

Using 10 µL of the above-produced reaction mixture, 0.8% agarose gel electrophoresis was performed, and an about 5.1-kb DNA fragment comprising the cloning vector pCRB207 was detected.

10 µL of the about 5.1-kb DNA fragment comprising the gene derived from pCRB207, which was amplified by the above PCR, was cut with the use of restriction enzyme NdeI and processed at 70° C. for 10 minutes for deactivation of the restriction enzyme. To this, 1 µL of T4 DNA ligase 10× buffer solution and 1 unit of T4 DNA ligase (made by Takara SHUZO) were added. Sterile distilled water was added thereto so that the total volume was 10 µL, and the mixture was allowed to react at 15° C. for 3 hours for ligation. This was named Ligation Liquid F.

With the use of the Ligation Liquid F, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture and cut with the use of restriction enzyme NdeI to confirm the inserted restriction enzyme site.

The cloning vector comprising the PgapA sequence and the rrnBT1T2 terminator sequence was named pCRB209.

(3) Cloning of Phenol-Producing Genes (3-1) DAHP Synthetase Gene (aroG)

Cloning of Phenol-Producing Gene Derived from *Corynebacterium glutamicum*

A DNA fragment comprising the aroG gene which encodes DAHP synthetase derived from *Corynebacterium glutamicum* was amplified by the PCR method as described below.

In the PCR, the following set of primers was synthesized based on SEQ ID NO: 28 (the aroG gene of *Corynebacterium glutamicum*) with the use of "394 DNA/RNA Synthesizer" made by Applied Biosystems for cloning of the aroG gene and was used.

Primers for aroG Gene Amplification

```
(a-10);
                                            (SEQ ID NO: 29)
5'-CTCT CATATG AATAGGGGTGTGAGTTGG-3'

(b-10);
                                            (SEQ ID NO: 30)
5'-CTCT CATATG TTAATTACGCAGCATTTCTGCAACG-3'
```

Primers (a-10) and (b-10) each have an NdeI restriction enzyme site added thereto.

(3-2) Chorismate-Pyruvate Lyase Gene (ubiC)

Cloning of Phenol-Producing Gene Derived from *Escherichia coli*

A DNA fragment comprising the ubiC gene which is derived from *Escherichia coli* and which encodes a gene having chorismate-pyruvate lyase activity was amplified by the PCR method as described below.

In the PCR, the following set of primers was synthesized based on SEQ ID NO: 31 (the ubiC gene of *Escherichia coli*) with the use of "394 DNA/RNA Synthesizer" made by Applied Biosystems for cloning of the ubiC gene, and was used.

Primers for ubiC Gene Amplification

```
                                            (SEQ ID NO: 32)
(a-11); 5'-CTCT CATATG TCACACCCCGCGTTAA-3'

(SEQ ID NO: 33)
(b-11); 5'-CTCT CATATG TTAGTACAACGGTGACGCC-3'
```

Primers (a-11) and (b-11) each have an NdeI restriction enzyme site added thereto.

Cloning of Phenol-Producing Gene Derived from *Pseudomonas putida*

A DNA fragment comprising the ubiC gene which is derived from *Pseudomonas putida* and which encodes a gene having chorismate-pyruvate lyase activity was amplified by the PCR method as described below.

In the PCR, the following set of primers was synthesized based on SEQ ID NO: 34 (the ubiC gene of *Pseudomonas putida*) with the use of "394 DNA/RNA Synthesizer" made by Applied Biosystems for cloning of the ubiC gene, and was used.

Primers for ubiC Gene Amplification

```
(a-12);
                                  (SEQ ID NO: 35)
5'-CTCT CATATG TCGTACGAATCCCCG-3'

(b-12);
                                  (SEQ ID NO: 36)
5'-CTCT CATATG TCAGCGGTTTTCCTCCTTG-3'
```

Primers (a-12) and (b-12) each have an NdeI restriction enzyme site added thereto.

Cloning of Phenol-Producing Gene Derived from *Acinetobacter baumannii*

A DNA fragment comprising the ubiC gene which is derived from *Acinetobacter baumannii* and which encodes a gene having chorismate-pyruvate lyase activity was amplified by the PCR method as described below.

In the PCR, the following set of primers was synthesized based on SEQ ID NO: 81 (the ubiC gene of *Acinetobacter baumannii*) with the use of "394 DNA/RNA Synthesizer" made by Applied Biosystems for cloning of the ubiC gene, and was used.

Primers for ubiC Gene Amplification

```
(a-29);
                                  (SEQ ID NO: 94)
5'-CTCT CATATG CGTAAACGACAACCAGTAC-3'

(b-29);
                                  (SEQ ID NO: 95)
5'-CTCT CATATG TCATAGTAATTCCTTGTCGTGCTG-3'
```

Primers (a-29) and (b-29) each have an NdeI restriction enzyme site added thereto.

Cloning of Phenol-Producing Gene Derived from *Azotobacter vinelandii*

A DNA fragment comprising the ubiC gene which is derived from *Azotobacter vinelandii* and which encodes a gene having chorismate-pyruvate lyase activity was amplified by the PCR method as described below.

In the PCR, the following set of primers was synthesized based on SEQ ID NO: 82 (the ubiC gene of *Azotobacter vinelandii*) with the use of "394 DNA/RNA Synthesizer" made by Applied Biosystems for cloning of the ubiC gene, and was used.

Primers for ubiC Gene Amplification

```
(a-30);
                                  (SEQ ID NO: 96)
5'-CTCT CATATG ACCGCTGCTCCCG-3'

(b-30);
                                  (SEQ ID NO: 97)
5'-CTCT CATATG TTATAGGGTGTCCGGGTC-3'
```

Primers (a-30) and (b-30) each have an NdeI restriction enzyme site added thereto.

Cloning of Phenol-Producing Gene Derived from *Chromohalobacter salexigens*

A DNA fragment comprising the ubiC gene which is derived from *Chromohalobacter salexigens* and which encodes a gene having chorismate-pyruvate lyase activity was amplified by the PCR method as described below.

In the PCR, the following set of primers was synthesized based on SEQ ID NO: 83 (the ubiC gene of *Chromohalobacter salexigens*) with the use of "394 DNA/RNA Synthesizer" made by Applied Biosystems for cloning of the ubiC gene, and was used.

Primers for ubiC Gene Amplification

```
(a-31);
                                  (SEQ ID NO: 98)
5'-CTCT CATATG TCTCCTGACCGCTTC-3'

(b-31);
                                  (SEQ ID NO: 99)
5'-CTCT CATATG TTAGCGCGATGGCAGCG-3'
```

Primers (a-31) and (b-31) each have an NdeI restriction enzyme site added thereto.

Cloning of Phenol-Producing Gene Derived from *Citrobacter koseri*

A DNA fragment comprising the ubiC gene which is derived from *Citrobacter koseri* and which encodes a gene having chorismate-pyruvate lyase activity was amplified by the PCR method as described below.

In the PCR, the following set of primers was synthesized based on SEQ ID NO: 84 (the ubiC gene of *Citrobacter koseri*) with the use of "394 DNA/RNA Synthesizer" made by Applied Biosystems for cloning of the ubiC gene, and was used.

Primers for ubiC Gene Amplification

```
(a-32);
                                  (SEQ ID NO: 100)
5'-CTCT CATATG TCACACCCTGCGTTAAC-3'

(b-32);
                                  (SEQ ID NO: 101)
5'-CTCT CATATG TTAATACAACGGTGATGCGGG-3'
```

Primers (a-32) and (b-32) each have an NdeI restriction enzyme site added thereto.

Cloning of Phenol-Producing Gene Derived from *Citrobacter youngae*

A DNA fragment comprising the ubiC gene which is derived from *Citrobacter youngae* and which encodes a gene having chorismate-pyruvate lyase activity was amplified by the PCR method as described below.

In the PCR, the following set of primers was synthesized based on SEQ ID NO: 85 (the ubiC gene of *Citrobacter youngae*) with the use of "394 DNA/RNA Synthesizer" made by Applied Biosystems for cloning of the ubiC gene, and was used.

Primers for ubiC Gene Amplification

```
(a-33);
                                  (SEQ ID NO: 102)
5'-CTCT CATATG CCACACCCTGCGTTAA-3'

(b-33);
                                  (SEQ ID NO: 103)
5'-CTCT CATATG TCAGTACAACGGCGATGCA-3'
```

Primers (a-33) and (b-33) each have an NdeI restriction enzyme site added thereto.

Cloning of Phenol-Producing Gene Derived from *Enterobacter cloacae*

A DNA fragment comprising the ubiC gene which is derived from *Enterobacter cloacae* and which encodes a gene having chorismate-pyruvate lyase activity was amplified by the PCR method as described below.

In the PCR, the following set of primers was synthesized based on SEQ ID NO: 86 (the ubiC gene of *Enterobacter cloacae*) with the use of "394 DNA/RNA Synthesizer" made by Applied Biosystems for cloning of the ubiC gene, and was used.

Primers for ubiC Gene Amplification

```
(a-34);
                                    (SEQ ID NO: 104)
5'-CTCT CATATG TCACACCCTGCGCTAA-3'

(b-34);
                                    (SEQ ID NO: 105)
5'-CTCT CATATG TCAGTACAACGGCGATGC-3'
```

Primers (a-34) and (b-34) each have an NdeI restriction enzyme site added thereto.

Cloning of Phenol-Producing Gene Derived from *Marinobacter aquaeolei*

A DNA fragment comprising the ubiC gene which is derived from *Marinobacter aquaeolei* and which encodes a gene having chorismate-pyruvate lyase activity was amplified by the PCR method as described below.

In the PCR, the following set of primers was synthesized based on SEQ ID NO: 87 (the ubiC gene of *Marinobacter aquaeolei*) with the use of "394 DNA/RNA Synthesizer" made by Applied Biosystems for cloning of the ubiC gene, and was used.

Primers for ubiC Gene Amplification

```
(a-35);
                                    (SEQ ID NO: 106)
5'-CTCT CATATG CCGTTAAAGGACTGTGAC-3'

(b-35);
                                    (SEQ ID NO: 107)
5'-CTCT CATATG TTAACCCCGGTTGGGC-3'
```

Primers (a-35) and (b-35) each have an NdeI restriction enzyme site added thereto.

Cloning of Phenol-Producing Gene Derived from *Marinomonas mediterranea*

A DNA fragment comprising the ubiC gene which is derived from *Marinomonas mediterranea* and which encodes a gene having chorismate-pyruvate lyase activity was amplified by the PCR method as described below.

In the PCR, the following set of primers was synthesized based on SEQ ID NO: 88 (the ubiC gene of *Marinomonas mediterranea*) with the use of "394 DNA/RNA Synthesizer" made by Applied Biosystems for cloning of the ubiC gene, and was used.

Primers for ubiC Gene Amplification

```
(a-36);
                                    (SEQ ID NO: 108)
5'-CTCT CATATG ACGTTACTCAATAAAAACGCTG-3'

(b-36);
                                    (SEQ ID NO: 109)
5'-CTCT CATATG CTACAGCTGGCCTATGGTA-3'
```

Primers (a-36) and (b-36) each have an NdeI restriction enzyme site added thereto.

Cloning of Phenol-Producing Gene Derived from *Pantoea ananatis*

A DNA fragment comprising the ubiC gene which is derived from *Pantoea ananatis* and which encodes a gene having chorismate-pyruvate lyase activity was amplified by the PCR method as described below.

In the PCR, the following set of primers was synthesized based on SEQ ID NO: 89 (the ubiC gene of *Pantoea ananatis*) with the use of "394 DNA/RNA Synthesizer" made by Applied Biosystems for cloning of the ubiC gene, and was used.

Primers for ubiC Gene Amplification

```
(a-37);
                                    (SEQ ID NO: 110)
5'-CTCT CATATG ACGCAAGACCCGCT-3'

(b-37);
                                    (SEQ ID NO: 111)
5'-CTCT CATATG TTAACCTTGATCACGATAGAGCG-3'
```

Primers (a-37) and (b-37) each have an NdeI restriction enzyme site added thereto.

Cloning of Phenol-Producing Gene Derived from *Pseudoalteromonas haloplanktis*

A DNA fragment comprising the ubiC gene which is derived from *Pseudoalteromonas haloplanktis* and which encodes a gene having chorismate-pyruvate lyase activity was amplified by the PCR method as described below.

In the PCR, the following set of primers was synthesized based on SEQ ID NO: 90 (the ubiC gene of *Pseudoalteromonas haloplanktis*) with the use of "394 DNA/RNA Synthesizer" made by Applied Biosystems for cloning of the ubiC gene, and was used.

Primers for ubiC Gene Amplification

```
(a-38);
                                    (SEQ ID NO: 112)
5'-CTCT CATATG ATTACTTTCCCTGTTTCATTATCTGC-3'

(b-38);
                                    (SEQ ID NO: 113)
5'-CTCT CATATG TCATGAGTACAAATACGCTCCTG-3'
```

Primers (a-38) and (b-38) each have an NdeI restriction enzyme site added thereto.

Cloning of Phenol-Producing Gene Derived from *Ralstonia eutropha*

A DNA fragment comprising the ubiC gene which is derived from *Ralstonia eutropha* and which encodes a gene having chorismate-pyruvate lyase activity was amplified by the PCR method as described below.

In the PCR, the following set of primers was synthesized based on SEQ ID NO: 91 (the ubiC gene of *Ralstonia eutropha*) with the use of "394 DNA/RNA Synthesizer" made by Applied Biosystems for cloning of the ubiC gene, and was used.

Primers for ubiC Gene Amplification

```
(a-39);
                                    (SEQ ID NO: 114)
5'-CTCT CATATG AGCGCGCAGTCCG-3'

(b-39);
                                    (SEQ ID NO: 115)
5'-CTCT CATATG TCATCTCGTGGTCTCTTTCTTG-3'
```

Primers (a-39) and (b-39) each have an NdeI restriction enzyme site added thereto.

Cloning of Phenol-Producing Gene Derived from *Shewanella putrefaciens*

A DNA fragment comprising the ubiC gene which is derived from *Shewanella putrefaciens* and which encodes a gene having chorismate-pyruvate lyase activity was amplified by the PCR method as described below.

In the PCR, the following set of primers was synthesized based on SEQ ID NO: 92 (the ubiC gene of *Shewanella putrefaciens*) with the use of "394 DNA/RNA Synthesizer" made by Applied Biosystems for cloning of the ubiC gene, and was used.
Primers for ubiC Gene Amplification

```
    (a-40);
                                    (SEQ ID NO: 116)
    5'-CTCT CATATG AATGTGACTAGCTTAAGCTTCC-3'

(b-40);
                                    (SEQ ID NO: 117)
    5'-CTCT CATATG TCACTGGCAAATTGCTCGC-3'
```

Primers (a-40) and (b-40) each have an NdeI restriction enzyme site added thereto.
Cloning of Phenol-Producing Gene Derived from *Thiobacillus denitrificans*

A DNA fragment comprising the ubiC gene which is derived from *Thiobacillus denitrificans* and which encodes a gene having chorismate-pyruvate lyase activity was amplified by the PCR method as described below.

In the PCR, the following set of primers was synthesized based on SEQ ID NO: 93 (the ubiC gene of *Thiobacillus denitrificans*) with the use of "394 DNA/RNA Synthesizer" made by Applied Biosystems for cloning of the ubiC gene, and was used.
Primers for ubiC Gene Amplification

```
    (a-41);
                                    (SEQ ID NO: 118)
    5'-CTCT CATATG ATCGCCACGCGCG-3'

(b-41);
                                    (SEQ ID NO: 119)
    5'-CTCT CATATG TCATGGCGTTAATAGGGCG-3'
```

Primers (a-41) and (b-41) each have an NdeI restriction enzyme site added thereto.
Cloning of Phenol-Producing Gene Derived from *Bacillus subtilis*

A DNA fragment comprising the bsdBCD gene which is derived from *Bacillus subtilis* and which encodes a gene having 4-hydroxybenzoate decarboxylase activity was amplified by the PCR method as described below.

In the PCR, the following set of primers was synthesized based on SEQ ID NO: 37 (the bsdBCD gene of *Bacillus subtilis*) with the use of "394 DNA/RNA Synthesizer" made by Applied Biosystems for cloning of the bsdBCD gene, and was used.
Primers for bsdBCD Gene Amplification

```
    (a-13);
                                    (SEQ ID NO: 38)
    5'-CTCT CATATG AAAGCAGAATTCAAGCGTAAAG-3'

(b-13);
                                    (SEQ ID NO: 39)
    5'-CTCT CATATG GATCAAGCCTTTCGTTCCG-3'
```

Primers (a-13) and (b-13) each have an NdeI restriction enzyme site added thereto.

Cloning of Phenol-Producing Gene Derived from *Bacillus atrophaeus*

A DNA fragment comprising the dca gene which is derived from *Bacillus atrophaeus* and which encodes a gene having 4-hydroxybenzoate decarboxylase activity was amplified by the PCR method as described below.

In the PCR, the following set of primers was synthesized based on SEQ ID NO: 44 (the dca gene of *Bacillus atrophaeus*) with the use of "394 DNA/RNA Synthesizer" made by Applied Biosystems for cloning of the dca gene, and was used.
Primers for dca Gene Amplification

```
                                    (SEQ ID NO: 45)
    (a-16); 5'-CTCT CATATG AAACTCGTTGTCGGGATG-3'

(SEQ ID NO: 46)
    (b-16); 5'-CTCT CATATG TCAGGCCTTTCTTTCC-3'
```

Primers (a-16) and (b-16) each have an NdeI restriction enzyme site added thereto.
Cloning of Phenol-Producing Gene Derived from *Bacillus subtilis* subsp. *spizizenii*

A DNA fragment comprising the dca gene which is derived from *Bacillus subtilis* subsp. *spizizenii* and which encodes a gene having 4-hydroxybenzoate decarboxylase activity was amplified by the PCR method as described below.

In the PCR, the following set of primers was synthesized based on SEQ ID NO: 47 (the dca gene of *Bacillus subtilis* subsp. *spizizenii*) with the use of "394 DNA/RNA Synthesizer" made by Applied Biosystems for cloning of the dca gene, and was used.
Primers for dca Gene Amplification

```
                                    (SEQ ID NO: 48)
    (a-17); 5'-CTCT CATATG AAAGCAGAATTCAAGCGTAAAG-3'

(SEQ ID NO: 49)
    (b-17); 5'-CTCT CATATG TCAAGCCTTTCGTTCCGG-3'
```

Primers (a-17) and (b-17) each have an NdeI restriction enzyme site added thereto.
Cloning of Phenol-Producing Gene Derived from *Citrobacter koseri*

A DNA fragment comprising the dca gene which is derived from *Citrobacter koseri* and which encodes a gene having 4-hydroxybenzoate decarboxylase activity was amplified by the PCR method as described below.

In the PCR, the following set of primers was synthesized based on SEQ ID NO: 50 (the dca gene of *Citrobacter koseri*) with the use of "394 DNA/RNA Synthesizer" made by Applied Biosystems for cloning of the dca gene, and was used.
Primers for dca Gene Amplification

```
                                    (SEQ ID NO: 51)
    (a-18); 5'-CTCT CATATG AAACTCGTTGTCGGGATG-3'

(SEQ ID NO: 52)
    (b-18); 5'-CTCT CATATG TCAGGCCTTTCTTTCC-3'
```

Primers (a-18) and (b-18) each have an NdeI restriction enzyme site added thereto.
Cloning of Phenol-Producing Gene Derived from *Enterobacter aerogenes*

A DNA fragment comprising the dca gene which is derived from *Enterobacter aerogenes* and which encodes a gene having 4-hydroxybenzoate decarboxylase activity was amplified by the PCR method as described below.

In the PCR, the following set of primers was synthesized based on SEQ ID NO: 53 (the dca gene of *Enterobacter aerogenes*) with the use of "394 DNA/RNA Synthesizer" made by Applied Biosystems for cloning of the dca gene, and was used.

Primers for dca Gene Amplification

```
                                            (SEQ ID NO: 54)
(a-19);  5'-CTCT CATATG AAACTGATTATTGGGATGACCG-3'

(SEQ ID NO: 55)
(b-19);  5'-CTCT CATATG TTAACGCTTATCTGCCGCC-3'
```

Primers (a-19) and (b-19) each have an NdeI restriction enzyme site added thereto.

Cloning of Phenol-Producing Gene Derived from *Enterobacter cloacae*

A DNA fragment comprising the dca gene which is derived from *Enterobacter cloacae* and which encodes a gene having 4-hydroxybenzoate decarboxylase activity was amplified by the PCR method as described below.

In the PCR, the following set of primers was synthesized based on SEQ ID NO: 56 (the dca gene of *Enterobacter cloacae*) with the use of "394 DNA/RNA Synthesizer" made by Applied Biosystems for cloning of the dca gene, and was used.

Primers for dca Gene Amplification

```
                                            (SEQ ID NO: 57)
(a-20);  5'-CTCT CATATG AGATTGATCGTGGGAATGAC-3'

(SEQ ID NO: 58)
(b-20);  5'-CTCT CATATG TTACAGCAATGGCGGAATGG-3'
```

Primers (a-20) and (b-20) each have an NdeI restriction enzyme site added thereto.

Cloning of Phenol-Producing Gene Derived from *Enterobacter hormaechei*

A DNA fragment comprising the dca gene which is derived from *Enterobacter hormaechei* and which encodes a gene having 4-hydroxybenzoate decarboxylase activity was amplified by the PCR method as described below.

In the PCR, the following set of primers was synthesized based on SEQ ID NO: 59 (the dca gene of *Enterobacter hormaechei*) with the use of "394 DNA/RNA Synthesizer" made by Applied Biosystems for cloning of the dca gene, and was used.

Primers for dca Gene Amplification

```
                                            (SEQ ID NO: 60)
(a-21);  5'-CTCT CATATG AGATTGATTGTGGGAATGAC-3'

(SEQ ID NO: 61)
(b-21);  5'-CTCT CATATG GAGTCTGGTTTAGTTCTCTGC-3'
```

Primers (a-21) and (b-21) each have an NdeI restriction enzyme site added thereto.

Cloning of Phenol-Producing Gene Derived from *Enterobacter sakazakii*

A DNA fragment comprising the dca gene which is derived from *Enterobacter sakazakii* and which encodes a gene having 4-hydroxybenzoate decarboxylase activity was amplified by the PCR method as described below.

In the PCR, the following set of primers was synthesized based on SEQ ID NO: 62 (the dca gene of *Enterobacter sakazakii*) with the use of "394 DNA/RNA Synthesizer" made by Applied Biosystems for cloning of the dca gene, and was used.

Primers for dca Gene Amplification

```
                                            (SEQ ID NO: 63)
(a-22);  5'-CTCT CATATG AGGCTAATTGTCGGAATGAC-3'

(SEQ ID NO: 64)
(b-22);  5'-CTCT CATATG TTAACGCTTACCATCCGCC-3'
```

Primers (a-22) and (b-22) each have an NdeI restriction enzyme site added thereto.

Cloning of Phenol-Producing Gene Derived from *Escherichia coli*

A DNA fragment comprising the dca gene which is derived from *Escherichia coli* and which encodes a gene having 4-hydroxybenzoate decarboxylase activity was amplified by the PCR method as described below.

In the PCR, the following set of primers was synthesized based on SEQ ID NO: 65 (the dca gene of *Escherichia coli*) with the use of "394 DNA/RNA Synthesizer" made by Applied Biosystems for cloning of the dca gene, and was used.

Primers for dca Gene Amplification

```
                                            (SEQ ID NO: 66)
(a-23);  5'-CTCT CATATG AAACTGATCGTCGGGATG-3'

(SEQ ID NO: 67)
(b-23);  5'-CTCT CATATG TTAGCGCTTACCTTCCGC-3'
```

Primers (a-23) and (b-23) each have an NdeI restriction enzyme site added thereto.

Cloning of Phenol-Producing Gene Derived from *Escherichia fergusonii*

A DNA fragment comprising the dca gene which is derived from *Escherichia fergusonii* and which encodes a gene having 4-hydroxybenzoate decarboxylase activity was amplified by the PCR method as described below.

In the PCR, the following set of primers was synthesized based on SEQ ID NO: 68 (the dca gene of *Escherichia fergusonii*) with the use of "394 DNA/RNA Synthesizer" made by Applied Biosystems for cloning of the dca gene, and was used.

Primers for dca Gene Amplification

```
                                            (SEQ ID NO: 69)
(a-24);  5'-CTCT CATATG AGACTGATCGTCGGGAT-3'

(SEQ ID NO: 70)
(b-24);  5'-CTCT CATATG TTAGCGCTTATCTGCCGC-3'
```

Primers (a-24) and (b-24) each have an NdeI restriction enzyme site added thereto.

Cloning of Phenol-Producing Gene Derived from *Paenibacillus polymyxa*

A DNA fragment comprising the dca gene which is derived from *Paenibacillus polymyxa* and which encodes a gene having 4-hydroxybenzoate decarboxylase activity was amplified by the PCR method as described below.

In the PCR, the following set of primers was synthesized based on SEQ ID NO: 71 (the dca gene of *Paenibacillus polymyxa*) with the use of "394 DNA/RNA Synthesizer" made by Applied Biosystems for cloning of the dca gene, and was used.

Primers for dca Gene Amplification

```
                                         (SEQ ID NO: 72)
(a-25); 5'-CTCT CATATG AAGAAAATCATTGTAGGAATATCGG-3'

(SEQ ID NO: 73)
(b-25); 5'-CTCT CATATG CTATATCCGCTCTGGAATAGG-3'
```

Primers (a-25) and (b-25) each have an NdeI restriction enzyme site added thereto.

Cloning of Phenol-Producing Gene Derived from *Pantoea ananatis*

A DNA fragment comprising the dca gene which is derived from *Pantoea ananatis* and which encodes a gene having 4-hydroxybenzoate decarboxylase activity was amplified by the PCR method as described below.

In the PCR, the following set of primers was synthesized based on SEQ ID NO: 74 (the dca gene of *Pantoea ananatis*) with the use of "394 DNA/RNA Synthesizer" made by Applied Biosystems for cloning of the dca gene, and was used.

Primers for dca Gene Amplification

```
                                         (SEQ ID NO: 75)
(a-26);
5'-CTCT CATATG AGTAGATTACTGTTAATTTCATTCGTAC-3'

(SEQ ID NO: 76)
(b-26);
5'-CTCT CATATG TTACTTAGCTAACAGAGGAGGG-3'
```

Primers (a-26) and (b-26) each have an NdeI restriction enzyme site added thereto.

(3-4) Conditions

As the template DNA for *Corynebacterium glutamicum*, the chromosomal DNA extracted from *Corynebacterium glutamicum* R was used.

For *Escherichia coli*, the chromosomal DNA extracted from *Escherichia coli* K12 MG1655 was used.

For *Pseudomonas putida*, the chromosomal DNA extracted from *Pseudomonas putida* ATCC 47054 obtained from American Type Culture Collection (ATCC) was used.

For *Acinetobacter baumannii*, the chromosomal DNA extracted from *Acinetobacter baumannii* JCM 6841 obtained from Japan Collection of Microorganisms (JCM) was used.

For *Azotobacter vinelandii*, the chromosomal DNA extracted from *Azotobacter vinelandii* ATCC 9104 obtained from American Type Culture Collection (ATCC) was used.

For *Chromohalobacter salexigens*, the chromosomal DNA extracted from *Chromohalobacter salexigens* ATCC BAA-138 obtained from American Type Culture Collection (ATCC) was used.

For *Citrobacter youngae*, the chromosomal DNA extracted from *Citrobacter youngae* ATCC 29220 obtained from American Type Culture Collection (ATCC) was used.

For *Marinobacter aquaeolei*, the *Marinobacter aquaeolei* chromosomal DNA obtained from American Type Culture Collection (ATCC) (catalog No. 700491D-5) was used.

For *Marinomonas mediterranea*, the chromosomal DNA extracted from *Marinomonas mediterranea* NBRC 103028 obtained from NITE (National Institute of Technology and Evaluation) Biological Resource Center (NBRC) was used.

For *Pseudoalteromonas haloplanktis*, the chromosomal DNA extracted from *Pseudoalteromonas haloplanktis* NBRC 102225 obtained from NITE (National Institute of Technology and Evaluation) Biological Resource Center (NBRC) was used.

For *Ralstonia eutropha*, the chromosomal DNA extracted from *Ralstonia eutropha* IAM 12368 obtained from Institute of Applied Microbiology Culture Collection (IAM) was used.

For *Shewanella putrefaciens*, the chromosomal DNA extracted from *Shewanella putrefaciens* JCM 20190 obtained from Japan Collection of Microorganisms (JCM) was used.

For *Thiobacillus denitrificans*, the chromosomal DNA extracted from *Thiobacillus denitrificans* ATCC 25259 obtained from American Type Culture Collection (ATCC) was used.

For *Bacillus subtilis*, the chromosomal DNA extracted from *Bacillus subtilis* NBRC 14144 obtained from NITE (National Institute of Technology and Evaluation) Biological Resource Center (NBRC) was used.

For *Bacillus atrophaeus*, the chromosomal DNA extracted from *Bacillus atrophaeus* JCM 9070 obtained from Japan Collection of Microorganisms (JCM) was used.

For *Bacillus subtilis* subsp. *spizizenii*, the chromosomal DNA extracted from *Bacillus subtilis* subsp. *spizizenii* NBRC 101239 obtained from NITE (National Institute of Technology and Evaluation) Biological Resource Center (NBRC) was used.

For *Citrobacter koseri*, the *Citrobacter koseri* chromosomal DNA obtained from American Type Culture Collection (ATCC) (catalog No. BAA-895D-5) was used.

For *Enterobacter aerogenes*, the chromosomal DNA extracted from *Enterobacter aerogenes* NBRC 13534 obtained from NITE (National Institute of Technology and Evaluation) Biological Resource Center (NBRC) was used.

For *Enterobacter cloacae*, the chromosomal DNA extracted from *Enterobacter cloacae* NBRC 13535 obtained from NITE (National Institute of Technology and Evaluation) Biological Resource Center (NBRC) was used.

For *Enterobacter hormaechei*, the chromosomal DNA extracted from *Enterobacter hormaechei* ATCC 49162 obtained from American Type Culture Collection (ATCC) was used.

For *Enterobacter sakazakii*, the *Enterobacter sakazakii* chromosomal DNA obtained from American Type Culture Collection (ATCC) (catalog No. BAA-894D-5) was used.

For *Escherichia coli* W, the chromosomal DNA extracted from *Escherichia coli* W NBRC 13500 obtained from NITE (National Institute of Technology and Evaluation) Biological Resource Center (NBRC) was used.

For *Escherichia fergusonii*, the chromosomal DNA extracted from *Escherichia fergusonii* NBRC 102419 obtained from NITE (National Institute of Technology and Evaluation) Biological Resource Center (NBRC) was used.

For *Paenibacillus polymyxa*, the chromosomal DNA extracted from *Paenibacillus polymyxa* NBRC 15309 obtained from NITE (National Institute of Technology and Evaluation) Biological Resource Center (NBRC) was used.

For *Pantoea ananatis*, the chromosomal DNA extracted from *Pantoea ananatis* LMG 20103 obtained from BCCM/LMG (Belgian Coordinated Collections of Microorganisms/Laboratory for Microbiology, University of Gent) was used.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |

| | |
|---|---|
| 25 mM MgCl$_2$ | 5 µL |
| dNTP Mixture (2.5 mM each) | 8 µL |
| Template DNA | 5 µL (DNA content: 1 µg or less) |
| The above 2 primers*) | 0.5 µL each (final conc.: 1 µM) |
| Sterile distilled water | 25.5 µL |

The above ingredients were mixed, and 50 µL of the reaction mixture was subjected to PCR.
*)For amplification of the aroG gene of *Corynebacterium glutamicum*, a combination of primers (a-10) and (b-10); for amplification of the ubiC gene of *Escherichia coli*, a combination of primers (a-11) and (b-11); for amplification of the ubiC gene of *Pseudomonas putida*, a combination of primers (a-12) and (b-12); for amplification of the ubiC gene of *Acinetobacter baumannii*, a combination of primers (a-29) and (b-29); for amplification of the ubiC gene of *Azotobacter vinelandii*, a combination of primers (a-30) and (b-30); for amplification of the ubiC gene of *Chromohalobacter salexigens*, a combination of primers (a-31) and (b-31); for amplification of the ubiC gene of *Citrobacter koseri*, a combination of primers (a-32) and (b-32); for amplification of the ubiC gene of *Citrobacter youngae*, a combination of primers (a-33) and (b-33); for amplification of the ubiC gene of *Enterobacter cloacae*, a combination of primers (a-34) and (b-34); for amplification of the ubiC gene of *Marinobacter aquaeolei*, a combination of primers (a-35) and (b-35); for amplification of the ubiC gene of *Marinomonas mediterranea*, a combination of primers (a-36) and (b-36); for amplification of the ubiC gene of *Pantoea ananatis*, a combination of primers (a-37) and (b-37); for amplification of the ubiC gene of *Pseudoalteromonas haloplanktis*, a combination of primers (a-38) and (b-38); for amplification of the ubiC gene of *Ralstonia eutropha*, a combination of primers (a-39) and (b-39); for amplification of the ubiC gene of *Shewanella putrefaciens*, a combination of primers (a-40) and (b-40); for amplification of the ubiC gene of *Thiobacillus denitrificans*, a combination of primers (a-41) and (b-41); for amplification of the bsdBCD gene of *Bacillus subtilis*, a combination of primers (a-13) and (b-13); for amplification of the dca gene of *Bacillus atrophaeus*, a combination of primers (a-16) and (b-16); for amplification of the dca gene of *Bacillus subtilis* subsp. *spizizenii*, a combination of primers (a-17) and (b-17); for amplification of the dca gene of *Citrobacter koseri*, a combination of primers (a-18) and (b-18); for amplification of the dca gene of *Enterobacter aerogenes*, a combination of primers (a-19) and (b-19); for amplification of the dca gene of *Enterobacter cloacae*, a combination of primers (a-20) and (b-20); for amplification of the dca gene of *Enterobacter hormaechei*, a combination of primers (a-21) and (b-21); for amplification of the dca gene of *Enterobacter sakazakii*, a combination of primers (a-22) and (b-22); for amplification of the dca gene of *Escherichia coli* W, a combination of primers (a-23) and (b-23); for amplification of the dca gene of *Escherichia fergusonii*, a combination of primers (a-24) and (b-24); for amplification of the dca gene of *Paenibacillus polymyxa*, a combination of primers (a-25) and (b-25); and for amplification of the dca gene of *Pantoea ananatis*, a combination of primers (a-26) and (b-26) were used.

PCR Cycle:
Denaturation step: 94° C., 60 seconds
Annealing step: 52° C., 60 seconds
Extension step: 72° C.

| | |
|---|---|
| *Corynebacterium glutamicum* aroG gene | 84 seconds |
| *Escherichia coli* ubiC gene | 30 seconds |
| *Pseudomonas putida* ubiC gene | 33 seconds |
| *Acinetobacter baumannii* ubiC gene | 31 seconds |
| *Azotobacter vinelandii* ubiC gene | 33 seconds |
| *Chromohalobacter salexigens* ubiC gene | 33 seconds |
| *Citrobacter koseri* ubiC gene | 30 seconds |
| *Citrobacter youngae* ubiC gene | 30 seconds |
| *Enterobacter cloacae* ubiC gene | 30 seconds |
| *Marinobacter aquaeolei* ubiC gene | 34 seconds |
| *Marinomonas mediterranea* ubiC gene | 32 seconds |
| *Pantoea ananatis* ubiC gene | 31 seconds |
| *Pseudoalteromonas haloplanktis* ubiC gene | 33 seconds |
| *Ralstonia eutropha* ubiC gene | 40 seconds |
| *Shewanella putrefaciens* ubiC gene | 34 seconds |
| *Thiobacillus denitrificans* ubiC gene | 34 seconds |
| *Bacillus subtilis* bsdBCD gene | 137 seconds |
| *Bacillus atrophaeus* dca gene | 135 seconds |
| *Bacillus subtilis* subsp. *spizizenii* dca gene | 137 seconds |
| *Citrobacter koseri* dca gene | 136 seconds |
| *Enterobacter aerogenes* dca gene | 136 seconds |
| *Enterobacter cloacae* dca gene | 135 seconds |
| *Enterobacter hormaechei* dca gene | 141 seconds |
| *Enterobacter sakazakii* dca gene | 137 seconds |
| *Escherichia coli* W dca gene | 136 seconds |
| *Escherichia fergusonii* dca gene | 136 seconds |
| *Paenibacillus polymyxa* dca gene | 138 seconds |
| *Pantoea ananatis* dca gene | 139 seconds |

A cycle consisting of the above 3 steps was repeated 30 times.

With the use of 10 µL of the reaction mixture produced above, 0.8% agarose gel electrophoresis was performed. As a result, detected were an about 1.4-kb DNA fragment in the case of the *Corynebacterium glutamicum* aroG gene, an about 0.5-kb DNA fragment in the case of the *Escherichia coli* ubiC gene, an about 0.6-kb DNA fragment in the case of the *Pseudomonas putida* ubiC gene, an about 0.5-kb DNA fragment in the case of the *Acinetobacter baumannii* ubiC gene, an about 0.6-kb DNA fragment in the case of the *Azotobacter vinelandii* ubiC gene, an about 0.6-kb DNA fragment in the case of the *Chromohalobacter salexigens* ubiC gene, an about 0.5-kb DNA fragment in the case of the *Citrobacter koseri* ubiC gene, an about 0.5-kb DNA fragment in the case of the *Citrobacter youngae* ubiC gene, an about 0.5-kb DNA fragment in the case of the *Enterobacter cloacae* ubiC gene, an about 0.6-kb DNA fragment in the case of the *Marinobacter aquaeolei* ubiC gene, an about 0.5-kb DNA fragment in the case of the *Marinomonas mediterranea* ubiC gene, an about 0.5-kb DNA fragment in the case of the *Pantoea ananatis* ubiC gene, an about 0.5-kb DNA fragment in the case of the *Pseudoalteromonas haloplanktis* ubiC gene, an about 0.7-kb DNA fragment in the case of the *Ralstonia eutropha* ubiC gene, an about 0.6-kb DNA fragment in the case of the *Shewanella putrefaciens* ubiC gene, an about 0.6-kb DNA fragment in the case of the *Thiobacillus denitrificans* ubiC gene, an about 2.3-kb DNA fragment in the case of the *Bacillus subtilis* bsdBCD gene, an about 2.3-kb DNA fragment in the case of the *Bacillus atrophaeus* bsdBCD gene, an about 2.3-kb DNA fragment in the case of the *Bacillus subtilis* subsp. *spizizenii* dca gene, an about 2.3-kb DNA fragment in the case of the *Citrobacter koseri* dca gene, an about 2.3-kb DNA fragment in the case of the *Enterobacter aerogenes* dca gene, an about 2.3-kb DNA fragment in the case of the *Enterobacter cloacae* dca gene, an about 2.4-kb DNA fragment in the case of the *Enterobacter hormaechei* dca gene, an about 2.3-kb DNA fragment in the case of the *Enterobacter sakazakii* dca gene, an about 2.3-kb DNA fragment in the case of the *Escherichia coli* W dca gene, an about 2.3-kb DNA fragment in the case of the *Escherichia fergusonii* dca gene, an about 2.3-kb DNA fragment in the case of the *Paenibacillus polymyxa* dca gene, and an about 2.3-kb DNA fragment in the case of the *Pantoea ananatis* dca gene.

(4) Construction of Phenol-Producing Gene Expression Plasmids Cloning of Phenol-Producing Genes to pCRB209

10 µL of the about 1.4-kb DNA fragment comprising the aroG gene derived from *Corynebacterium glutamicum*, the about 0.5-kb DNA fragment comprising the ubiC gene derived from *Escherichia coli*, the about 0.6-kb DNA fragment comprising the ubiC gene derived from *Pseudomonas putida*, the about 0.5-kb DNA fragment comprising the ubiC gene derived from *Acinetobacter baumannii*, the about 0.6-kb DNA fragment comprising the ubiC gene derived from *Azotobacter vinelandii*, the about 0.6-kb DNA fragment comprising the ubiC gene derived from *Chromohalobacter salexigens*, the about 0.5-kb DNA fragment comprising the ubiC gene derived from *Citrobacter koseri*, the about 0.5-kb DNA fragment comprising the ubiC gene derived from *Citrobacter youngae*, the about 0.5-kb DNA fragment comprising the ubiC gene derived from *Enterobacter cloacae*, the about 0.6-kb DNA fragment comprising the ubiC gene derived from *Marinobacter aquaeolei*, the about 0.5-kb DNA fragment comprising the ubiC gene derived from *Marinomonas mediterranea*, the about 0.5-kb DNA fragment comprising the ubiC gene derived from *Pantoea ananatis*, the about 0.5-kb DNA fragment comprising the ubiC gene derived from *Pseudoalteromonas haloplanktis*, the about 0.7-kb DNA fragment comprising the ubiC gene derived from *Ralstonia eutropha*, the about 0.6-kb DNA fragment comprising the ubiC gene derived from *Shewanella putrefaciens*, the about 0.6-kb DNA fragment comprising the ubiC gene derived from *Thiobacillus denitrificans*, the about 2.3-kb DNA fragment comprising the bsdBCD gene derived from *Bacillus subtilis*, the about 2.3-kb DNA fragment comprising the dca gene derived from *Bacillus atrophaeus*, the about 2.3-kb DNA fragment comprising the dca gene derived from *Bacillus subtilis* subsp. *spizizenii*, the about 2.3-kb DNA fragment comprising the dca gene derived from *Citrobacter koseri*, the about 2.3-kb DNA fragment comprising the dca gene derived from *Enterobacter aerogenes*, the about 2.3-kb DNA fragment comprising the dca gene derived from *Enterobacter cloacae*, the about 2.4-kb DNA fragment comprising the dca gene derived from *Enterobacter hormaechei*, the about 2.3-kb DNA fragment comprising the dca gene derived from *Enterobacter sakazakii*, the about 2.3-kb DNA fragment comprising the dca gene derived from *Escherichia coli* W, the about 2.3-kb DNA fragment comprising the dca gene derived from *Escherichia fergusonii*, the about 2.3-kb DNA fragment comprising the dca gene derived from *Paenibacillus polymyxa*, or the about 2.3-kb DNA fragment comprising the dca gene derived from *Pantoea ananatis*, each amplified by the PCR in the above (3), and 2 µL of the cloning vector pCRB209 comprising promoter PgapA were each cut with the use of restriction enzyme NdeI, and were processed at 70° C. for 10 minutes for deactivation of the restriction enzyme. Both were mixed, and 1 µL of T4 DNA ligase 10× buffer solution and 1 unit of T4 DNA ligase (made by Takara Bio, Inc.) were added thereto. Sterile distilled water was added thereto so that the total volume was 10 µL, and the mixture was allowed to react at 15° C. for 3 hours for ligation. The resulting liquid was named Ligation Liquid G, H, I, AA, AB, AC, AD, AE, AF, AG, AH, AI, AJ, AK, AL, AM, J, O, P, Q, R, S, T, U, V, W, X or Y.

With the use of each of the obtained 28 kinds of Ligation Liquids G, H, I, AA, AB, AC, AD, AE, AF, AG, AH, AI, AJ, AK, AL, AM, J, O, P, Q, R, S, T, U, V, W, X and Y, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture and cut with the use of restriction enzyme to confirm the inserted fragment. As a result, in addition to an about 5.1-kb DNA fragment of the plasmid pCRB209, confirmed were an about 1.4-kb inserted fragment in the case of the aroG gene derived from *Corynebacterium glutamicum* (Ligation Liquid G), an about 0.5-kb inserted fragment in the case of the ubiC gene derived from *Escherichia coli* (Ligation Liquid H), an about 0.6-kb inserted fragment in the case of the ubiC gene derived from *Pseudomonas putida* (Ligation Liquid I), an about 0.5-kb inserted fragment in the case of the ubiC gene derived from *Acinetobacter baumannii* (Ligation Liquid AA), an about 0.6-kb inserted fragment in the case of the ubiC gene derived from *Azotobacter vinelandii* (Ligation Liquid AB), an about 0.6-kb inserted fragment in the case of the ubiC gene derived from *Chromohalobacter salexigens* (Ligation Liquid AC), an about 0.5-kb inserted fragment in the case of the ubiC gene derived from *Citrobacter koseri* (Ligation Liquid AD), an about 0.5-kb inserted fragment in the case of the ubiC gene derived from *Citrobacter youngae* (Ligation Liquid AE), an about 0.5-kb inserted fragment in the case of the ubiC gene derived from *Enterobacter cloacae* (Ligation Liquid AF), an about 0.6-kb inserted fragment in the case of the ubiC gene derived from *Marinobacter aquaeolei* (Ligation Liquid AG), an about 0.5-kb inserted fragment in the case of the ubiC gene derived from *Marinomonas mediterranea* (Ligation Liquid AH), an about 0.5-kb inserted fragment in the case of the ubiC gene derived from *Pantoea ananatis* (Ligation Liquid AI), an about 0.5-kb inserted fragment in the case of the ubiC gene derived from *Pseudoalteromonas haloplanktis* (Ligation Liquid AJ), an about 0.7-kb inserted fragment in the case of the ubiC gene derived from *Ralstonia eutropha* (Ligation Liquid AK), an about 0.6-kb inserted fragment in the case of the ubiC gene derived from *Shewanella putrefaciens* (Ligation Liquid AL), an about 0.6-kb inserted fragment in the case of the ubiC gene derived from *Thiobacillus denitrificans* (Ligation Liquid AM), an about 2.3-kb inserted fragment in the case of the bsdBCD gene derived from *Bacillus subtilis* (Ligation Liquid J), an about 2.3-kb inserted fragment in the case of the dca gene derived from *Bacillus atrophaeus* (Ligation Liquid 0), an about 2.3-kb inserted fragment in the case of the dca gene derived from *Bacillus subtilis* subsp. *spizizenii* (Ligation Liquid P), an about 2.3-kb inserted fragment in the case of the dca gene derived from *Citrobacter koseri* (Ligation Liquid Q), an about 2.3-kb inserted fragment in the case of the dca gene derived from *Enterobacter aerogenes* (Ligation Liquid R), an about 2.3-kb inserted fragment in the case of the dca gene derived from *Enterobacter cloacae* (Ligation Liquid S), an about 2.4-kb inserted fragment in the case of the dca gene derived from *Enterobacter hormaechei* (Ligation Liquid T), an about 2.3-kb inserted fragment in the case of the dca gene derived from *Enterobacter sakazakii* (Ligation Liquid U), an about 2.3-kb inserted fragment in the case of the dca gene derived from *Escherichia coli* W (Ligation Liquid V), an about 2.3-kb inserted fragment in the case of the dca gene derived from *Escherichia fergusonii* (Ligation Liquid W), an about 2.3-kb inserted fragment in the case of the dca gene derived from *Paenibacillus polymyxa* (Ligation Liquid X), and an about 2.3-kb inserted fragment in the case of the dca gene derived from *Pantoea ananatis* was (Ligation Liquid Y).

The plasmid comprising the aroG gene derived from *Corynebacterium glutamicum* was named pCRB209-aroG/CG, the plasmid comprising the ubiC gene derived from *Escherichia coli* was named pCRB209-ubiC/EC, the plasmid comprising the ubiC gene derived from *Pseudomonas putida* was named pCRB209-ubiC/PP, the plasmid comprising the ubiC gene derived from *Acinetobacter baumannii* was named pCRB209-ubiC/ACB, the plasmid comprising the ubiC gene derived from *Azotobacter vinelandii* was named pCRB209-ubiC/AVN, the plasmid comprising the ubiC gene derived from *Chromohalobacter salexigens* was named pCRB209-ubiC/CSA, the plasmid comprising the ubiC gene derived from *Citrobacter koseri* was named pCRB209-ubiC/CKO, the plasmid comprising the ubiC gene derived from *Citrobacter youngae* was named pCRB209-ubiC/CIT, the plasmid comprising the ubiC gene derived from *Enterobacter cloacae* was named pCRB209-ubiC/ECL, the plasmid comprising the ubiC gene derived from *Marinobacter aquaeolei* was named pCRB209-ubiC/MAQ, the plasmid comprising the ubiC gene derived from *Marinomonas mediterranea* was named pCRB209-ubiC/MME, the plasmid comprising the ubiC gene derived from *Pantoea ananatis* was named pCRB209-ubiC/PAM, the plasmid comprising the ubiC gene derived from *Pseudoalteromonas haloplanktis* was named pCRB209-ubiC/PHA, the plasmid comprising the ubiC gene derived from *Ralstonia eutropha* was named pCRB209-ubiC/REH, the plasmid comprising the ubiC gene derived from *Shewanella putrefaciens* was named pCRB209-ubiC/SPC, the plasmid comprising the ubiC gene derived from *Thiobacillus denitrificans* was named pCRB209-ubiC/TBD, the plasmid comprising the bsdBCD gene derived from *Bacillus subtilis* was named pCRB209-bsdBCD/BS, the plasmid comprising the dca gene derived from *Bacillus atrophaeus* was named pCRB209-dca/BAE, the plasmid comprising the dca gene derived from *Bacillus subtilis* subsp. *spizizenii* was named pCRB209-dca/BSS, the plasmid comprising the dca gene derived from *Citrobacter koseri* was named pCRB209-dca/CKO, the plasmid comprising the dca gene derived from *Enterobacter aerogenes* was named pCRB209-dca/EAE, the plasmid comprising the dca gene derived from *Enterobacter cloacae* was named pCRB209-dca/ECL, the plasmid comprising the dca gene derived from *Enterobacter hormaechei* was named pCRB209-dca/EHO, the plasmid comprising the dca gene derived from *Enterobacter sakazakii* was named pCRB209-dca/ESA, the plasmid comprising the dca gene derived from *Escherichia coli* W was named pCRB209-dca/ECK, the plasmid comprising the dca gene derived from *Escherichia fergusonii* was named pCRB209-dca/EFE, the plasmid comprising the dca gene derived from *Paenibacillus polymyxa* was named pCRB209-dca/PPY, and the plasmid comprising the dca gene derived from *Pantoea ananatis* was named pCRB209-dca/PAM.

The construct of the plasmid pCRB209-aroG/CG comprising the aroG gene derived from *Corynebacterium glutamicum*, the plasmid pCRB209-ubiC/EC comprising the ubiC gene derived from *Escherichia coli*, the plasmid pCRB209-ubiC/PP comprising the ubiC gene derived from *Pseudomonas putida*, and the plasmid pCRB209-bsdBCD/BS comprising the bsdBCD gene derived from *Bacillus subtilis* are shown in FIG. 1.

Cloning of Phenol-Producing Genes to pCRB1

The above plasmids pCRB209-ubiC/EC, pCRB209-ubiC/PP, pCRB209-ubiC/ACB, pCRB209-ubiC/AVN, pCRB209-ubiC/CSA, pCRB209-ubiC/CKO, pCRB209-ubiC/CIT, pCRB209-ubiC/ECL, pCRB209-ubiC/MAQ, pCRB209-ubiC/MME, pCRB209-ubiC/PAM, pCRB209-ubiC/PHA and pCRB209-ubiC/SPC were cut with the use of a restriction enzyme SalI. After agarose gel electrophoresis, an about 1.5-kb DNA fragment in which a gapA promoter, a ubiC gene derived from *Escherichia coli*, and a terminator sequence were ligated; an about 1.6-kb DNA fragment in which a gapA promoter, a ubiC gene derived from *Pseudomonas putida*, and a terminator sequence were ligated; an about 1.5-kb DNA fragment in which a gapA promoter, a ubiC gene derived from *Acinetobacter baumannii*, and a terminator sequence were ligated; an about 1.6-kb DNA fragment in which a gapA promoter, a ubiC gene derived from *Azotobacter vinelandii*, and a terminator sequence were ligated; an about 1.6-kb DNA fragment in which a gapA promoter, a ubiC gene derived from *Chromohalobacter salexigens*, and a terminator sequence were ligated; an about 1.5-kb DNA fragment in which a gapA promoter, a ubiC gene derived from *Citrobacter koseri*, and a terminator sequence were ligated; an about 1.5-kb DNA fragment in which a gapA promoter, a ubiC gene derived from *Citrobacter youngae*, and a terminator sequence were ligated; an about 1.5-kb DNA fragment in which a gapA promoter, a ubiC gene derived from *Enterobacter cloacae*, and a terminator sequence were ligated; an about 1.6-kb DNA fragment in which a gapA promoter, a ubiC gene derived from *Marinobacter aquaeolei*, and a terminator sequence were ligated; an about 1.5-kb DNA fragment in which a gapA promoter, a ubiC gene derived from *Marinomonas mediterranea*, and a terminator sequence were ligated; an about 1.5-kb DNA fragment in which a gapA promoter, a ubiC gene derived from *Pantoea ananatis*, and a terminator sequence were ligated; an about 1.5-kb DNA fragment in which a gapA promoter, a ubiC gene derived from *Pseudoalteromonas haloplanktis*, and a terminator sequence were ligated; or an about 1.6-kb DNA fragment in which a gapA promoter, a ubiC gene derived from *Shewanella putrefaciens*, and a terminator sequence were ligated; each of which was recovered from the agarose gel with the use of QIAquick Gel Extraction Kit (made by QIAGEN), and an about 4.1-kb DNA fragment obtained by SalI digestion of the cloning vector pCRB1, followed by 10 min-treatment at 70° C. for deactivation of SalI (Nakata, K. et al., Vectors for the genetics engineering of corynebacteria; in Saha, B. C. (ed.): Fermentation Biotechnology, ACS Symposium Series 862. Washington, American Chemical Society: 175-191 (2003)) were mixed. To this, 1 µL of T4 DNA ligase 10× buffer solution and 1 unit of T4 DNA ligase (made by Takara Bio, Inc.) were added. Sterile distilled water was added thereto so that the total volume was 10 µL, and the mixture was allowed to react at 15° C. for 3 hours for ligation. The resulting liquids were named Ligation Liquids K, L, AN, AO, AP, AQ, AR, AS, AT, AU, AV, AW, and AX.

Similarly, the above-mentioned plasmids pCRB209-ubiC/REH and pCRB209-ubiC/TBD were cut with the use of a restriction enzyme BamHI. After agarose gel electrophoresis, an about 1.7-kb DNA fragment in which a gapA promoter, a ubiC gene derived from *Ralstonia eutropha*, and a terminator sequence were ligated; or an about 1.6-kb DNA fragment in which a gapA promoter, a ubiC gene derived from *Thiobacillus denitrificans*, and a terminator sequence were ligated; both of which were recovered from the agarose gel with the use of QIAquick Gel Extraction Kit (made by QIAGEN), and an about 4.1-kb DNA fragment obtained by BamHI digestion of the cloning vector pCRB1, followed by 10 min-treatment at 70° C. for deactivation of BamHI (Nakata, K. et al., Vectors for the genetics engineering of corynebacteria; in Saha, B. C. (ed.): Fermentation Biotechnology, ACS Symposium Series 862. Washington, American Chemical Society: 175-191 (2003)) were mixed. To this, 1 µL of T4 DNA ligase 10× buffer solution and 1 unit of T4 DNA ligase (made by Takara Bio, Inc.) were added. Sterile distilled water was added thereto so that the total volume was 10 µL, and the mixture was allowed to react at 15° C. for 3 hours for ligation. The resulting liquids were named Ligation Liquids AY and AZ.

With use of each of the obtained Ligation Liquids K, L, AN, AO, AP, AQ, AR, AS, AT, AU, AV, AW, AX, AY and AZ, *Escherichia coli* JM109 was transformed by the calcium chloride method (Journal of Molecular Biology, 53, 159 (1970)) and was applied to LB agar medium (1% of polypeptone, 0.5% of yeast extract, 0.5% of sodium chloride, and 1.5% of agar) containing 50 µg/mL of chloramphenicol.

A growing strain on the culture medium was subjected to liquid culture in the usual manner. Plasmid DNA was extracted from the culture medium and cut with the use of restriction enzyme SalI or BamHI to confirm inserted fragment. As a result, in addition to an about 4.1-kb DNA fragment of the plasmid pCRB1, confirmed were an about 1.5-kb inserted fragment in the case of the ubiC gene derived from *Escherichia coli* (Ligation Liquid K), an about 1.6-kb inserted fragment in the case of the ubiC gene derived from *Pseudomonas putida* (Ligation Liquid L), an about 1.5-kb inserted fragment in the case of the ubiC gene derived from *Acinetobacter baumannii* (Ligation Liquid AN), an about 1.6-kb inserted fragment in the case of the ubiC gene derived from *Azotobacter vinelandii* (Ligation Liquid AO), an about 1.6-kb inserted fragment in the case of the ubiC gene derived from *Chromohalobacter salexigens* (Ligation Liquid AP), an about 1.5-kb inserted fragment in the case of the ubiC gene derived from *Citrobacter koseri* (Ligation Liquid AQ), an about 1.5-kb inserted fragment in the case of the ubiC gene derived from *Citrobacter youngae* (Ligation Liquid AR), an about 1.5-kb inserted fragment in the case of the ubiC gene derived from *Enterobacter cloacae* (Ligation Liquid AS), an about 1.6-kb inserted fragment in the case of the ubiC gene derived from *Marinobacter aquaeolei* (Ligation Liquid AT), an about 1.5-kb inserted fragment in the case of the ubiC gene derived from *Marinomonas mediterranea* (Ligation Liquid AU), an about 1.5-kb inserted fragment in the case of the ubiC gene derived from *Pantoea ananatis* (Ligation Liquid AV), an about 1.5-kb inserted fragment in the case of the ubiC gene derived from *Pseudoalteromonas haloplanktis* (Ligation Liquid AW), an about 1.7-kb inserted fragment in the case of the ubiC gene derived from *Ralstonia eutropha* (Ligation Liquid AY), an about 1.6-kb inserted fragment in the case of the ubiC gene derived from *Shewanella putrefaciens* (Ligation Liquid AX), and an about 1.6-kb inserted fragment in the case of the ubiC gene derived from *Thiobacillus denitrificans* (Ligation Liquid AZ).

Figure 2:
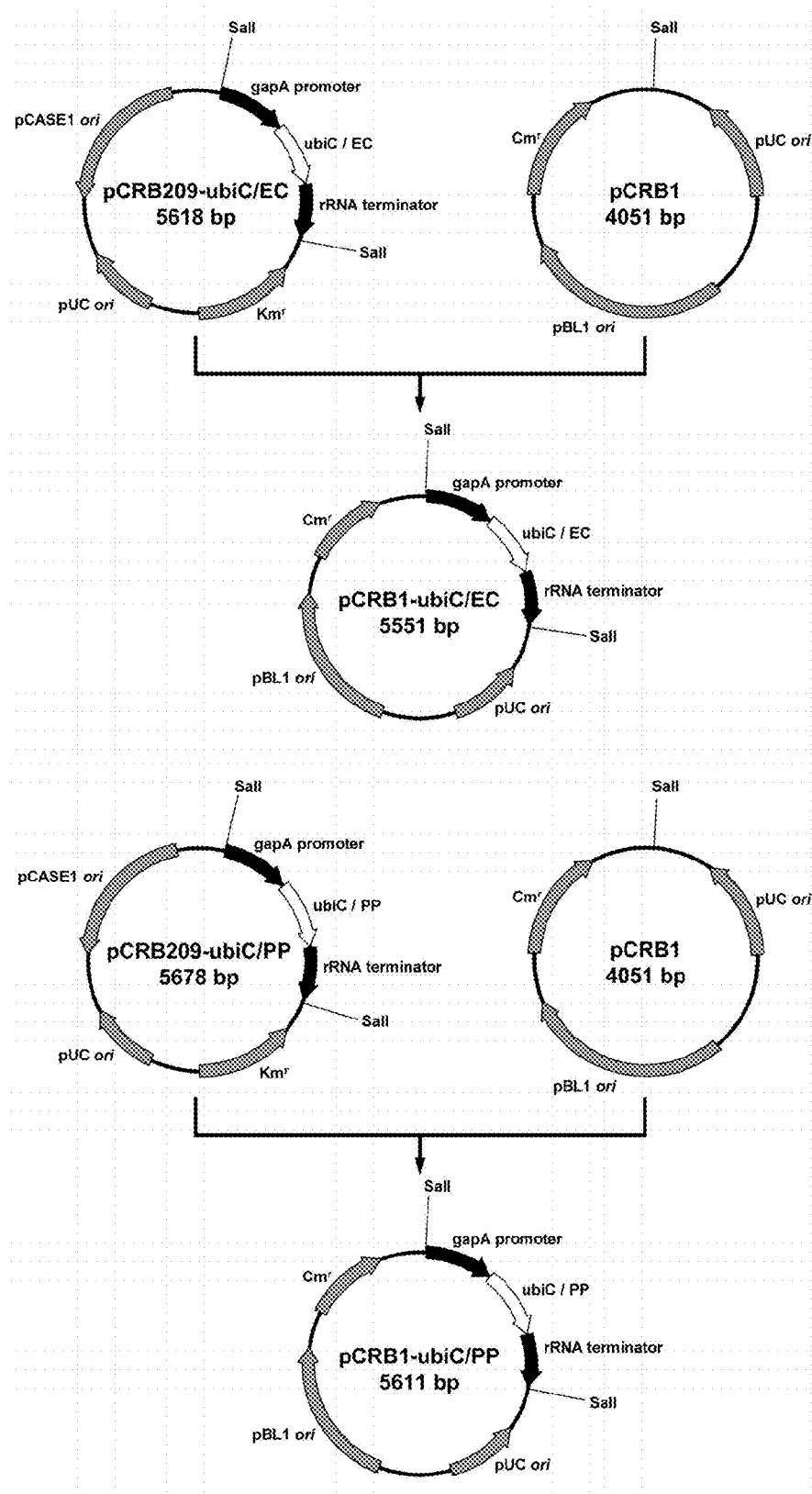
FIG. 2 shows the construct of various plasmids used in Examples.

The plasmid comprising the ubiC gene derived from *Escherichia coli* was named pCRB1-ubiC/EC, and the plasmid comprising the ubiC gene derived from *Pseudomonas putida* was named pCRB1-ubiC/PP (FIG. 2). The plasmid comprising the ubiC gene derived from *Acinetobacter baumannii* was named pCRB1-ubiC/ACB, the plasmid comprising the ubiC gene derived from *Azotobacter vinelandii* was named pCRB1-ubiC/AVN, the plasmid comprising the ubiC gene derived from *Chromohalobacter salexigens* was named pCRB1-ubiC/CSA, the plasmid comprising the ubiC gene derived from *Citrobacter koseri* was named pCRB1-ubiC/CKO, the plasmid comprising the ubiC gene derived from *Citrobacter youngae* was named pCRB1-ubiC/CIT, the plasmid comprising the ubiC gene derived from *Enterobacter cloacae* was named pCRB1-ubiC/ECL, the plasmid comprising the ubiC gene derived from *Marinobacter aquaeolei* was named pCRB1-ubiC/MAQ, the plasmid comprising the ubiC gene derived from *Marinomonas mediterranea* was named pCRB1-ubiC/MME, the plasmid comprising the ubiC gene derived from *Pantoea ananatis* was named pCRB1-ubiC/PAM, the plasmid comprising the ubiC gene derived from *Pseudoalteromonas haloplanktis* was named pCRB1-ubiC/PHA, the plasmid comprising the ubiC gene derived from *Ralstonia eutropha* was named pCRB1-ubiC/REH, the plasmid comprising the ubiC gene derived from *Shewanella putrefaciens* was named pCRB1-ubiC/SPC, and the plasmid comprising the ubiC gene derived from *Thiobacillus denitrificans* was named pCRB1-ubiC/TBD.

Cloning of Phenol-Producing Gene to pCRB15

The above plasmid pCRB209-aroG/CG was cut with the use of a restriction enzyme BamHI. After agarose gel electrophoresis, an about 2.4-kb DNA fragment recovered from the agarose gel with the use of QIAquick Gel Extraction Kit (made by QIAGEN), in which fragment a gapA promoter, an aroG gene derived from *Corynebacterium glutamicum*, and a terminator sequence were ligated, and an about 3.8-kb DNA fragment obtained by BamHI digestion of the plasmid pCRB15, followed by 10 min-treatment at 70° C. for deactivation of BamHI were mixed. To this, 1 µL of T4 DNA ligase 10× buffer solution and 1 unit of T4 DNA ligase (made by Takara Bio, Inc.) were added. Sterile distilled water was added thereto so that the total volume was 10 µL, and the mixture was allowed to react at 15° C. for 3 hours for ligation. This was named Ligation Liquid M.

With the use of the Ligation Liquid M, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 25 µg/mL of zeocin.

A growing strain on the culture medium was subjected to liquid culture in the usual manner. Plasmid DNA was extracted from the culture and cut with the use of restriction enzyme BamHI to confirm inserted fragment. As a result, in addition to an about 3.8-kb DNA fragment of the plasmid pCRB15, an about 2.4-kb inserted fragment of the aroG gene derived from *Corynebacterium glutamicum* (Ligation Liquid M) was confirmed.

Figure 3:
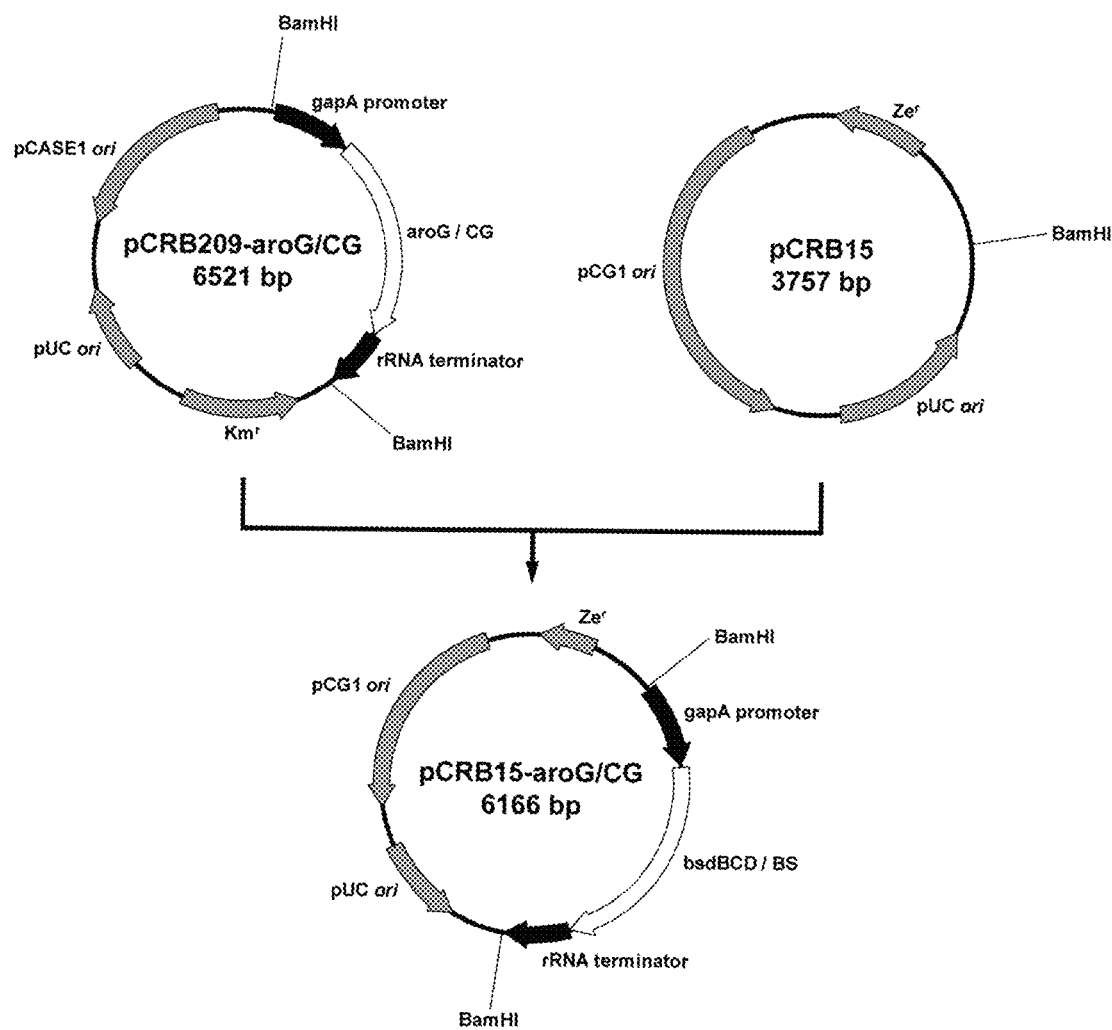
FIG. 3 shows the construct of various plasmids used in Examples.

The plasmid comprising the aroG gene derived from *Corynebacterium glutamicum* was named pCRB15-aroG/CG (FIG. 3).

(5) Construction of Plasmids for *Corynebacterium glutamicum* Chromosomal Gene Disruption Construction of Plasmid for *Corynebacterium glutamicum* pobA Gene Disruption A DNA fragment required for constructing a plasmid for markerless disruption of the pobA gene on the chromosome of *Corynebacterium glutamicum* was amplified by the PCR method as described below.

In the PCR, the following sets of primers were synthesized based on the sequence of *Corynebacterium glutamicum* R with the use of "394 DNA/RNA Synthesizer" made by Applied Biosystems, and were used.

Primers for Amplification of pobA-1 Region

```
                                          (SEQ ID NO: 40)
(a-14);
5'-CTCT TCTAGA GAAACGATCAAGTGCACCAG-3'

(SEQ ID NO: 41)
(b-14);
5'-GACACGAGCGTTTATACCTCTAATTGCCACTGGTACGTGG-3'
```

Primer (a-14) has an XbaI restriction enzyme site added thereto.

Primers for Amplification of pobA-2 Region

```
                                          (SEQ ID NO: 42)
(a-15); 5'-GAGGTATAAACGCTCGTGTC-3'

(SEQ ID NO: 43)
(b-15); 5' -CTCT GAGCTC GAGAACACGAACCATACGAG-3'
```

Primer (b-15) has a SacI restriction enzyme site added thereto.

As the template DNA, the chromosomal DNA extracted from *Corynebacterium glutamicum* R was used.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/µL) | 0.5 µL |
| 10× LA PCR ™ Buffer II (Mg²⁺ free) | 5 µL |
| 25 mM MgCl₂ | 5 µL |
| dNTP Mixture (2.5 mM each) | 8 µL |
| Template DNA | 5 µL (DNA content: 1 µg or less) |
| The above 2 primers*⁾ | 0.5 µL each (final conc.: 1 µM) |
| Sterile distilled water | 25.5 µL |

The above ingredients were mixed, and 50 µL of the reaction mixture was subjected to PCR.
*⁾For amplification of the pobA-1 region, a combination of primers (a-14) and (b-14), and for amplification of the pobA-2 region, a combination of primers (a-15) and (b-15) were used.

PCR Cycle:
Denaturation step: 94° C., 60 seconds
Annealing step: 52° C., 60 seconds
Extension step: 72° C.
pobA-1 region: 60 seconds
pobA-2 region: 60 seconds
A cycle consisting of the above 3 steps was repeated 30 times.

Using 10 μL of the above-produced reaction mixture, 0.8% agarose gel electrophoresis was performed. An about 1.0-kb DNA fragment in the case of the *Corynebacterium glutamicum* pobA-1 region, and an about 1.0-kb DNA fragment in the case of the pobA-2 region were detected.

Subsequently, 1 μL each of the pobA-1 region fragment and the pobA-2 region fragment, which were amplified by the above PCR, were mixed and subjected to PCR for ligation.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.
Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| The above 2 fragments*$^)$ | 1 μL each |
| Sterile distilled water | 29.5 μL |

The above ingredients were mixed, and 50 μL of the reaction mixture was subjected to PCR.
*$^)$pobA-1 region fragment and pobA-2 region fragment were used.

PCR Cycle:
  Denaturation step: 95° C., 20 seconds
  Annealing step: 52° C., 5 seconds
  Extension step: 72° C., 50 seconds
  A cycle consisting of the above 3 steps was repeated 30 times.

Further, using, as the template DNA, the obtained fragment in which pobA-1 and pobA-2 were ligated, a pobA deletion fragment was amplified by PCR.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.
Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*$^)$ | 0.5 μL each (final conc.: 1 μM) |
| Sterile distilled water | 25.5 μL |

The above ingredients were mixed, and 50 μL of the reaction mixture was subjected to PCR.
*$^)$For amplification of the pobA deletion fragment, a combination of primers (a-14) and (b-15) was used.

PCR Cycle:
  Denaturation step: 95° C., 20 seconds
  Annealing step: 52° C., 5 seconds
  Extension step: 72° C., 97 seconds
  A cycle consisting of the above 3 steps was repeated 30 times.

Using 10 μL of the above-produced reaction mixture, 0.8% agarose gel electrophoresis was performed, and an about 2.0-kb fragment of the pobA deletion fragment was detected.

10 μL of the about 2.0-kb DNA fragment of the pobA deletion fragment derived from *Corynebacterium glutamicum* R, which was amplified by the above PCR, and 2 μL of an about 4.4-kb plasmid, pCRA725 for markerless chromosomal gene transfection (J. Mol. Microbiol. Biotechnol., Vol. 8, 243-254, 2004 (JP 2006-124440 A)) were each cut with the use of restriction enzymes XbaI and SacI, and processed at 70° C. for 10 minutes for deactivation of the restriction enzymes. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named Ligation Liquid N.

With the use of the Ligation Liquid N, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of restriction enzymes XbaI and SacI to confirm the inserted fragment. As a result, in addition to an about 4.4-kb DNA fragment of the plasmid pCRA725, an about 2.0-kb inserted fragment of the pobA deletion gene derived from *Corynebacterium glutamicum* (Ligation Liquid N) was confirmed.

The plasmid comprising the pobA deletion gene derived from *Corynebacterium glutamicum* was named pCRA725-pobA/CG.

Construction of Plasmid for *Corynebacterium glutamicum* poxF Gene Disruption

A DNA fragment required for constructing a plasmid for markerless disruption of the poxF gene on the chromosome of *Corynebacterium glutamicum* was amplified by the PCR method as described below.

In the PCR, the following sets of primers were synthesized based on the sequence of *Corynebacterium glutamicum* R with the use of "394 DNA/RNA Synthesizer" made by Applied Biosystems, and were used.
Primers for Amplification of poxF-1 Region

```
                                        (SEQ ID NO: 77)
(a-27);
5'-CTCT TCTAGA TACGTCCTAAACACCCGAC-3'

(SEQ ID NO: 78)
(b-27);
5'-GACCAACCATTGCTGACTTGCGTATCCATAGTCAGGCTTC-3'
```

Primer (a-27) has an XbaI restriction enzyme site added thereto.
Primers for Amplification of poxF-2 Region

```
                                        (SEQ ID NO: 79)
(a-28); 5'-CAAGTCAGCAATGGTTGGTC-3'

(SEQ ID NO: 80)
(b-28); 5'-CTCT TCTAGA TGATCAGTACCAAGGGTGAG-3'
```

Primer (b-28) has an XbaI restriction enzyme site added thereto.

As the template DNA, the chromosomal DNA extracted from *Corynebacterium glutamicum* R was used.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.
Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |

-continued

| Template DNA | 5 µL (DNA content: 1 µg or less) |
| The above 2 primers*) | 0.5 µL each (final conc.: 1 µM) |
| Sterile distilled water | 25.5 µL |

The above ingredients were mixed, and 50 µL of the reaction mixture was subjected to PCR.
*)For amplification of the poxF-1 region, a combination of primers (a-27) and (b-27), and for amplification of the poxF-2 region, a combination of primers (a-28) and (b-28) were used.

PCR Cycle:
 Denaturation step: 94° C., 60 seconds
 Annealing step: 52° C., 60 seconds
 Extension step: 72° C.
 poxF-1 region: 50 seconds
 poxF-2 region: 50 seconds
 A cycle consisting of the above 3 steps was repeated 30 times.

Using 10 µL of the above-produced reaction mixture, 0.8% agarose gel electrophoresis was performed. An about 0.8-kb DNA fragment in the case of the *Corynebacterium glutamicum* poxF-1 region, and an about 0.8-kb DNA fragment in the case of the poxF-2 region were detected.

Subsequently, 1 µL each of the poxF-1 region fragment and the poxF-2 region fragment, which were amplified by the above PCR, were mixed and subjected to PCR for ligation.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.
Reaction Mixture:

| TaKaRa LA Taq ™ (5 units/µL) | 0.5 µL |
| 10× LA PCR ™ Buffer II (Mg$^{2+}$ free) | 5 µL |
| 25 mM MgCl$_2$ | 5 µL |
| dNTP Mixture (2.5 mM each) | 8 µL |
| The above 2 fragments*) | 1 µL each |
| Sterile distilled water | 29.5 µL |

The above ingredients were mixed, and 50 µL of the reaction mixture was subjected to PCR.
*)poxF-1 region fragment and poxF-2 region fragment were used.

PCR Cycle:
 Denaturation step: 95° C., 20 seconds
 Annealing step: 52° C., 5 seconds
 Extension step: 72° C., 50 seconds
 A cycle consisting of the above 3 steps was repeated 30 times.

Further, using, as the template DNA, the obtained fragment in which poxF-1 and poxF-2 were ligated, a poxF deletion fragment was amplified by PCR.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.
Reaction Mixture:

| TaKaRa LA Taq ™ (5 units/µL) | 0.5 µL |
| 10× LA PCR ™ Buffer II (Mg$^{2+}$ free) | 5 µL |
| 25 mM MgCl$_2$ | 5 µL |
| dNTP Mixture (2.5 mM each) | 8 µL |
| Template DNA | 5 µL (DNA content: 1 µg or less) |
| The above 2 primers*) | 0.5 µL each (final conc.: 1 µM) |
| Sterile distilled water | 25.5 µL |

The above ingredients were mixed, and 50 µL of the reaction mixture was subjected to PCR.
*)For amplification of the poxF deletion fragment, a combination of primers (a-27) and (b-28) was used.

PCR Cycle:
 Denaturation step: 95° C., 20 seconds
 Annealing step: 52° C., 5 seconds
 Extension step: 72° C., 50 seconds
 A cycle consisting of the above 3 steps was repeated 30 times.

Using 10 µL of the above-produced reaction mixture, 0.8% agarose gel electrophoresis was performed, and an about 1.6-kb fragment of the poxF deletion fragment was detected.

10 µL of the about 1.7-kb DNA fragment of the poxF deletion fragment derived from *Corynebacterium glutamicum* R, which was amplified by the above PCR, and 2 µL of an about 4.4-kb plasmid, pCRA725 for markerless chromosomal gene transfection (J. Mol. Microbiol. Biotechnol., Vol. 8, 243-254, 2004 (JP 2006-124440 A) were each cut with the use of restriction enzyme XbaI, and processed at 70° C. for 10 minutes for deactivation of the restriction enzyme. Both were mixed, and 1 µL of T4 DNA ligase 10× buffer solution and 1 unit of T4 DNA ligase (made by Takara Bio, Inc.) were added thereto. Sterile distilled water was added thereto so that the total volume was 10 µL, and the mixture was allowed to react at 15° C. for 3 hours for ligation. This was named Ligation Liquid Z.

With the use of the Ligation Liquid Z, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture and cut with the use of restriction enzyme XbaI to confirm the inserted fragment. As a result, in addition to an about 4.4-kb DNA fragment of the plasmid pCRA725, an about 1.7-kb inserted fragment of the pheA deletion gene derived from *Corynebacterium glutamicum* (Ligation Liquid Z) was confirmed.

The plasmid comprising the poxF deletion gene derived from *Corynebacterium glutamicum* was named pCRA725-poxF/CG.

(6) Construction of Strain in which a Gene Associated with Degradation of 4-Hydroxybenzoate is Disrupted Vector pCRA725 for markerless chromosomal gene transfection is a plasmid that cannot be replicated within *Corynebacterium glutamicum* R. With the use of the plasmid pCRA725-pobA/CG, transformation of *Corynebacterium glutamicum* R was performed by electroporation (Agric. Biol. Chem., Vol. 54, 443-447 (1990) and Res. Microbiol., Vol. 144, 181-185 (1993)), and the strain was applied to A agar medium (A liquid medium and 1.5% agar) containing 50 µg/mL of kanamycin. The single crossover strain obtained on the above medium was applied to BT agar medium (2 g of (NH$_2$)$_2$CO, 7 g of (NH$_4$)$_2$SO$_4$, 0.5 g of KH$_2$PO$_4$, 0.5 g of K$_2$HPO$_4$, 0.5 g of MgSO$_4$.7H$_2$O, 1 mL of 0.06% (w/v) Fe$_2$SO$_4$.7H$_2$O+0.042% (w/v) MnSO$_4$.2H$_2$O, 1 mL of 0.02% (w/v) biotin solution, 2 mL of 0.01% (w/v) thiamin solution dissolved in 1 L of distilled water, and 1.5% agar) containing 10% (w/v) sucrose.

In the case of a strain having a single crossover of the plasmid pCRA725-pobA/CG with the homologous region on the chromosome, the strain shows kanamycin resistance resulting from the expression of the kanamycin resistance gene on the pCRA725-pobA/CG and mortality on a culture medium containing sucrose resulting from the expression of the *Bacillus subtilis* sacR-sacB gene. In the case of a strain having a double crossover of the plasmid pCRA725-pobA/CG, the strain shows kanamycin sensitivity resulting from the loss of the kanamycin resistance gene on the pCRA725-pobA/CG and growing ability on a culture medium containing sucrose resulting from the loss of the sacR-sacB gene. The markerless chromosomal gene disruptant shows kanamycin sensitivity and growing ability on a culture medium containing sucrose. Therefore, a strain that showed kanamycin sensitivity and growing ability on a culture medium containing sucrose was selected.

The obtained markerless pobA gene disruptant of *Corynebacterium glutamicum* R was named *Corynebacterium glutamicum* ΔpobA.

Construction of *Corynebacterium glutamicum* pobA and poxF Gene Disruptant

Vector pCRA725 for markerless chromosomal gene transfection is a plasmid that cannot be replicated within *Corynebacterium glutamicum* R. With the use of the plasmid pCRA725-poxF/CG, transformation of *Corynebacterium glutamicum* ΔpobA was performed by electroporation (Agric. Biol. Chem., Vol. 54, 443-447 (1990) and Res. Microbiol., Vol. 144, 181-185 (1993)), and the strain was applied to A agar medium (A liquid medium and 1.5% agar) containing 50 µg/mL of kanamycin. The single crossover strain obtained on the above medium was applied to BT agar medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O+0.042\%$ (w/v) $MnSO_4.2H_2O$, 1 mL of 0.02% (w/v) biotin solution, 2 mL of 0.01% (w/v) thiamin solution dissolved in 1 L of distilled water, and 1.5% agar) containing 10% (w/v) sucrose.

In the case of a strain having a single crossover of the plasmid pCRA725-poxF/CG with the homologous region on the chromosome, the strain shows kanamycin resistance resulting from the expression of the kanamycin resistance gene on the pCRA725-poxF/CG and mortality on a culture medium containing sucrose resulting from the expression of the *Bacillus subtilis* sacR-sacB gene. In the case of a strain having a double crossover of the plasmid pCRA725-poxF/CG, the strain shows kanamycin sensitivity resulting from the loss of the kanamycin resistance gene on the pCRA725-poxF/CG and growing ability on a culture medium containing sucrose resulting from the loss of the sacR-sacB gene. The markerless chromosomal gene disruptant shows kanamycin sensitivity and growing ability on a culture medium containing sucrose. Therefore, a strain that showed kanamycin sensitivity and growing ability on a culture medium containing sucrose was selected.

The obtained markerless poxF gene disruptant of *Corynebacterium glutamicum* ΔpobA was named *Corynebacterium glutamicum* ΔpobAΔpoxF.

(7) Construction of Transgenic Strains for Phenol Production Gene (7-1) Transformation of *Corynebacterium glutamicum* Wild Strain and ΔpobA With the use of the above-described plasmids pCRB1-ubiC/EC and pCRB209-bsdBCD/BS, transformation of *Corynebacterium glutamicum* R or *Corynebacterium glutamicum* ΔpobA was performed by electroporation (Agric. Biol. Chem., Vol. 54, 443-447 (1990) and Res. Microbiol., Vol. 144, 181-185 (1993)), and the strain was applied to A agar medium containing 5 µg/mL of chloramphenicol and 50 µg/mL of kanamycin. These two kinds of plasmids can coexist in *Corynebacterium glutamicum*.

A growing strain on the culture medium was subjected to liquid culture in the usual manner. Plasmid DNA was extracted from the culture and cut with the use of restriction enzymes to confirm the inserted plasmids. As a result, transfection of the above-constructed plasmids pCRB1-ubiC/EC and pCRB209-bsdBCD/BS was confirmed. The obtained transformant of the R strain was named *Corynebacterium glutamicum* PHE11, and the obtained transformant of the ΔpobA strain was named *Corynebacterium glutamicum* PHE13.

With the use of the above-described plasmids pCRB1-ubiC/EC, pCRB209-bsdBCD/BS, and pCRB15-aroG/CG, transformation of *Corynebacterium glutamicum* R or *Corynebacterium glutamicum* ΔpobA was performed by electroporation (Agric. Biol. Chem., Vol. 54, 443-447 (1990) and Res. Microbiol., Vol. 144, 181-185 (1993)), and the strain was applied to A agar medium containing 5 µg/mL of chloramphenicol, 50 µg/mL of kanamycin, and 25 µg/mL of zeocin. These three kinds of plasmids can coexist in *Corynebacterium glutamicum*.

A growing strain on the culture medium was subjected to liquid culture in the usual manner. Plasmid DNA was extracted from the culture and cut with the use of restriction enzymes to confirm the inserted plasmids. As a result, transfection of the above-constructed plasmids pCRB1-ubiC/EC, pCRB209-bsdBCD/BS, and pCRB15-aroG/CG was confirmed. The obtained transformant of the R strain was named *Corynebacterium glutamicum* PHE12, and the obtained transformant of the ΔpobA strain was named *Corynebacterium glutamicum* PHE14.

With the use of the above-described plasmids pCRB1-ubiC/PP and pCRB209-bsdBCD/BS, transformation of *Corynebacterium glutamicum* R or *Corynebacterium glutamicum* ΔpobA was performed by electroporation (Agric. Biol. Chem., Vol. 54, 443-447 (1990) and Res. Microbiol., Vol. 144, 181-185 (1993)), and the strain was applied to A agar medium containing 5 µg/mL of chloramphenicol and 50 µg/mL of kanamycin. These two kinds of plasmids can coexist in *Corynebacterium glutamicum*.

A growing strain on the culture medium was subjected to liquid culture in the usual manner. Plasmid DNA was extracted from the culture and cut with the use of restriction enzymes to confirm the inserted plasmids. As a result, transfection of the above-constructed plasmids pCRB1-ubiC/PP and pCRB209-bsdBCD/BS was confirmed. The obtained transformant of the R strain was named *Corynebacterium glutamicum* PHE15, and the obtained transformant of the ΔpobA strain was named *Corynebacterium glutamicum* PHE17.

With the use of the above-described plasmids pCRB1-ubiC/PP, pCRB209-bsdBCD/BS, and pCRB15-aroG/CG, transformation of *Corynebacterium glutamicum* R or *Corynebacterium glutamicum* ΔpobA was performed by electroporation (Agric. Biol. Chem., Vol. 54, 443-447 (1990) and Res. Microbiol., Vol. 144, 181-185 (1993)), and the strain was applied to A agar medium containing 5 µg/mL of chloramphenicol, 50 µg/mL of kanamycin, and 25 µg/mL of zeocin. These three kinds of plasmids can coexist in *Corynebacterium glutamicum*.

A growing strain on the culture medium was subjected to liquid culture in the usual manner. Plasmid DNA was extracted from the culture and cut with the use of restriction enzymes to confirm the inserted plasmids. As a result, transfection of the above-constructed plasmids pCRB1-ubiC/PP, pCRB209-bsdBCD/BS, and pCRB15-aroG/CG was confirmed. The obtained transformant of the R strain was named *Corynebacterium glutamicum* PHE16, and the obtained transformant of the ΔpobA strain was named *Corynebacterium glutamicum* PHE18.

(7-2) Transformation of *Corynebacterium glutamicum* ΔpobAΔpoxF

With the use of each of various combinations of the above-described plasmids pCRB1-ubiC/PP, pCRB209-bsdBCD/BS, pCRB209-dca/BAE, pCRB209-dca/BSS, pCRB209-dca/CKO, pCRB209-dca/EAE, pCRB209-dca/ECL, pCRB209-dca/EHO, pCRB209-dca/ESA, pCRB209-dca/ECK, pCRB209-dca/EFE, pCRB209-dca/PPY, pCRB209-dca/PAM, and pCRB15-aroG/CG, transformation of *Corynebacterium glutamicum* ΔpobAΔpoxF was performed by electroporation (Agric. Biol. Chem., Vol. 54, 443-447 (1990) and Res. Microbiol., Vol. 144, 181-185 (1993)), and the strain was applied to A agar medium containing 5 µg/mL of chloramphenicol, 50 µg/mL of kanamycin, and 25 µg/mL of zeocin. These three kinds of plasmids (pCRB1, pCRB209, and pCRB15) can coexist in *Corynebacterium glutamicum*.

A growing strain on the culture medium was subjected to liquid culture in the usual manner. Plasmid DNA was extracted from the culture and cut with the use of restriction enzymes to confirm the inserted plasmids. As a result, transfection of the above-constructed plasmids pCRB1-ubiC/PP, pCRB209-bsdBCD/BS, pCRB209-dca/BAE, pCRB209-dca/BSS, pCRB209-dca/CKO, pCRB209-dca/EAE, pCRB209-dca/ECL, pCRB209-dca/EHO, pCRB209-dca/ESA, pCRB209-dca/ECK, pCRB209-dca/EFE, pCRB209-dca/PPY, pCRB209-dca/PAM, and pCRB15-aroG/CG was confirmed.

Among the ΔpobAΔpoxF strains, the strain in which transfection of pCRB1-ubiC/PP, pCRB209-bsdBCD/BS, and pCRB15-aroG/CG had been confirmed was named *Corynebacterium glutamicum* PHE19-1, the strain in which transfection of pCRB1-ubiC/PP, pCRB209-dca/BAE, and pCRB15-aroG/CG had been confirmed was named *Corynebacterium glutamicum* PHE19-2, the strain in which transfection of pCRB1-ubiC/PP, pCRB209-dca/BSS, and pCRB15-aroG/CG had been confirmed was named *Corynebacterium glutamicum* PHE19-3, the strain in which transfection of pCRB1-ubiC/PP, pCRB209-dca/CKO, and pCRB15-aroG/CG had been confirmed was named *Corynebacterium glutamicum* PHE19-4, the strain in which transfection of pCRB1-ubiC/PP, pCRB209-dca/EAE, and pCRB15-aroG/CG had been confirmed was named *Corynebacterium glutamicum* PHE19-5, the strain in which transfection of pCRB1-ubiC/PP, pCRB209-dca/ECL, and pCRB15-aroG/CG had been confirmed was named *Corynebacterium glutamicum* PHE19-6, the strain in which transfection of pCRB1-ubiC/PP, pCRB209-dca/EHO, and pCRB15-aroG/CG had been confirmed was named *Corynebacterium glutamicum* PHE19-7, the strain in which transfection of pCRB1-ubiC/PP, pCRB209-dca/ESA, and pCRB15-aroG/CG had been confirmed was named *Corynebacterium glutamicum* PHE19-8, the strain in which transfection of pCRB1-ubiC/PP, pCRB209-dca/ECK, and pCRB15-aroG/CG had been confirmed was named *Corynebacterium glutamicum* PHE19-9, the strain in which transfection of pCRB1-ubiC/PP, pCRB209-dca/EFE, and pCRB15-aroG/CG had been confirmed was named *Corynebacterium glutamicum* PHE19-10, the strain in which transfection of pCRB1-ubiC/PP, pCRB209-dca/PPY, and pCRB15-aroG/CG had been confirmed was named *Corynebacterium glutamicum* PHE19-11, and the strain in which transfection of pCRB1-ubiC/PP, pCRB209-dca/PAM, and pCRB15-aroG/CG had been confirmed was named *Corynebacterium glutamicum* PHE19-12. With the use of each of various combinations of the above-described plasmids pCRB1-ubiC/EC, pCRB1-ubiC/ACB, pCRB1-ubiC/AVN, pCRB1-ubiC/CSA, pCRB1-ubiC/CKO, pCRB1-ubiC/CIT, pCRB1-ubiC/ECL, pCRB1-ubiC/MAQ, pCRB1-ubiC/MME, pCRB1-ubiC/PAM, pCRB1-ubiC/PHA, pCRB1-ubiC/REH, pCRB1-ubiC/SPC, pCRB1-ubiC/TBD, pCRB209-dca/ECL and pCRB15-aroG/CG, transformation of *Corynebacterium glutamicum* ΔpobAΔpoxF was performed by electroporation (Agric. Biol. Chem., Vol. 54, 443-447 (1990) and Res. Microbiol., Vol. 144, 181-185 (1993)), and the strain was applied to A agar medium containing 5 µg/mL of chloramphenicol, 50 µg/mL of kanamycin, and 25 µg/mL of zeocin. These three kinds of plasmids (pCRB1, pCRB209, and pCRB15) can coexist in *Corynebacterium glutamicum*.

A growing strain on the culture medium was subjected to liquid culture in the usual manner. Plasmid DNA was extracted from the culture and cut with the use of restriction enzymes to confirm the inserted plasmids. As a result, transfection of the above-constructed plasmids pCRB1-ubiC/EC, pCRB1-ubiC/ACB, pCRB1-ubiC/AVN, pCRB1-ubiC/CSA, pCRB1-ubiC/CKO, pCRB1-ubiC/CIT, pCRB1-ubiC/ECL, pCRB1-ubiC/MAQ, pCRB1-ubiC/MME, pCRB1-ubiC/PAM, pCRB1-ubiC/PHA, pCRB1-ubiC/REH, pCRB1-ubiC/SPC, pCRB1-ubiC/TBD, pCRB209-dca/ECL and pCRB15-aroG/CG was confirmed.

Among the ΔpobAΔpoxF strains, the strain in which transfection of pCRB1-ubiC/EC, pCRB209-dca/ECL, and pCRB15-aroG/CG had been confirmed was named *Corynebacterium glutamicum* PHE20-1, the strain in which transfection of pCRB1-ubiC/ACB, pCRB209-dca/ECL, and pCRB15-aroG/CG had been confirmed was named *Corynebacterium glutamicum* PHE20-2, the strain in which transfection of pCRB1-ubiC/AVN, pCRB209-dca/ECL, and pCRB15-aroG/CG had been confirmed was named *Corynebacterium glutamicum* PHE20-3, the strain in which transfection of pCRB1-ubiC/CSA, pCRB209-dca/ECL, and pCRB15-aroG/CG had been confirmed was named *Corynebacterium glutamicum* PHE20-4, the strain in which transfection of pCRB1-ubiC/CKO, pCRB209-dca/ECL, and pCRB15-aroG/CG had been confirmed was named *Corynebacterium glutamicum* PHE20-5, the strain in which transfection of pCRB1-ubiC/CIT, pCRB209-dca/ECL, and pCRB15-aroG/CG had been confirmed was named *Corynebacterium glutamicum* PHE20-6, the strain in which transfection of pCRB1-ubiC/ECL, pCRB209-dca/ECL, and pCRB15-aroG/CG had been confirmed was named *Corynebacterium glutamicum* PHE20-7, the strain in which transfection of pCRB1-ubiC/MAQ, pCRB209-dca/ECL, and pCRB15-aroG/CG had been confirmed was named *Corynebacterium glutamicum* PHE20-8, the strain in which transfection of pCRB1-ubiC/MME, pCRB209-dca/ECL, and pCRB15-aroG/CG had been confirmed was named *Corynebacterium glutamicum* PHE20-9, the strain in which transfection of pCRB1-ubiC/PAM, pCRB209-dca/ECL, and pCRB15-aroG/CG had been confirmed was named *Corynebacterium glutamicum* PHE20-10, the strain in which transfection of pCRB1-ubiC/PHA, pCRB209-dca/ECL, and pCRB15-aroG/CG had been confirmed was named *Corynebacterium glutamicum* PHE20-11, the strain in which transfection of pCRB1-ubiC/REH, pCRB209-dca/ECL, and pCRB15-aroG/CG had been confirmed was named *Corynebacterium glutamicum* PHE20-12, the strain in which transfection of pCRB1-ubiC/SPC, pCRB209-dca/ECL, and pCRB15-aroG/CG had been confirmed was named *Corynebacterium glutamicum* PHE20-13, and the strain in which transfection of pCRB1-ubiC/TBD, pCRB209-dca/ECL, and pCRB15-aroG/CG had been confirmed was named *Corynebacterium glutamicum* PHE20-14.

The outline of gene recombination in the above-described strains is shown in Table 1 below.

*Corynebacterium glutamicum* PHE18 was deposited in Incorporated Administrative Agency National Institute of Technology and Evaluation, NITE Patent Microorganisms Depositary (2-5-8 Kazusakamatari, Kisarazu-shi, Chiba 292-0818 Japan) under Accession Number NITE BP-995 on Oct. 21, 2010.

TABLE 1

Phenol-producing gene transgenic strains

| Strain | Host strain *Corynebacterium glutamicum* | Transfected gene (gene name/origin) | | |
|---|---|---|---|---|
| PHE11 | Wild strain | ubiC/EC | bsdBCD/BS | — |
| PHE12 | | ubiC/EC | bsdBCD/BS | aroG/CG |
| PHE13 | ΔpobA | ubiC/EC | bsdBCD/BS | — |
| PHE14 | | ubiC/EC | bsdBCD/BS | aroG/CG |
| PHE15 | Wild strain | ubiC/PP | bsdBCD/BS | — |
| PHE16 | | ubiC/PP | bsdBCD/BS | aroG/CG |
| PHE17 | ΔpobA | ubiC/PP | bsdBCD/BS | — |
| PHE18 | | ubiC/PP | bsdBCD/BS | aroG/CG |
| PHE19-1 | ΔpobAΔpoxF | ubiC/PP | bsdBCD/BS | aroG/CG |
| PHE19-2 | | ubiC/PP | dca/BAE | aroG/CG |
| PHE19-3 | | ubiC/PP | dca/BSS | aroG/CG |
| PHE19-4 | | ubiC/PP | dca/CKO | aroG/CG |
| PHE19-5 | | ubiC/PP | dca/EAE | aroG/CG |
| PHE19-6 | | ubiC/PP | dca/ECL | aroG/CG |
| PHE19-7 | | ubiC/PP | dca/EHO | aroG/CG |
| PHE19-8 | | ubiC/PP | dca/ESA | aroG/CG |
| PHE19-9 | | ubiC/PP | dca/ECK | aroG/CG |
| PHE19-10 | | ubiC/PP | dca/EFE | aroG/CG |
| PHE19-11 | | ubiC/PP | dca/PPY | aroG/CG |
| PHE19-12 | | ubiC/PP | dca/PAM | aroG/CG |
| PHE20-1 | ΔpobAΔpoxF | ubiC/EC | dca/ECL | aroG/CG |
| PHE20-2 | | ubiC/ACB | dca/ECL | aroG/CG |
| PHE20-3 | | ubiC/AVN | dca/ECL | aroG/CG |
| PHE20-4 | | ubiC/CSA | dca/ECL | aroG/CG |
| PHE20-5 | | ubiC/CKO | dca/ECL | aroG/CG |
| PHE20-6 | | ubiC/CIT | dca/ECL | aroG/CG |
| PHE20-7 | | ubiC/ECL | dca/ECL | aroG/CG |
| PHE20-8 | | ubiC/MAQ | dca/ECL | aroG/CG |
| PHE20-9 | | ubiC/MME | dca/ECL | aroG/CG |
| PHE20-10 | | ubiC/PAM | dca/ECL | aroG/CG |
| PHE20-11 | | ubiC/PHA | dca/ECL | aroG/CG |
| PHE20-12 | | ubiC/REH | dca/ECL | aroG/CG |
| PHE20-13 | | ubiC/SPC | dca/ECL | aroG/CG |
| PHE20-14 | | ubiC/TBD | dca/ECL | aroG/CG |

<Abbreviation for gene origin>
BS; *Bacillus subtilis*
EC; *Escherichia coli*
PP; *Pseudomonas putida*
CG; *Corynebacterium glutamicum*
BAE; *Bacillus atrophaeus*
BSS; *Bacillus subtilis* subsp. *spizizenii*
CKO; *Citrobacter koseri*
EAE; *Enterobacter aerogenes*
ECL; *Enterobacter cloacae*
EHO; *Enterobacter hormaechei*
ESA; *Enterobacter sakazakii*
ECK; *Escherichia coli* W
EFE; *Escherichia fergusonii*
PPY; *Paenibacillus polymyxa*
PAM; *Pantoea ananatis*
ACB; *Acinetobacter baumannii*
AVN; *Azotobacter vinelandii*
CSA; *Chromohalobacter salexigens*
CIT; *Citrobacter youngae*
MAQ; *Marinobacter aquaeolei*
MME; *Marinomonas mediterranea*
PHA; *Pseudoalteromonas haloplanktis*
REH; *Ralstonia eutropha*
SPC; *Shewanella putrefaciens*
TBD; *Thiobacillus denitrificans*
<Gene name>
ubiC; chorismate-pyruvate lyase gene
bsdBCD; 4-hydroxybenzoate decarboxylase gene
aroG; DAHP (3-deoxy-D-arabino-heptulosonate 7-phosphate synthase) gene
pobA; 4-hydroxybenzoate hydroxylase gene
dca; 4-hydroxybenzoate decarboxylase gene
poxF; phenol 2-monooxygenase gene Example 2

Experiment of Phenol Production Using *Corynebacterium glutamicum* Phenol-Producing Gene Transgenic Strains and *Corynebacterium Glutamicum* by-Product Formation Pathway Disruptants Phenol production was compared among the *Corynebacterium glutamicum* phenol-producing gene transgenic strains PHE11 to PHE18 prepared in Example 1.

Each of the *Corynebacterium glutamicum* phenol-producing gene transgenic strains (PHE11 to PHE18) was applied to A agar medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4 \cdot 7H_2O$, 1 mL of 0.06% (w/v) $Fe_2SO_4 \cdot 7H_2O$+0.042% (w/v) $MnSO_4 \cdot 2H_2O$, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar were suspended in 1 L of distilled water) containing antibiotics shown in Table 2, and left stand in the dark at 28° C. for 20 hours.

An inoculation loop of each of the *Corynebacterium glutamicum* phenol-producing gene transgenic strains grown on a plate as above was inoculated into a test tube containing 10 mL of A liquid medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4 \cdot 7H_2O$, 1 mL of 0.06% (w/v) $Fe_2SO_4 \cdot 7H_2O$+0.042%

(w/v) MnSO$_4$.2H$_2$O, 1 mL of 0.02% (w/v) biotin solution, 2 mL of 0.01% (w/v) thiamin solution, 2 g of yeast extract, 7 g of vitamin assay casamino acid, and 40 g of glucose were dissolved in 1 L of distilled water) containing antibiotics shown in Table 2, and aerobically cultured with shaking at 28° C. for 15 hours.

Each of the *Corynebacterium glutamicum* phenol-producing gene transgenic strains grown in the above conditions was inoculated to 10 mL of A liquid medium containing the antibiotics, and aerobically cultured with shaking at 33° C. for 24 hours.

For quantitative determination of phenol, the reaction mixture sampled 24 hours later was centrifuged (15,000×g at 4° C. for 10 minutes), and the obtained supernatant was analyzed by liquid chromatography.

Also, using *Corynebacterium glutamicum* wild strain, phenol production was attempted in the same manner. However, no phenol production was detected.

The amounts of phenol produced by the strains are shown in Table 2 below.

TABLE 2

Experiment of phenol production using phenol-producing gene transgenic strains

| Strain | Host strain *Corynebacterium glutamicum* | Transfected gene (gene name/origin) | | | Antibiotics added to medium | Amount of phenol production (mM) |
|---|---|---|---|---|---|---|
| PHE11 | Wild strain | ubiC/EC | bsdBCD/BS | — | A, B | 0.4 |
| PHE12 | | ubiC/EC | bsdBCD/BS | aroG/C | A, B, C | 0.9 |
| PHE13 | ΔpobA | ubiC/EC | bsdBCD/BS | — | A, B | 0.8 |
| PHE14 | | ubiC/EC | bsdBCD/BS | aroG/C | A, B, C | 1.8 |
| PHE15 | Wild strain | ubiC/PP | bsdBCD/BS | — | A, B | 1.1 |
| PHE16 | | ubiC/PP | bsdBCD/BS | aroG/C | A, B, C | 3.5 |
| PHE17 | ΔpobA | ubiC/PP | bsdBCD/BS | — | A, B | 1.6 |
| PHE18 | | ubiC/PP | bsdBCD/BS | aroG/C | A, B, C | 6.3 |

<Abbreviation for gene origin>
BS; *Bacillus subtilis*
EC; *Escherichia coli*
PP; *Pseudomonas putida*
CG; *Corynebacterium glutamicum*
<Antibiotics added to the medium>
A; Chloramphenicol 5 µg/mL
B; Kanamycin 50 µg/mL
C; Zeocin 25 µg/mL
<Gene name>
ubiC; chorismate-pyruvate lyase gene
bsdBCD; 4-hydroxybenzoate decarboxylase gene
aroG; DAHP (3-deoxy-D-arabino-heptulosonate 7-phosphate synthase) gene
pobA; 4-hydroxybenzoate hydroxylase gene As shown in Table 2, *Corynebacterium glutamicum* PHE11 produced 0.4 mM of phenol, PHE12 produced 0.9 mM of phenol, PHE13 produced 0.8 mM of phenol, PHE14 produced 1.8 mM of phenol, PHE15 produced 1.1 mM of phenol, PHE16 produced 3.5 mM of phenol, PHE17 produced 1.6 mM of phenol, and PHE18 produced 6.3 mM of phenol in the respective culture media.

These results show the following.
(1) Practical phenol production from glucose was first achieved by a *Corynebacterium glutamicum* transfected with both a ubiC gene and a bsdBCD gene.
(2) In the case where the ubiC gene derived from *Pseudomonas putida* was used, higher phenol productivity can be obtained than in the case where the ubiC gene derived from *Escherichia coli* was used.
(3) Phenol production was augmented by the use of an aroG gene in addition to a ubiC gene and a bsdBCD gene.
(4) Phenol production was further improved by pobA gene disruption.

Example 3

Experiment of Phenol Production Using *Corynebacterium glutamicum* Phenol-Producing Gene Transgenic Strains and *Corynebacterium Glutamicum* by-Product Formation Pathway Disruptants Phenol production was compared among the *Corynebacterium glutamicum* phenol-producing gene transgenic strains PHE19-1 to PHE19-12 prepared in Example 1.

Each of the *Corynebacterium glutamicum* phenol-producing gene transgenic strains (PHE19-1 to PHE19-12) was applied to A agar medium (2 g of (NH$_2$)$_2$CO, 7 g of (NH$_4$)$_2$SO$_4$, 0.5 g of KH$_2$PO$_4$, 0.5 g of K$_2$HPO$_4$, 0.5 g of MgSO$_4$.7H$_2$O, 1 mL of 0.06% (w/v) Fe$_2$SO$_4$.7H$_2$O+0.042% (w/v) MnSO$_4$.2H$_2$O, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar were suspended in 1 L of distilled water) containing antibiotics, namely, 5 µg/mL of chloramphenicol, 50 µg/mL of kanamycin, and 25 µg/mL of zeocin, and left stand in the dark at 28° C. for 20 hours.

An inoculation loop of each of the *Corynebacterium glutamicum* phenol-producing gene transgenic strains grown on a plate as above was inoculated into a test tube containing 10 mL of A liquid medium (2 g of (NH$_2$)$_2$CO, 7 g of (NH$_4$)$_2$SO$_4$, 0.5 g of KH$_2$PO$_4$, 0.5 g of K$_2$HPO$_4$, 0.5 g of MgSO$_4$.7H$_2$O, 1 mL of 0.06% (w/v) Fe$_2$SO$_4$.7H$_2$O+0.042% (w/v) MnSO$_4$.2H$_2$O, 1 mL of 0.02% (w/v) biotin solution, 2 mL of 0.01% (w/v) thiamin solution, 2 g of yeast extract, 7 g of vitamin assay casamino acid, and 40 g of glucose were dissolved in 1 L of distilled water) containing antibiotics, namely, 5 µg/mL of chloramphenicol, 50 µg/mL of kanamycin, and 25 µg/mL of zeocin, and aerobically cultured with shaking at 28° C. for 15 hours.

Each of the *Corynebacterium glutamicum* phenol-producing gene transgenic strains grown in the above conditions was inoculated to 10 mL of A liquid medium containing antibiotics, namely, 5 μg/mL of chloramphenicol, 50 μg/mL of kanamycin, and 25 μg/mL of zeocin, and aerobically cultured with shaking at 33° C. for 24 hours.

For quantitative determination of phenol, the reaction mixture sampled 24 hours later was centrifuged (15,000×g at 4° C. for 10 minutes), and the obtained supernatant was analyzed by liquid chromatography.

The amounts of phenol produced by the strains are shown in Table 3 below.

TABLE 3

Experiment of phenol production using phenol-producing gene transgenic strains

| Strain | Host strain Corynebacterium glutamicum | Transfected gene (gene name/origin) | | | Amount of phenol production (mM) |
|---|---|---|---|---|---|
| PHE19-1 | ΔpobAΔpoxF | ubiC/PP | bsdBCD/BS | aroG/CG | 7.6 |
| PHE19-2 | | ubiC/PP | dca/BAE | aroG/CG | 7.3 |
| PHE19-3 | | ubiC/PP | dca/BSS | aroG/CG | 7.3 |
| PHE19-4 | | ubiC/PP | dca/CKO | aroG/CG | 7.2 |
| PHE19-5 | | ubiC/PP | dca/EAE | aroG/CG | 8.5 |
| PHE19-6 | | ubiC/PP | dca/ECL | aroG/CG | 8.5 |
| PHE19-7 | | ubiC/PP | dca/EHO | aroG/CG | 8.3 |
| PHE19-8 | | ubiC/PP | dca/ESA | aroG/CG | 8.4 |
| PHE19-9 | | ubiC/PP | dca/ECK | aroG/CG | 8.5 |
| PHE19-10 | | ubiC/PP | dca/EFE | aroG/CG | 8.3 |
| PHE19-11 | | ubiC/PP | dca/PPY | aroG/CG | 7.0 |
| PHE19-12 | | ubiC/PP | dca/PAM | aroG/CG | 7.1 |

<Abbreviation for gene origin>
BS; *Bacillus subtilis*
EC; *Escherichia coli*
PP; *Pseudomonas putida*
CG; *Corynebacterium glutamicum*
BAE; *Bacillus atrophaeus*
BSS; *Bacillus subtilis* subsp. *spizizenii*
CKO; *Citrobacter koseri*
EAE; *Enterobacter aerogenes*
ECL; *Enterobacter cloacae*
EHO; *Enterobacter hormaechei*
ESA; *Enterobacter sakazakii*
ECK; *Escherichia coli* W
EFE; *Escherichia fergusonii*
PPY; *Paenibacillus polymyxa*
PAM; *Pantoea ananatis*
<Gene name>
ubiC; chorismate-pyruvate lyase gene
bsdBCD; 4-hydroxybenzoate decarboxylase gene
aroG; DAHP (3-deoxy-D-arabino-heptulosonate 7-phosphate synthase) gene
pobA; 4-hydroxybenzoate hydroxylase gene
dca; 4-hydroxybenzoate decarboxylase gene
poxF; phenol 2-monooxygenase gene Comparison of the results in Table 3 with the result of PHE18 in Table 2 shows that poxF-gene disruption in addition to pobA-gene disruption further improved the phenol productivity.

As compared with the *Corynebacterium glutamicum* ΔpobAΔpoxF transfected with a bsdBCD gene derived from *Bacillus subtilis* in combination with a ubiC gene and an aroG gene, the counterpart transfected with a dca gene derived from *Bacillus* atrophaeus, a dca gene derived from *Bacillus subtilis* subsp. *spizizenii*, a dca gene derived from *Citrobacter koseri*, a dca gene derived from *Enterobacter aerogenes*, a dca gene derived from *Enterobacter cloacae*, a dca gene derived from *Enterobacter* hormaechei, a dca gene derived from *Enterobacter* sakazakii, a dca gene derived from *Escherichia coli*, a dca gene derived from *Escherichia fergusonii*, a dca gene derived from *Paenibacillus polymyxa*, or a dca gene derived from *Pantoea ananatis* instead of the bsdBCD gene derived from *Bacillus subtilis* showed an equal or a higher phenol productivity.

Example 4

Experiment of Phenol Production Using *Corynebacterium glutamicum* Phenol-Producing Gene Transgenic Strains and *Corynebacterium Glutamicum* by-Product Formation Pathway Disruptants Phenol production was compared among the *Corynebacterium glutamicum* phenol-producing gene transgenic strains PHE19-6 and PHE20-1 to PHE20-14 prepared in Example 1.

Each of the *Corynebacterium glutamicum* phenol-producing gene transgenic strains (PHE19-6 and PHE20-1 to PHE20-14) was applied to A agar medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar were suspended in 1 L of distilled water) containing antibiotics, namely, 5 μg/mL of chloramphenicol, 50 μg/mL of kanamycin, and 25 μg/mL of zeocin, and left stand in the dark at 28° C. for 20 hours.

An inoculation loop of each of the *Corynebacterium glutamicum* phenol-producing gene transgenic strains grown on a plate as above was inoculated into a test tube containing 10 mL of A liquid medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, and 40 g of glucose were dissolved in 1 L of distilled water) containing antibiotics, namely, 5 μg/mL of chloramphenicol, 50 μg/mL of kanamycin, and 25 μg/mL of zeocin, and aerobically cultured with shaking at 28° C. for 15 hours.

Each of the *Corynebacterium glutamicum* phenol-producing gene transgenic strains grown in the above conditions was inoculated to 10 mL of A liquid medium containing antibiotics, namely, 5 μg/mL of chloramphenicol, 50 μg/mL of kanamycin, and 25 μg/mL of zeocin, and aerobically cultured with shaking at 33° C. for 24 hours.

For quantitative determination of phenol, the reaction mixture sampled 24 hours later was centrifuged (15,000×g at 4° C. for 10 minutes), and the obtained supernatant was analyzed by liquid chromatography.

The amounts of phenol produced by the strains are shown in Table 4 below.

TABLE 4

Experiment of phenol production using phenol-producing gene transgenic strains

| Strain | Host strain Corynebacterium glutamicum | Transfected gene (gene name/origin) | | | Amount of phenol production (mM) |
|---|---|---|---|---|---|
| PHE19-6 | ΔpobAΔpoxF | ubiC/PP | dca/ECL | aroG/CG | 8.5 |
| PHE20-1 | | ubiC/EC | dca/ECL | aroG/CG | 8.3 |

TABLE 4-continued

Experiment of phenol production using phenol-producing gene transgenic strains

| Strain | Host strain Corynebacterium glutamicum | Transfected gene (gene name/origin) | | | Amount of phenol production (mM) |
|---|---|---|---|---|---|
| PHE20-2 | | ubiC/ACB | dca/ECL | aroG/CG | 3.5 |
| PHE20-3 | | ubiC/AVN | dca/ECL | aroG/CG | 7.5 |
| PHE20-4 | | ubiC/CSA | dca/ECL | aroG/CG | 4.4 |
| PHE20-5 | | ubiC/CKO | dca/ECL | aroG/CG | 7.7 |
| PHE20-6 | | ubiC/CIT | dca/ECL | aroG/CG | 9.7 |
| PHE20-7 | | ubiC/ECL | dca/ECL | aroG/CG | 9.3 |
| PHE20-8 | | ubiC/MAQ | dca/ECL | aroG/CG | 4.1 |
| PHE20-9 | | ubiC/MME | dca/ECL | aroG/CG | 3.9 |
| PHE20-10 | | ubiC/PAM | dca/ECL | aroG/CG | 11.8 |
| PHE20-11 | | ubiC/PHA | dca/ECL | aroG/CG | 8.4 |
| PHE20-12 | | ubiC/REH | dca/ECL | aroG/CG | 4.5 |
| PHE20-13 | | ubiC/SPC | dca/ECL | aroG/CG | 2.2 |
| PHE20-14 | | ubiC/TBD | dca/ECL | aroG/CG | 1.9 |

<Abbreviation for gene origin>
PP; *Pseudomonas putida*
ECL; *Enterobacter cloacae*
CG; *Corynebacterium glutamicum*
EC; *Escherichia coli*
ACB; *Acinetobacter baumannii*
AVN; *Azotobacter vinelandii*
CSA; *Chromohalobacter salexigens*
CKO; *Citrobacter koseri*
CIT; *Citrobacter youngae*
MAQ; *Marinobacter aquaeolei*
MME; *Marinomonas mediterranea*
PAM; *Pantoea ananatis*
PHA; *Pseudoalteromonas haloplanktis*
REH; *Ralstonia eutropha*
SPC; *Shewanella putrefaciens*
TBD; *Thiobacillus denitrificans*
<Gene name>
ubiC; chorismate-pyruvate lyase gene
aroG; DAHP (3-deoxy-D-arabino-heptulosonate 7-phosphate synthase) gene
pobA; 4-hydroxybenzoate hydroxylase gene
dca; 4-hydroxybenzoate decarboxylase gene
poxF; phenol 2-monooxygenase gene The results in Table 4 show that as is the case in the *Corynebacterium glutamicum* ΔpobAΔpoxF transfected with a ubiC gene derived from *Pseudomonas putida* in combination with a ubiC gene and an aroG gene, the counterpart transfected with a ubiC gene derived from *Escherichia coli*, a ubiC gene derived from *Acinetobacter baumannii*, a ubiC gene derived from *Azotobacter vinelandii*, a ubiC gene derived from *Chromohalobacter salexigens*, a ubiC gene derived from *Citrobacter koseris*, a ubiC gene derived from *Citrobacter youngae*, a ubiC gene derived from *Marinobacter aquaeolei*, a ubiC gene derived from *Marinomonas mediterranea*, a ubiC gene derived from *Pantoea ananatis*, a ubiC gene derived from *Pseudoalteromonas haloplanktis*, a ubiC gene derived from *Ralstonia eutropha*, a ubiC gene derived from *Shewanella putrefaciens*, or a ubiC gene derived from *Thiobacillus denitrificans* instead of the ubiC gene derived from *Pseudomonas putida* showed a significant phenol productivity.

Example 5

Experiment of Phenol Production Using *Corynebacterium glutamicum* PHE18 Under Reducing Conditions The *Corynebacterium glutamicum* phenol-producing strain PHE18 created in Example 1 was applied to A agar medium containing 5 μg/mL of chloramphenicol, 50 μg/mL of kanamycin, and 25 μg/mL of zeocin, and left stand in the dark at 28° C. for 20 hours.

An inoculation loop of the *Corynebacterium glutamicum* phenol-producing strain PHE18 grown on a plate as above was inoculated into a test tube containing 10 mL of A liquid medium containing 5 μg/mL of chloramphenicol, 50 μg/mL of kanamycin, and 25 μg/mL of zeocin, and aerobically cultured with shaking at 28° C. for 10 hours.

The *Corynebacterium glutamicum* phenol-producing strain PHE18 grown in the above conditions was inoculated into a 2 L-conical flask containing 500 mL of A liquid medium containing 5 μg/mL of chloramphenicol, 50 μg/mL of kanamycin, and 25 μg/mL of zeocin, and aerobically cultured with shaking at 33° C. for 15 hours.

The bacterial cells of the strain cultured and proliferated as above were collected by centrifugation (5,000×g at 4° C. for 15 minutes). The obtained bacterial cells were suspended in 50 mL of BT (−urea) liquid medium (0.7% ammonium sulfate, 0.05% potassium dihydrogen phosphate, 0.05% dipotassium hydrogen phosphate, 0.05% magnesium sulfate heptahydrate, 0.0006% iron sulfate heptahydrate, 0.00042% manganese sulfate hydrate, 0.00002% biotin and 0.00002% thiamine hydrochloride) so that the final concentration of the bacterial cell was 10%. To a 100-mL medium bottle, 60 mL of the cell suspension was transferred, glucose was added, and the reaction was allowed to proceed under reducing conditions (the ORP of the reaction mixture: −450 mV) at 33° C. with stirring. As for the glucose addition, glucose was added so as to be 5% in concentration at first, and another 5% was added 12 hours later. During the reaction, the pH of the reaction mixture was kept at or above 7.0 through addition of 2.5 N aqueous ammonia controlled by a pH controller (Type: DT-1023 made by Able).

A sample of the reaction mixture was centrifuged (15,000×g at 4° C. for 10 minutes), and the obtained supernatant was used for quantitative determination of phenol.

As a result, in the reaction under reducing conditions, the *Corynebacterium glutamicum* phenol-producing strain PHE18 produced 9.2 mM of phenol 24 hours after the start of the reaction.

Thus, it was revealed that the transformant of the present invention further efficiently produced phenol under reducing conditions.

Example 6

Test for Suitability as a Host for Phenol Production (1) Influence of Phenol on Aerobic Proliferation A growth inhibition test in aerobic culture was performed to examine the influence of phenol on *Corynebacterium glutamicum*, *Escherichia coli*, and *Pseudomonas putida*. *Pseudomonas putida* S12, which was used for the test, is reported to be a solvent-resistant strain. In the report, disclosed is an unparalleled technology using the strain as a host in phenol production.

*Corynebacterium glutamicum* R was applied to A agar medium (2 g of $(NH_2)_2C$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$ + 0.042% (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar were suspended in 1 L of distilled water) and was left stand in the dark at 33° C. for 15 hours.

An inoculation loop of the *Corynebacterium glutamicum* R grown on a plate as above was inoculated into a test tube containing 10 mL of A liquid medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, and 40 g of glucose were suspended in 1 L of distilled water) and was aerobically cultured with shaking at 33° C. for 13 hours.

The *Corynebacterium glutamicum* R grown in the above conditions was inoculated into 100 mL of A liquid medium in such a way that the initial bacterial cell concentration would be $OD_{610}$=0.05, phenol was added at the same time in such a way that the final concentration would be 0, 0.16, 0.2, 0.24, or 0.32 mM, and aerobic culture was performed with shaking at 33° C. The growth of bacterial cells was determined by absorbance measurement at $OD_{610}$.

*Escherichia coli* JM109 was applied to LB agar medium (1% polypeptone, 0.5% yeast extract, 0.5% NaCl and 1.5% agar) and was left stand in the dark at 37° C. for 15 hours.

An inoculation loop of the *Escherichia coli* JM109 grown on a plate as above was inoculated into a test tube containing 10 mL of LB liquid medium (1% polypeptone, 0.5% yeast extract, and 0.5% NaCl), and aerobic culture was performed with shaking at 37° C. for 13 hours.

The *Escherichia coli* JM109 grown in the above conditions was inoculated into 100 mL of LB liquid medium in such a way that the initial bacterial cell concentration would be $OD_{610}$=0.05, phenol was added at the same time in such a way that the final concentration would be 0, 0.16, or 0.20 mM, and aerobic culture was performed with shaking at 37° C. The growth of bacterial cells was determined by absorbance measurement at $OD_{610}$.

*Pseudomonas putida* F1 and S12 were applied to LB agar medium (1% polypeptone, 0.5% yeast extract, 0.5% NaCl and 1.5% agar) and were left stand in the dark at 30° C. for 15 hours.

An inoculation loop of each of the *Pseudomonas putida* F1 and S12 grown on a plate as above was inoculated into a test tube containing 10 mL of LB (+glucose) liquid medium (1% polypeptone, 0.5% yeast extract, 0.5% NaCl and 0.4% glucose), and aerobic culture was performed with shaking at 30° C. for 13 hours.

Figure 4:
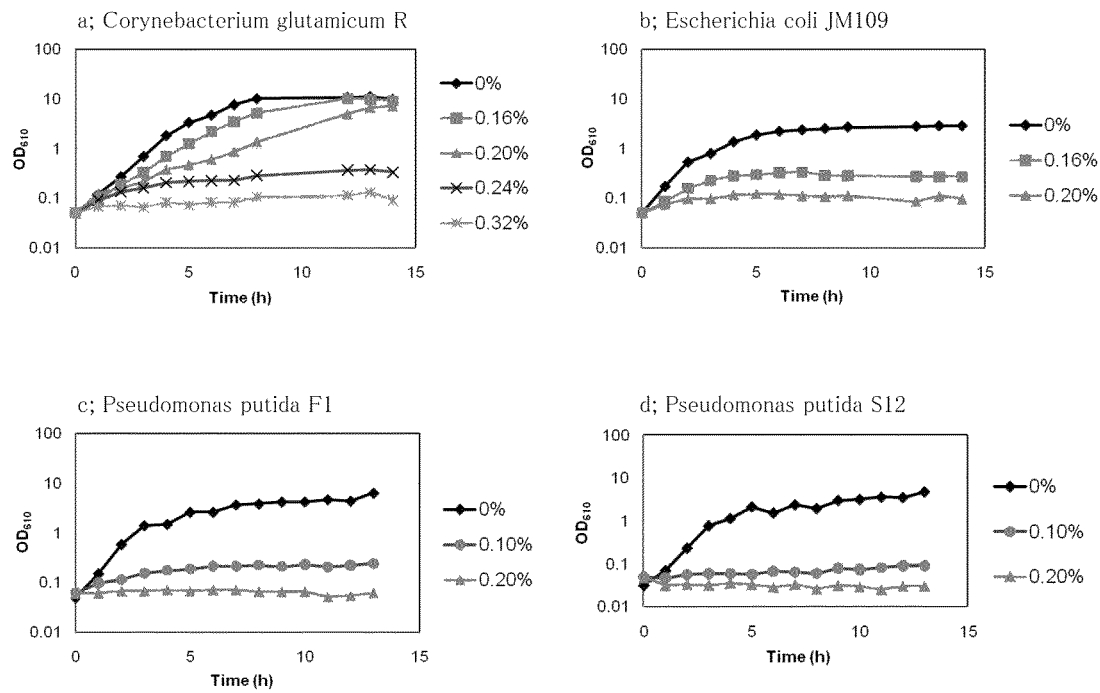
FIG. 4 shows the influence of phenol on proliferation of various microorganisms under aerobic conditions.

The *Pseudomonas putida* F1 and S12 grown in the above conditions were each inoculated into 100 mL of LB (+glucose) liquid medium in such a way that the initial bacterial cell concentration would be $OD_{610}$=0.05, phenol was added at the same time in such a way that the final concentration would be 0, 0.10, or 0.20 mM, and aerobic culture was performed with shaking at 30° C. The growth of bacterial cells was determined by absorbance measurement at $OD_{610}$. FIG. 4 shows analysis results of the influence of phenol addition on aerobic proliferation.

The proliferation of *Escherichia coli* was significantly affected by 0.16% phenol and completely inhibited by 0.20% phenol.

*Pseudomonas putida* F1, and *Pseudomonas putida* S12, which was reported as a solvent-resistant strain, showed a similar tendency, and the proliferation thereof was significantly affected by 0.10% phenol and completely inhibited by 0.20% phenol.

In contrast, the proliferation of *Corynebacterium glutamicum* was hardly affected by 0.16% phenol, which significantly affected the proliferation of *Escherichia coli*. Even in the presence of 0.20% phenol, which completely inhibited the proliferation of *Escherichia coli* and *Pseudomonas putida*, *Corynebacterium glutamicum* showed favorable growth. Further, *Corynebacterium glutamicum* was able to proliferate in the presence of 0.24% phenol.

Thus, it was shown that *Corynebacterium glutamicum* has a higher resistance to phenol as compared with *Escherichia coli* and *Pseudomonas putida*, and is highly suitable as a host in phenol production.

(2) Influence of Phenol on Saccharide Metabolism Under Reducing Conditions

*Corynebacterium glutamicum* R was applied to A agar medium and was left stand in the dark at 33° C. for 20 hours.

An inoculation loop of the *Corynebacterium glutamicum* R grown on a plate as above was inoculated into a test tube containing 10 mL of A liquid medium and was aerobically cultured with shaking at 33° C. for 15 hours.

The *Corynebacterium glutamicum* R grown in the above conditions was inoculated into a 2 L-conical flask containing 500 mL of A liquid medium and was aerobically cultured with shaking at 33° C. for 15 hours.

The bacterial cells cultured and proliferated as above were collected by centrifugation (5,000×g at 4° C. for 15 minutes). The obtained bacterial cells were suspended in BT (−urea) liquid medium (0.7% ammonium sulfate, 0.05% potassium dihydrogen phosphate, 0.05% dipotassium hydrogen phosphate, 0.05% magnesium sulfate heptahydrate, 0.0006% iron sulfate heptahydrate, 0.00042% manganese sulfate hydrate, 0.00002% biotin and 0.00002% thiamine hydrochloride) so that the concentration of the bacterial cell was 10% (w/v). To a 100-mL medium bottle, 60 mL of the cell suspension was transferred, glucose and phenol were added so as to be 8% and 0, 0.24, 0.38, or 0.46 mM in concentration, respectively, and the reaction was allowed to proceed under reducing conditions (the ORP of the reaction mixture: −450 mV) in a water bath kept at 33° C. with stirring. During the reaction, the pH of the reaction mixture was kept at or above 7.0 through addition of 2.5N aqueous ammonia controlled by a pH controller (Type: DT-1023 made by Able).

Figure 5:
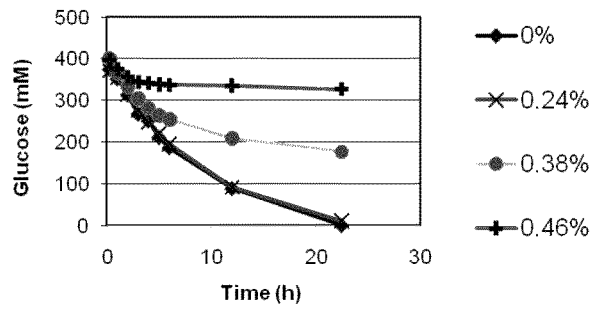
FIG. 5 shows the influence of phenol on the saccharide consumption by *Corynebacterium* under reducing conditions.

FIG. 5 shows the influence of phenol on the saccharide metabolism in *Corynebacterium glutamicum* R under reducing conditions.

Under reducing conditions, even in the presence of 0.24% phenol, which caused proliferation inhibition in aerobic culture, no influence of phenol was observed, and the saccharide consumption was comparable to that in the case free from phenol.

Further, saccharide consumption was observed even in the presence of 0.38% phenol, and was slightly observed even in the presence of 0.46% phenol.

Thus, it was shown that *Corynebacterium glutamicum* has a higher resistance to phenol under reducing conditions as compared with in aerobic culture, and that phenol production using *Corynebacterium glutamicum* as a host under reducing conditions is advantageous as compared with the production under aerobic conditions.

INDUSTRIAL APPLICABILITY

According to the process of the present invention, phenol can be produced with a practical efficiency using microorganisms.

The invention claimed is:

1. A phenol-producing transformant, wherein the phenol-producing transformant is a *Corynebacterium* transformed with a *Pantoea ananatis* chorismate-pyruvate lyase gene and an *Enterobacter cloacae* 4-hydroxybenzoate decarboxylase gene.

2. The phenol-producing transformant of claim 1, wherein the *Pantoea ananatis* chorismate-pyruvate lyase gene consists of the nucleotide sequence of SEQ ID NO: 89.

3. The phenol-producing transformant of claim 1, wherein the *Enterobacter cloacae* 4-hydroxybenzoate decarboxylase gene consists of the nucleotide sequence of SEQ ID NO: 56.

4. The phenol-producing transformant of claim 1, wherein a 4-hydroxybenzoate hydroxylase gene on the chromosome of the *Corynebacterium* is disrupted or deleted.

5. The phenol-producing transformant of claim 1, wherein a phenol 2-monooxygenase gene on the chromosome of the *Corynebacterium* is disrupted or deleted.

6. The phenol-producing transformant of claim 1, wherein the *Corynebacterium* is a *Corynebacterium glutamicum*.

7. The phenol-producing transformant of claim 1, wherein the *Corynebacterium* is *Corynebacterium glutamicum* R having accession number FERM BP-18976, ATCC13032, or ATCC13869.

8. The phenol-producing transformant of claim 7, wherein the *Corynebacterium* is *Corynebacterium glutamicum* R having accession number FERM BP-18976, or ATCC13032 or ATCC13869, and wherein a 4-hydroxybenzoate hydroxylase gene on the chromosome of the *Corynebacterium glutamicum* is disrupted or deleted.

9. The phenol-producing transformant of claim 7, wherein the *Corynebacterium* is *Corynebacterium glutamicum* R having accession number FERM BP-18976, or ATCC13032 or ATCC13869, and wherein a phenol 2-monooxygenase gene on the chromosome of the *Corynebacterium glutamicum* is disrupted or deleted.

10. A process for producing phenol, which comprises reacting the phenol-producing transformant of claim 1 with a saccharide in a reaction mixture under reducing conditions to produce phenol, and collecting phenol from the reaction mixture.

11. The process of claim 10, wherein the phenol-producing transformant does not proliferate in the reacting step.

12. The process of claim 10, wherein the oxidation-reduction potential of the reaction mixture under reducing conditions is −200 mV to −500 mV.

13. The process of claim 10, wherein the saccharide is selected from the group consisting of glucose, fructose, mannose, xylose, arabinose, galactose, sucrose, maltose, lactose, cellobiose, xylobiose, trehalose, and mannitol.

14. The phenol-producing transformant of claim 1, wherein expression of a *Corynebacterium* aroG gene which encodes an enzyme having 3-deoxy-D-arabino-heptulosonate 7-phosphate (DAHP) synthase activity is increased in the phenol-producing transformant as compared with a corresponding wild-type *Corynebacterium*.

* * * * *